US012644122B2

(12) United States Patent
Biffi et al.

(10) Patent No.: US 12,644,122 B2
(45) Date of Patent: Jun. 2, 2026

(54) COMPOSITIONS AND METHODS FOR TREATING AMYOTROPHIC LATERAL SCLEROSIS

(71) Applicants: The Children's Medical Center Corporation, Boston, MA (US); Dana-Farber Cancer Institute, Inc., Boston, MA (US)

(72) Inventors: Alessandra Biffi, Boston, MA (US); Marco Peviani, Boston, MA (US); Francisco J. Molina-Estevez, Boston, MA (US)

(73) Assignees: The Children's Medical Center Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 961 days.

(21) Appl. No.: 17/710,418

(22) Filed: Mar. 31, 2022

(65) Prior Publication Data

US 2022/0290157 A1 Sep. 15, 2022

Related U.S. Application Data

(63) Continuation of application No. PCT/US2020/053826, filed on Oct. 1, 2020.

(60) Provisional application No. 62/908,942, filed on Oct. 1, 2019.

(51) Int. Cl.
*C12N 15/113* (2010.01)
*A61K 35/28* (2015.01)
*A61P 25/28* (2006.01)

(52) U.S. Cl.
CPC .......... *C12N 15/1137* (2013.01); *A61K 35/28* (2013.01); *A61P 25/28* (2018.01); *C12N 2310/141* (2013.01); *C12N 2310/531* (2013.01)

(58) Field of Classification Search
None
See application file for complete search history.

(56) References Cited

U.S. PATENT DOCUMENTS

| | | | | |
|---|---|---|---|---|
| 8,093,209 | B2 | 1/2012 | Laskowilz et al. | |
| 10,851,375 | B2 * | 12/2020 | Mueller | C12N 15/86 |
| 2010/0166759 | A1 | 7/2010 | Berezin et al. | |
| 2014/0235697 | A1 | 8/2014 | Weiner et al. | |
| 2016/0256492 | A1 | 9/2016 | Naldini et al. | |
| 2018/0161357 | A1 | 6/2018 | Jackson et al. | |
| 2023/0136245 | A1 * | 5/2023 | Gannon | A61P 25/28 424/93.2 |

FOREIGN PATENT DOCUMENTS

| | | | |
|---|---|---|---|
| KR | 101625755 | B1 | 5/2016 |
| WO | 2010012667 | A1 | 2/2010 |
| WO | 2015164750 | A2 | 10/2015 |
| WO | 2018071898 | A1 | 4/2018 |
| WO | 2018136434 | A1 | 7/2018 |
| WO | 2018136435 | A1 | 7/2018 |
| WO | 2021026294 | A1 | 2/2021 |

OTHER PUBLICATIONS

Bae et al., "Macrophages Generate Reactive Oxygen Species in Response to Minimally Oxidized Low-Density Lipoprotein: Toll-Like Receptor 4—and Spleen Tyrosine Kinase-Dependent Activation of NADPH Oxidase 2," Circulation Research, Jan. 30, 2009, vol. 104, pp. 210-218.
Bofill-De Ros et al., "Genome-wide miR-155 and miR-802 target gene identification in the hippocampus of Ts65Dn Down syndrome mouse model by miRNA sponges," BMC Genomics, 2015, vol. 16, Article No. 907, pp. 1-12.
Brendel et al., "Lineage-specific BCL11A knockdown circumvents toxicities and reverses sickle phenotype," The Journal of Clinical Investigation, Oct. 2016, vol. 126, No. 10, pp. 3868-3878.
Butovsky et al., "Targeting miR-155 restores abnormal microglia and attenuates disease in SOD1 mice," Annals of Neurology, Jan. 2015, vol. 77, No. 1, pp. 75-99.
Hingtgen et al., "Nox2-containing NADPH oxidase and Akt activation play a key role in angiotensin II-induced cardiomyocyte hypertrophy," Physiological Genomics, 2006, vol. 26, pp. 180-191.
Juarez-Rebollar et al., "Immunohistochemical study of Metallothionein in patients with temporal lobe epilepsy," Journal of Clinical Neuroscience, 2017, pp. 1-4.
Juarez-Rebollar et al., "Metallothionein in Brain Disorders," Oxidative Medicine and Cellular Longevity, 2017, vol. 2017, Article No. 5828056, pp. 1-12.
Parisi et al., "Dysregulated microRNAs in amyotrophic lateral sclerosis microglia modulate genes linked to neuroinflammation," Cell Death and Disease, 2013, vol. 4, e959, pp. 1-10.
Ruttkay-Nedecky et al., "The Role of Metallothionein in Oxidative Stress," International Journal of Molecular Sciences, 2013, vol. 14, pp. 6044-6066.
Qi et al., "Myricitrin Modulates NADPH Oxidase-Dependent ROS Production to Inhibit Endotoxin-Mediated Inflammation by Blocking the JAK/STAT1 and NOX2/p47phox Pathways," Oxidative Medicine and Cellular Longevity, Jun. 20, 2017, vol. 2017, Article ID 9738745, pp. 1-20.
International Search Report and Written Opinion mailed Feb. 9, 2021 in corresponding International PCT Patent Application No. PCT/US2020/053826 (18 pages).
Atagi et al., "Apolipoprotein E Is a Ligand for Triggering Receptor Expressed on Myeloid Cells 2 (TREM2)," The Journal of Biological Chemistry, Oct. 23, 2015, vol. 290, No. 43, pp. 26043-26050.
Office Action dated Jan. 13, 2025 in Chinese Patent Application No. 202080068974.7 (6 pages).
English translation of Office Action dated Jan. 13, 2025 in Chinese Patent Application No. 202080068974.7 (10 pages).

* cited by examiner

*Primary Examiner* — Blaine Lankford
(74) *Attorney, Agent, or Firm* — Greenberg Traurig, LLP; Melissa Hunter-Ensor; Nathan Hsu

(57) ABSTRACT

The present disclosure features methods and compositions for treating amyotrophic lateral sclerosis (ALS). The disclosed methods comprise administering to a subject having or suspected of having ALS a hematopoietic stem progenitor cell expressing at least one neuroprotective agent. The compositions disclosed comprise hematopoietic stem progenitor cells transduced to express a neuroprotective agent.

8 Claims, 14 Drawing Sheets

Specification includes a Sequence Listing.

B

SEQUENCE LISTING

```
<160> NUMBER OF SEQ ID NOS: 22

<210> SEQ ID NO 1
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(45)
<223> OTHER INFORMATION: a, c, u, g, unknown or other
<220> FEATURE:
<221> NAME/KEY: modified_base
<222> LOCATION: (61)..(81)
<223> OTHER INFORMATION: a, c, u, g, unknown or other

<400> SEQUENCE: 1

ccuggccucc ugcagugcca cgcunnnnnn nnnnnnnnnn nnnnncucca ugugguagag     60

nnnnnnnnnn nnnnnnnnnn nagugcggca caugcuuacc agcu                     104


<210> SEQ ID NO 2
```

-continued

<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
accccuauca caggagcauu aa 22

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
uuaaugcuaa uugugauagg ggu 23

<210> SEQ ID NO 4
<211> LENGTH: 512
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
agactctgtc tcaaaaaaaa aaaaaaaaaa aaaaaaagag agagagaaaa aggaagttag 60
aaaaacagcc ctagaggccc tacattctga gtaataggag ttccagaaag gaagtgattg 120
ctgcacaaca taaatttgaa aagaaagaga agtgagaaaa tagagggaag gaaatcaaag 180
aaataatcca acttctgaaa agtaaagaat gagcttccag cgggaaagtg cctgttgagt 240
gcaggcacag tggaggaaat gaagctgggt gtgttgccag gagttggaaa cttgtctgag 300
caacatagcg cgaccctgtg tctacaaaaa aataaaaaca aaacaaaaaa caaccaaaga 360
cttccgaaac agaatggctt tagcctgctc aaccgcacac tggcacctgg ccaacagcat 420
ctcttcatga ttctgaagga caacgatctg cagctcagcc aagcatcagc catctatggc 480
ctaggatgca agaattcagc aatgttacct tc 512

<210> SEQ ID NO 5
<211> LENGTH: 1147
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
agactctgtc tcaaaaaaaa aaaaaaaaaa aaaaaaagag agagagaaaa aggaagttag 60
aaaaacagcc ctagaggccc tacattctga gtaataggag ttccagaaag gaagtgattg 120
ctgcacaaca taaatttgaa aagaaagaga agtgagaaaa tagagggaag gaaatcaaag 180
aaataatcca acttctgaaa agtaaagaat gagcttccag cgggaaagtg cctgttgagt 240
gcaggcacag tggaggaaat gaagctgggt gtgttgccag gagttggaaa cttgtctgag 300
caacatagcg cgaccctgtg tctacaaaaa aataaaaaca aaacaaaaaa caaccaaaga 360
cttccgaaac agaatggctt tagcctgctc aaccgcacac tggcacctgg ccaacagcat 420
ctcttcatga ttctgaagga caacgatctg cagctcagcc aagcatcagc catctatggc 480

-continued ctaggatgca agaattcagc aatgttacct tctgcatcac cgcgttgcgg cctcatcagt 540
cccacgactt tgtgcccatt ttactcatga ggagatggag gcccagagag ccagtcagaa 600
agtggctggg ccaggactaa gagtgcagcg cgctgcctcc gtgccctgcg tcaacagctc 660
aaggaactgg ggtgctccgg aaatggggcc aaggctgctg ggcagcagga cgctcagggc 720
cttggcctca ggagagcaaa ttccccactc ggagatcggt cttgttgctg cattttattc 780
atgggaaatc tgaggctaga agagacgaca aacgacacgc cgttggacac acggcaacgt 840
tttagatgtt gggtctggcc gggcggccgt caccggtcac catggggagg aggaggagcc 900
gagagacttg ctcgcggccg gggggaggca gaagcgcgtc ccgcgggaga ggtggctttg 960
aggagtgagc tcccggtccc gcggggacgc gagtgggccc agtgcccggg ctgccaggcg 1020
gggcggggcg gggccgggcg actgagaggg gcggggcctg gcggctggga ggggcggggc 1080
ggatgcgggg acagcggcct ggctaactcc tgcacggcag tgcccttccc ggagcgtgcc 1140
ctcgccg 1147

<210> SEQ ID NO 6
<211> LENGTH: 386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
taggtggctt cacccctctg cctgagcctg agtcctgtcc ctgccaagac tccgcccagc 60
cgacgcccac cccagctttc cctggactca tccctcagca gatatctgga tcctgcctag 120
cctggctcag catgactcat catgcagggt accgcccctg cccacctgtt ccccaatacc 180
gcaattcagg agctgggcag ttccccagag gccctaggaa actccccgcc cccgaccagg 240
ctttctccac tcctcccatc tgaccgcctg ttttctacgc ctcacgaccc tctgagcccc 300
ttggcgcact ccgacataac cacagccagg cctgagaagc cgccagcctc cgcagcgagt 360
gtgagcacgg gactcagaac tggctt 386

<210> SEQ ID NO 7
<211> LENGTH: 2355
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
agactctgtc tcaaaaaaaa aaaaaaaaaa aaaaaaagag agagagaaaa aggaagttag 60
aaaaacagcc ctagaggccc tacattctga gtaataggag ttccagaaag gaagtgattg 120
ctgcacaaca taaatttgaa aagaaagaga agtgagaaaa tagagggaag gaaatcaaag 180
aaataatcca acttctgaaa agtaaagaat gagcttccag cgggaaagtg cctgttgagt 240
gcaggcacag tggaggaaat gaagctgggt gtgttgccag gagttggaaa cttgtctgag 300
caacatagcg cgaccctgtg tctacaaaaa aataaaaaca aaacaaaaaa caaccaaaga 360
cttccgaaac agaatggctt tagcctgctc aaccgcacac tggcacctgg ccaacagcat 420
ctcttcatga ttctgaagga caacgatctg cagctcagcc aagcatcagc catctatggc 480
ctaggatgca agaattcagc aatgttacct tcgagtgcat caccgcgttg cggcctcatc 540

-continued

```
agtcccacga ctttgtgccc attttactca tgaggagatg gaggcccaga gagccagtca    600

gaaagtggct gggccaggac taagagtgca gcgcgctgcc tccgtgccct gcgtcaacag    660

ctcaaggaac tggggtgctc cggaaatggg gccaaggctg ctgggcagca ggacgctcag    720

ggccttggcc tcaggagagc aaattcccca ctcggagatc ggtcttgttg ctgcatttta    780

ttcatgggaa atctgaggct agaagagacg acaaacgaca cgccgttgga cacacggcaa    840

cgttttagat gttgggtctg gccgggcggc cgtcaccggt caccatgggg aggaggagga    900

gccgagagac ttgctcgcgg ccggggggag gcagaagcgc gtcccgcggg agaggtggct    960

ttgaggagtg agctcccggt cccgcgggga cgcgagtggg cccagtgccc gggctgccag   1020

gcggggcggg gcggggccgg gcgactgaga ggggcggggc ctggcggctg ggagggggcgg   1080

ggcggatgcg gggacagcgg cctggctaac tcctgcacgg cagtgccctt cccggagcgt   1140

gccctcgccg ctgcacagtg aggacgggac gcggaggggg cagcgggaac acgccgcccg   1200

catggctgcg acagttggca gcgccgcggg acagagggaa actgaggccg gagccgcaga   1260

ctggacaccc gagggggcga cccggggcag cacttggggc tcggctacgc gcacaggggg   1320

cggcgggcag cagagtctgg gcctccgcgg ccggggttcc accgccggcc gcctccggct   1380

cgcgcaacgg gagggaaaac ttggacaacc ctgccacgcc cagcccttgg ccgcgtggct   1440

tctcctgctc gaagcgcggt cccaggagtg gccgacgctc cctctcctgc ccattccgcg   1500

gatgggcaat cccaggcgga actcccttga gggtctcaga atatctggga gacctcgggc   1560

tcttgatctc cgagacaccc cgtttcgtag tggagaacag tccagatcgg ggaagtttat   1620

tttgcccaaa gccgcataga ggccccctgg ccctcgattc cctctgcggg gctcagcagc   1680

gttgcagcct agacgggtct tactgtgagc cgagcagcct ctgggaccac agaccttccc   1740

ctaccccaac gttagaagcc ggagcccagc aaggagaagc gcgcacctcc tgctgtgaac   1800

gcgcacgacg ccagggcagc tgccagaggc catggcctgg cgtgggcctg gagcccctct   1860

ggccagcctg cacggggcca gggctacggg ataccagcag cgtgccctgg gctggatggc   1920

aggagagaca ggacttgagg ctgtcccaga atgggctcag gcagggcgag gatatcaggg   1980

gaggtggtgt acaggaagca gccgcccagc ttgcctggca cacagcaagc cctgcccatg   2040

aaggcctact gccagaacag tgggcgaggc ccggcgtctc tgtggagtcg gtggggcccg   2100

ggacagggca gcctgaggca ggtttccact ggcggtgaaa ggggccgtgt ggcaaggaca   2160

ggagagccag cctcagccca gcaggggaag gcggcccctg agtctccacc tggctgctgg   2220

cagccccact cggagcatcg gcgaaactga ggcttgccaa agaagccttt gtccagagtc   2280

acgcagctgg cgcggtggag ccagggccag aacccgtgca ggctgatccc agcctgcctt   2340

ctccactgtg ccccg                                                    2355
```

<210> SEQ ID NO 8
<211> LENGTH: 1021
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
taggtggctt cacccctctg cctgagcctg agtcctgtcc ctgccaagac tccgcccagc     60

cgacgcccac cccagctttc cctggactca tccctcagca gatatctgga tcctgcctag    120

cctggctcag catgactcat catgcagggt accgcccctg cccacctgtt ccccaatacc    180
```

-continued

```
gcaattcagg agctgggcag ttccccagag gccctaggaa actccccgcc cccgaccagg    240

ctttctccac tcctcccatc tgaccgcctg ttttctacgc ctcacgaccc tctgagcccc    300

ttggcgcact ccgacataac cacagccagg cctgagaagc cgccagcctc cgcagcgagt    360

gtgagcacgg gactcagaac tggctttgca tcaccgcgtt gcggcctcat cagtcccacg    420

actttgtgcc cattttactc atgaggagat ggaggcccag agagccagtc agaaagtggc    480

tgggccagga ctaagagtgc agcgcgctgc ctccgtgccc tgcgtcaaca gctcaaggaa    540

ctggggtgct ccggaaatgg ggccaaggct gctgggcagc aggacgctca gggccttggc    600

ctcaggagag caaattcccc actcggagat cggtcttgtt gctgcatttt attcatggga    660

aatctgaggc tagaagagac gacaaacgac acgccgttgg acacacggca acgttttaga    720

tgttgggtct ggccgggcgg ccgtcaccgg tcaccatggg gaggaggagg agccgagaga    780

cttgctcgcg gccgggggga ggcagaagcg cgtcccgcgg gagaggtggc tttgaggagt    840

gagctcccgg tcccgcgggg acgcgagtgg gcccagtgcc cgggctgcca ggcggggcgg    900

ggcggggccg ggcgactgag aggggcgggg cctggcggct gggaggggcg gggcggatgc    960

ggggacagcg gcctggctaa ctcctgcacg gcagtgccct tcccggagcg tgccctcgcc   1020

g                                                                   1021
```

<210> SEQ ID NO 9
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
taggtggctt cacccctctg cctgagcctg agtcctgtcc ctgccaagac tccgcccagc     60

cgacgcccac cccagctttc cctggactca tccctcagca gatatctgga tcctgcctag    120

cctggctcag catgactcat catgcagggt accgcccctg cccacctgtt ccccaatacc    180

gcaattcagg agctgggcag ttccccagag gccctaggaa actccccgcc cccgaccagg    240

ctttctccac tcctcccatc tgaccgcctg ttttctacgc ctcacgaccc tctgagcccc    300

ttggcgcact ccgacataac cacagccagg cctgagaagc cgccagcctc cgcagcgagt    360

gtgagcacgg gactcagaac tggcttgagt gcatcaccgc gttgcggcct catcagtccc    420

acgactttgt gcccatttta ctcatgagga gatggaggcc cagagagcca gtcagaaagt    480

ggctgggcca ggactaagag tgcagcgcgc tgcctccgtg ccctgcgtca acagctcaag    540

gaactggggt gctccggaaa tggggccaag gctgctgggc agcaggacgc tcagggcctt    600

ggcctcagga gagcaaattc cccactcgga gatcggtctt gttgctgcat tttattcatg    660

ggaaatctga ggctagaaga gacgacaaac gacacgccgt tggacacacg gcaacgtttt    720

agatgttggg tctggccggg cggccgtcac cggtcaccat ggggaggagg aggagccgag    780

agacttgctc gcggccgggg ggaggcagaa gcgcgtcccg cgggagaggt ggctttgagg    840

agtgagctcc cggtcccgcg gggacgcgag tgggcccagt gcccgggctg ccaggcgggg    900

cggggcgggg ccgggcgact gagaggggcg gggcctggcg gctgggaggg gcggggcgga    960

tgcggggaca gcggcctggc taactcctgc acggcagtgc ccttcccgga gcgtgccctc   1020

gccgctgcac agtgaggacg ggacgcggag ggggcagcgg gaacacgccg cccgcatggc   1080

tgcgacagtt ggcagcgccg cgggacagag ggaaactgag gccggagccg cagactggac   1140
```

-continued

```
acccgagggg gcgacccggg gcagcacttg gggctcggct acgcgcacag ggggcggcgg   1200

gcagcagagt ctgggcctcc gcggccgggg ttccaccgcc ggccgcctcc ggctcgcgca   1260

acgggaggga aaacttggac aaccctgcca cgcccagccc ttggccgcgt ggcttctcct   1320

gctcgaagcg cggtcccagg agtggccgac gctccctctc ctgcccattc cgcggatggg   1380

caatcccagg cggaactccc ttgagggtct cagaatatct gggagacctc gggctcttga   1440

tctccgagac accccgtttc gtagtggaga acagtccaga tcggggaagt ttattttgcc   1500

caaagccgca tagaggcccc ctggccctcg attccctctg cggggctcag cagcgttgca   1560

gcctagacgg gtcttactgt gagccgagca gcctctggga ccacagacct tcccctaccc   1620

caacgttaga agccggagcc cagcaaggag aagcgcgcac ctcctgctgt gaacgcgcac   1680

gacgccaggg cagctgccag aggccatggc ctggcgtggg cctggagccc ctctggccag   1740

cctgcacggg gccagggcta cgggatacca gcagcgtgcc ctgggctgga tggcaggaga   1800

gacaggactt gaggctgtcc cagaatgggc tcaggcaggg cgaggatatc aggggaggtg   1860

gtgtacagga agcagccgcc cagcttgcct ggcacacagc aagccctgcc catgaaggcc   1920

tactgccaga acagtgggcg aggcccggcg tctctgtgga gtcggtgggg cccgggacag   1980

ggcagcctga ggcaggtttc cactggcggt gaaaggggcc gtgtggcaag gacaggagag   2040

ccagcctcag cccagcaggg gaaggcggcc cctgagtctc cacctggctg ctggcagccc   2100

cactcggagc atcggcgaaa ctgaggcttg ccaaagaagc ctttgtccag agtcacgcag   2160

ctggcgcggt ggagccaggg ccagaacccg tgcaggctga tcccagcctg ccttctccac   2220

tgtgccccg                                                           2229


<210> SEQ ID NO 10
<211> LENGTH: 62
<212> TYPE: PRT
<213> ORGANISM: Homo sapiens

<400> SEQUENCE: 10

Met Asp Pro Asn Cys Ser Cys Ala Ala Ala Gly Val Ser Cys Thr Cys
1               5                   10                  15

Ala Ser Ser Cys Lys Cys Lys Glu Cys Lys Cys Thr Ser Cys Lys Lys
            20                  25                  30

Ser Cys Cys Ser Cys Cys Pro Val Gly Cys Ala Lys Cys Ala Gln Gly
        35                  40                  45

Cys Ile Cys Lys Gly Ala Ser Glu Lys Cys Ser Cys Cys Ala
    50                  55                  60


<210> SEQ ID NO 11
<211> LENGTH: 420
<212> TYPE: DNA
<213> ORGANISM: Homo sapiens

<400> SEQUENCE: 11

actccgcctt ccacgtgcac ccactgcctc ttcccttctc gcttgggaac tctagtctcg     60

cctcgggttg caatggaccc caactgctcc tgtgccgctg gtgtctcctg cacctgcgcc    120

agctcctgca agtgcaaaga gtgcaaatgc acctcctgca agaagagctg ctgctcctgc    180

tgccctgtgg gctgtgccaa gtgtgcccag ggctgcatct gcaaaggggc atcggagaag    240

tgcagctgct gcgcctgatg tcgggacagc cctgctccca agtacaaata gagtgacccg    300

taaaatccag gatttttttgt tttttgctac aatcttgacc cctttgctac attccttttt    360

ttctgtgaaa tatgtgaata ataattaaac acttagactt gaaaaaaaaa aaaaaaaaaa    420
```

-continued

<210> SEQ ID NO 12
<211> LENGTH: 65
<212> TYPE: DNA
<213> ORGANISM: Homo sapiens

<400> SEQUENCE: 12
ctgttaatgc taatcgtgat aggggttttt gcctccaact gactcctaca tattagcatt 60
aacag 65

<210> SEQ ID NO 13
<211> LENGTH: 570
<212> TYPE: PRT
<213> ORGANISM: Homo sapiens

<400> SEQUENCE: 13

Met Gly Asn Trp Ala Val Asn Glu Gly Leu Ser Ile Phe Val Ile Leu
1 5 10 15

Val Trp Leu Gly Leu Asn Val Phe Leu Phe Val Trp Tyr Tyr Arg Val
20 25 30

Tyr Asp Ile Pro Pro Lys Phe Phe Tyr Thr Arg Lys Leu Leu Gly Ser
35 40 45

Ala Leu Ala Leu Ala Arg Ala Pro Ala Ala Cys Leu Asn Phe Asn Cys
50 55 60

Met Leu Ile Leu Leu Pro Val Cys Arg Asn Leu Leu Ser Phe Leu Arg
65 70 75 80

Gly Ser Ser Ala Cys Cys Ser Thr Arg Val Arg Arg Gln Leu Asp Arg
85 90 95

Asn Leu Thr Phe His Lys Met Val Ala Trp Met Ile Ala Leu His Ser
100 105 110

Ala Ile His Thr Ile Ala His Leu Phe Asn Val Glu Trp Cys Val Asn
115 120 125

Ala Arg Val Asn Asn Ser Asp Pro Tyr Ser Val Ala Leu Ser Glu Leu
130 135 140

Gly Asp Arg Gln Asn Glu Ser Tyr Leu Asn Phe Ala Arg Lys Arg Ile
145 150 155 160

Lys Asn Pro Glu Gly Gly Leu Tyr Leu Ala Val Thr Leu Leu Ala Gly
165 170 175

Ile Thr Gly Val Val Ile Thr Leu Cys Leu Ile Leu Ile Ile Thr Ser
180 185 190

Ser Thr Lys Thr Ile Arg Arg Ser Tyr Phe Glu Val Phe Trp Tyr Thr
195 200 205

His His Leu Phe Val Ile Phe Phe Ile Gly Leu Ala Ile His Gly Ala
210 215 220

Glu Arg Ile Val Arg Gly Gln Thr Ala Glu Ser Leu Ala Val His Asn
225 230 235 240

Ile Thr Val Cys Glu Gln Lys Ile Ser Glu Trp Gly Lys Ile Lys Glu
245 250 255

Cys Pro Ile Pro Gln Phe Ala Gly Asn Pro Pro Met Thr Trp Lys Trp
260 265 270

Ile Val Gly Pro Met Phe Leu Tyr Leu Cys Glu Arg Leu Val Arg Phe
275 280 285

Trp Arg Ser Gln Gln Lys Val Val Ile Thr Lys Val Val Thr His Pro
290 295 300

Phe Lys Thr Ile Glu Leu Gln Met Lys Lys Lys Gly Phe Lys Met Glu

-continued

```
305                 310                 315                 320

Val Gly Gln Tyr Ile Phe Val Lys Cys Pro Lys Val Ser Lys Leu Glu
                325                 330                 335

Trp His Pro Phe Thr Leu Thr Ser Ala Pro Glu Glu Asp Phe Phe Ser
            340                 345                 350

Ile His Ile Arg Ile Val Gly Asp Trp Thr Glu Gly Leu Phe Asn Ala
        355                 360                 365

Cys Gly Cys Asp Lys Gln Glu Phe Gln Asp Ala Trp Lys Leu Pro Lys
    370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asn Asn Ala Thr
            420                 425                 430

Asn Leu Lys Leu Lys Lys Ile Tyr Phe Tyr Trp Leu Cys Arg Asp Thr
        435                 440                 445

His Ala Phe Glu Trp Phe Ala Asp Leu Leu Gln Leu Leu Glu Ser Gln
    450                 455                 460

Met Gln Glu Arg Asn Asn Ala Gly Phe Leu Ser Tyr Asn Ile Tyr Leu
465                 470                 475                 480

Thr Gly Trp Asp Glu Ser Gln Ala Asn His Phe Ala Val His His Asp
                485                 490                 495

Glu Glu Lys Asp Val Ile Thr Gly Leu Lys Gln Lys Thr Leu Tyr Gly
            500                 505                 510

Arg Pro Asn Trp Asp Asn Glu Phe Lys Thr Ile Ala Ser Gln His Pro
        515                 520                 525

Asn Thr Arg Ile Gly Val Phe Leu Cys Gly Pro Glu Ala Leu Ala Glu
    530                 535                 540

Thr Leu Ser Lys Gln Ser Ile Ser Asn Ser Glu Ser Gly Pro Arg Gly
545                 550                 555                 560

Val His Phe Ile Phe Asn Lys Glu Asn Phe
                565                 570


<210> SEQ ID NO 14
<211> LENGTH: 1713
<212> TYPE: DNA
<213> ORGANISM: Homo sapiens

<400> SEQUENCE: 14

atggggaact gggctgtgaa tgaggggctc tccatttttg tcattctggt ttggctgggg      60

ttgaacgtct tcctctttgt ctggtattac cgggtttatg atattccacc taagttcttt     120

tacacaagaa aacttcttgg gtcagcactg gcactggcca gggcccctgc agcctgcctg     180

aatttcaact gcatgctgat tctcttgcca gtctgtcgaa atctgctgtc cttcctcagg     240

ggttccagtg cgtgctgctc aacaagagtt cgaagacaac tggacaggaa tctcaccttt     300

cataaaatgg tggcatggat gattgcactt cactctgcga ttcacaccat tgcacatcta     360

tttaatgtgg aatggtgtgt gaatgcccga gtcaataatt ctgatcctta ttcagtagca     420

ctctctgaac ttggagacag gcaaaatgaa agttatctca attttgctcg aaagagaata     480

aagaaccctg aaggaggcct gtacctggct gtgaccctgt tggcaggcat cactggagtt     540

gtcatcacgc tgtgcctcat attaattatc acttcctcca ccaaaaccat ccggaggtct     600

tactttgaag tcttttggta cacacatcat ctctttgtga tcttcttcat tggccttgcc     660
```

```
atccatggag ctgaacgaat tgtacgtggg cagaccgcag agagtttggc tgtgcataat    720

ataacagttt gtgaacaaaa aatctcagaa tggggaaaaa taaaggaatg cccaatccct    780

cagtttgctg gaaaccctcc tatgacttgg aaatggatag tgggtcccat gtttctgtat    840

ctctgtgaga ggttggtgcg gttttggcga tctcaacaga aggtggtcat caccaaggtg    900

gtcactcacc ctttcaaaac catcgagcta cagatgaaga agaaggggtt caaaatggaa    960

gtgggacaat acatttttgt caagtgccca aaggtgtcca agctggagtg gcaccctttt   1020

acactgacat ccgcccctga ggaagacttc tttagtatcc atatccgcat cgttggggac   1080

tggacagagg ggctgttcaa tgcttgtggc tgtgataagc aggagtttca agatgcgtgg   1140

aaactaccta agatagcggt tgatgggccc tttggcactg ccagtgaaga tgtgttcagc   1200

tatgaggtgg tgatgttagt gggagcaggg attggggtca caccccttcgc atccattctc   1260

aagtcagtct ggtacaaata ttgcaataac gccaccaatc tgaagctcaa aaagatctac   1320

ttctactggc tgtgccggga cacacatgcc tttgagtggt ttgcagatct gctgcaactg   1380

ctggagagcc agatgcagga aaggaacaat gccggcttcc tcagctacaa catctacctc   1440

actggctggg atgagtctca ggccaatcac tttgctgtgc accatgatga ggagaaagat   1500

gtgatcacag gcctgaaaca aaagactttg tatggacggc ccaactggga taatgaattc   1560

aagacaattg caagtcaaca ccctaatacc agaataggag ttttcctctg tggacctgaa   1620

gccttggctg aaaccctgag taaacaaagc atctccaact ctgagtctgg ccctcgggga   1680

gtgcatttca ttttcaacaa ggaaaacttc taa                                1713
```

<210> SEQ ID NO 15
<211> LENGTH: 2025
<212> TYPE: DNA
<213> ORGANISM: Homo sapiens

<400> SEQUENCE: 15

```
gcaacctcca ccttccggtt tcaagcgatt ctcctgcctc agcctcccaa gtagttggga     60

ttacaggcac ccgccaccac gcctggctaa tttttatatt tttagtaaag acagggtttc    120

accattttgg ccaggctggt cttgaacccc tgatctcgtg atccacccac gttggcctcc    180

caaagtgctg gaattacagg cgtgagccac catgcctggc ccacattaca ttcttactca    240

cctcccccta ccatggaatt ttattccaca gatatgctat tggtttagct actatatgta    300

tatctgtgtt ttatacataa agcacaagaa ccttccagaa ccaattttcg ccaccttgga    360

agtaatacca cctctactaa gaatgcacag catagaccat aaaacctcaa tgctaagttc    420

aaatattggc cctaccacac atgagctgtg tggtcttgta caagttacat aacttctcct    480

ccttgtctca aactcctcac atataagatg aggataataa tagtacctgc ggccacacac    540

agtggcttaa acgtgtaatc ccagcacttt gggaggctgc ggcagaagga tcactcaaac    600

tcaggagttc aagagcagcc tgggtacatg gcgaaactct gtctctacaa aaaatacaaa    660

aattagctgg gtgtggtgat gtgtgcctgt agttccagct acttgggagg ctgaggtgag    720

aggatcgttc gagcccagga gatcaaggat gcagtgagct atgatcatgt ggctgcactc    780

cagcctggat aacagagcca gaccctgtct gaaagaaaca aaaacaaaaa cattagcacc    840

tgcatcatag ggtcactggg ggcactacat gagttcatgt acatcgagga cttaggacat    900

tgcctcaggc agacctagtg ctgcacaatt gcttatgtaa ttattcccaa atttctccag    960

ggcccacaga agaacatgga agtatcttgg tttggcaatt aaggtgaatc acattctcac   1020
```

-continued

```
tctccttttc tgcatctcta ccccacattc ccacaaagct ttattcacac caagtctcca   1080

gtccttgcct gcattgtgtg atgggtgcct gcagtgatgg gtggggacac ccatcactgt   1140

ccagggcgtc cccaccatcc tcacagcctc tctgtctggc ctcctgcctt tgagccagcc   1200

caccacactc tcatttctct gcccagcaga aaccaaactg tcctctgcat ttactgtctc   1260

aactggaaga gaaatgcaga atgacaaaga acttgtgaac aagggtcagc tccaacagag   1320

agtgaagcca aaggggctgg gcagaaagag agatgaagac gggggtctga ggaataaggc   1380

tgtaccagag tgagagtacg gggagggggt tgaacaagag ttcagggagg agagaattcc   1440

cagcgctgag ccagagactc ctttacagag gcccaaggag gcgtggaggg agggggaagg   1500

ctgccaaggc tctttctgtc tccatgagtg tgtcaagaat gcaaagcact aatgctcttc   1560

acttggtcca tcttgcaggg ttgagtttgc agtgagcaac cttgaaggat gagctgacat   1620

ctcgctcagg gccaaataac cgacttgctt actgcttgct ataaaatggc acgttaccca   1680

aggtcagagt tcccttccta taacctcccc atccctcaca cattcacagg tatctatcca   1740

agccatggca tcactctgtg gggcttgggg gcaaggcaac tgacactgca cgctggttct   1800

catgcttgcc aagcatgaag ccctgtgctg ctagcagctg tggaacatag ccgttagctt   1860

taaaagaggg taaaatcacg tcctggacag gacagccagg tgagttggga agggaagaga   1920

gcctgccacg ggcacaggca tgttggggga agtggaagtg gtgagagcac agtaggaagt   1980

gagaaggggc gggccgtgct taccaggccg tggacttaaa ccagg                  2025
```

<210> SEQ ID NO 16
<211> LENGTH: 635
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
tgcatcaccg cgttgcggcc tcatcagtcc cacgactttg tgcccatttt actcatgagg     60

agatggaggc ccagagagcc agtcagaaag tggctgggcc aggactaaga gtgcagcgcg    120

ctgcctccgt gccctgcgtc aacagctcaa ggaactgggg tgctccggaa atggggccaa    180

ggctgctggg cagcaggacg ctcagggcct tggcctcagg agagcaaatt ccccactcgg    240

agatcggtct tgttgctgca ttttattcat gggaaatctg aggctagaag agacgacaaa    300

cgacacgccg ttggacacac ggcaacgttt tagatgttgg gtctggccgg gcggccgtca    360

ccggtcacca tggggaggag gaggagccga gagacttgct cgcggccggg gggaggcaga    420

agcgcgtccc gcgggagagg tggctttgag gagtgagctc ccggtcccgc ggggacgcga    480

gtgggcccag tgcccgggct gccaggcggg gcggggcggg gccgggcgac tgagaggggc    540

ggggcctggc ggctgggagg ggcggggcgg atgcggggac agcggcctgg ctaactcctg    600

cacggcagtg cccttcccgg agcgtgccct cgccg                              635
```

<210> SEQ ID NO 17
<211> LENGTH: 1205
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
ctgcacagtg aggacgggac gcggaggggg cagcgggaac acgccgcccg catggctgcg     60
```

-continued

```
acagttggca gcgccgcggg acagagggaa actgaggccg gagccgcaga ctggacaccc    120

gagggggcga cccggggcag cacttggggc tcggctacgc gcacaggggg cggcgggcag    180

cagagtctgg gcctccgcgg ccggggttcc accgccggcc gcctccggct cgcgcaacgg    240

gagggaaaac ttggacaacc ctgccacgcc cagcccttgg ccgcgtggct tctcctgctc    300

gaagcgcggt cccaggagtg gccgacgctc cctctcctgc ccattccgcg gatgggcaat    360

cccaggcgga actcccttga gggtctcaga atatctggga gacctcgggc tcttgatctc    420

cgagacaccc cgtttcgtag tggagaacag tccagatcgg ggaagtttat tttgcccaaa    480

gccgcataga ggcccccctgg ccctcgattc cctctgcggg gctcagcagc gttgcagcct    540

agacgggtct tactgtgagc cgagcagcct ctgggaccac agaccttccc ctaccccaac    600

gttagaagcc ggagcccagc aaggagaagc gcgcacctcc tgctgtgaac gcgcacgacg    660

ccagggcagc tgccagaggc catggcctgg cgtgggcctg gagcccctct ggccagcctg    720

cacggggcca gggctacggg ataccagcag cgtgccctgg gctggatggc aggagagaca    780

ggacttgagg ctgtcccaga atgggctcag gcagggcgag gatatcaggg gaggtggtgt    840

acaggaagca gccgcccagc ttgcctggca cacagcaagc cctgcccatg aaggcctact    900

gccagaacag tgggcgaggc ccggcgtctc tgtggagtcg gtggggcccg ggacagggca    960

gcctgaggca ggtttccact ggcggtgaaa ggggccgtgt ggcaaggaca ggagagccag   1020

cctcagccca gcaggggaag gcggccccctg agtctccacc tggctgctgg cagccccact   1080

cggagcatcg gcgaaactga ggcttgccaa agaagccttt gtccagagtc acgcagctgg   1140

cgcggtggag ccagggccag aacccgtgca ggctgatccc agcctgcctt ctccactgtg   1200

ccccg                                                               1205
```

<210> SEQ ID NO 18
<211> LENGTH: 1843
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18

```
gagtgcatca ccgcgttgcg gcctcatcag tcccacgact ttgtgcccat tttactcatg     60

aggagatgga ggcccagaga gccagtcaga aagtggctgg gccaggacta agagtgcagc    120

gcgctgcctc cgtgccctgc gtcaacagct caaggaactg gggtgctccg gaaatggggc    180

caaggctgct gggcagcagg acgctcaggg ccttggcctc aggagagcaa attccccact    240

cggagatcgg tcttgttgct gcattttatt catgggaaat ctgaggctag aagagacgac    300

aaacgacacg ccgttggaca cacggcaacg ttttagatgt tgggtctggc cgggcggccg    360

tcaccggtca ccatggggag gaggaggagc cgagagactt gctcgcggcc gggggggaggc    420

agaagcgcgt cccgcgggag aggtggcttt gaggagtgag ctcccggtcc cgcggggacg    480

cgagtgggcc cagtgcccgg gctgccaggc ggggcggggc ggggccgggc gactgagagg    540

ggcggggcct ggcggctggg aggggcgggg cggatgcggg gacagcggcc tggctaactc    600

ctgcacggca gtgcccttcc cggagcgtgc cctcgccgct gcacagtgag gacgggacgc    660

ggagggggca gcgggaacac gccgcccgca tggctgcgac agttggcagc gccgcgggac    720

agagggaaac tgaggccgga gccgcagact ggacacccga gggggcgacc cggggcagca    780

cttggggctc ggctacgcgc acagggggcg gcgggcagca gagtctgggc ctccgcggcc    840
```

```
ggggttccac cgccggccgc ctccggctcg cgcaacggga gggaaaactt ggacaaccct    900
gccacgccca gcccttggcc gcgtggcttc tcctgctcga agcgcggtcc caggagtggc    960
cgacgctccc tctcctgccc attccgcgga tgggcaatcc caggcggaac tcccttgagg   1020
gtctcagaat atctgggaga cctcgggctc ttgatctccg agacaccccg tttcgtagtg   1080
gagaacagtc cagatcgggg aagtttattt tgcccaaagc cgcatagagg ccccctggcc   1140
ctcgattccc tctgcggggc tcagcagcgt tgcagcctag acgggtctta ctgtgagccg   1200
agcagcctct gggaccacag accttcccct accccaacgt tagaagccgg agcccagcaa   1260
ggagaagcgc gcacctcctg ctgtgaacgc gcacgacgcc agggcagctg ccagaggcca   1320
tggcctggcg tgggcctgga gcccctctgg ccagcctgca cggggccagg gctacgggat   1380
accagcagcg tgccctgggc tggatggcag gagagacagg acttgaggct gtcccagaat   1440
gggctcaggc agggcgagga tatcagggga ggtggtgtac aggaagcagc cgcccagctt   1500
gcctggcaca cagcaagccc tgcccatgaa ggcctactgc cagaacagtg ggcgaggccc   1560
ggcgtctctg tggagtcggt ggggcccggg acagggcagc ctgaggcagg tttccactgg   1620
cggtgaaagg ggccgtgtgg caaggacagg agagccagcc tcagcccagc aggggaaggc   1680
ggcccctgag tctccacctg gctgctggca gccccactcg gagcatcggc gaaactgagg   1740
cttgccaaag aagcctttgt ccagagtcac gcagctggcg cggtggagcc agggccagaa   1800
cccgtgcagg ctgatcccag cctgccttct ccactgtgcc ccg                     1843
```

```
<210> SEQ ID NO 19
<211> LENGTH: 1846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
```

```
ctgcacagtg aggacgggac gcggaggggg cagcgggaac acgccgcccg catggctgcg     60
acagttggca gcgccgcggg acagagggaa actgaggccg gagccgcaga ctggacaccc    120
gagggggcga cccggggcag cacttggggc tcggctacgc gcacaggggg cggcgggcag    180
cagagtctgg gcctccgcgg ccggggttcc accgccggcc gcctccggct cgcgcaacgg    240
gagggaaaac ttggacaacc ctgccacgcc cagcccttgg ccgcgtggct tctcctgctc    300
gaagcgcggt cccaggagtg gccgacgctc cctctcctgc ccattccgcg gatgggcaat    360
cccaggcgga actcccttga gggtctcaga atatctggga gacctcgggc tcttgatctc    420
cgagacaccc cgtttcgtag tggagaacag tccagatcgg ggaagtttat tttgcccaaa    480
gccgcataga ggccccctgg ccctcgattc cctctgcggg gctcagcagc gttgcagcct    540
agacgggtct tactgtgagc cgagcagcct ctgggaccac agaccttccc ctaccccaac    600
gttagaagcc ggagcccagc aaggagaagc gcgcacctcc tgctgtgaac gcgcacgacg    660
ccagggcagc tgccagaggc catggcctgg cgtgggcctg gagcccctct ggccagcctg    720
cacggggcca gggctacggg ataccagcag cgtgccctgg gctggatggc aggagagaca    780
ggacttgagg ctgtcccaga atgggctcag gcagggcgag gatatcaggg gaggtggtgt    840
acaggaagca gccgcccagc ttgcctggca cacagcaagc cctgcccatg aaggcctact    900
gccagaacag tgggcgaggc ccggcgtctc tgtggagtcg gtggggcccg ggacagggca    960
gcctgaggca ggtttccact ggcggtgaaa ggggccgtgt ggcaaggaca ggagagccag   1020
```

-continued cctcagccca gcaggggaag gcggcccctg agtctccacc tggctgctgg cagccccact 1080
cggagcatcg gcgaaactga ggcttgccaa agaagccttt gtccagagtc acgcagctgg 1140
cgcggtggag ccagggccag aacccgtgca ggctgatccc agcctgcctt ctccactgtg 1200
ccccgtgcat caccgcgttg cggcctcatc agtcccacga ctttgtgccc attttactca 1260
tgaggagatg gaggcccaga gagccagtca gaaagtggct gggccaggac taagagtgca 1320
gcgcgctgcc tccgtgccct gcgtcaacag ctcaaggaac tggggtgctc cggaaatggg 1380
gccaaggctg ctgggcagca ggacgctcag ggccttggcc tcaggagagc aaattcccca 1440
ctcggagatc ggtcttgttg ctgcatttta ttcatgggaa atctgaggct agaagagacg 1500
acaaacgaca cgccgttgga cacacggcaa cgttttagat gttgggtctg gccgggcggc 1560
cgtcaccggt caccatgggg aggaggagga gccgagagac ttgctcgcgg ccggggggag 1620
gcagaagcgc gtcccgcggg agaggtggct ttgaggagtg agctcccggt cccgcgggga 1680
cgcgagtggg cccagtgccc gggctgccag gcggggcggg gcggggccgg gcgactgaga 1740
ggggcggggc ctggcggctg ggaggggcgg ggcggatgcg gggacagcgg cctggctaac 1800
tcctgcacgg cagtgccctt cccggagcgt gccctcgccg ggatcc 1846

<210> SEQ ID NO 20
<211> LENGTH: 1591
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
taggtggctt cacccctctg cctgagcctg agtcctgtcc ctgccaagac tccgcccagc 60
cgacgcccac cccagctttc cctggactca tccctcagca gatatctgga tcctgcctag 120
cctggctcag catgactcat catgcagggt accgcccctg cccacctgtt ccccaatacc 180
gcaattcagg agctgggcag ttccccagag gccctaggaa actccccgcc cccgaccagg 240
ctttctccac tcctcccatc tgaccgcctg ttttctacgc ctcacgaccc tctgagcccc 300
ttggcgcact ccgacataac cacagccagg cctgagaagc cgccagcctc cgcagcgagt 360
gtgagcacgg gactcagaac tggcttctgc acagtgagga cgggacgcgg agggggcagc 420
gggaacacgc cgcccgcatg gctgcgacag ttggcagcgc cgcgggacag agggaaactg 480
aggccggagc cgcagactgg acacccgagg gggcgacccg gggcagcact tggggctcgg 540
ctacgcgcac agggggcggc gggcagcaga gtctgggcct ccgcggccgg ggttccaccg 600
ccggccgcct ccggctcgcg caacgggagg gaaaacttgg acaaccctgc cacgcccagc 660
ccttggccgc gtggcttctc ctgctcgaag cgcggtccca ggagtggccg acgctccctc 720
tcctgcccat tccgcggatg ggcaatccca ggcggaactc ccttgagggt ctcagaatat 780
ctgggagacc tcgggctctt gatctccgag acaccccgtt tcgtagtgga gaacagtcca 840
gatcggggaa gtttattttg cccaaagccg catagaggcc ccctggccct cgattccctc 900
tgcggggctc agcagcgttg cagcctagac gggtcttact gtgagccgag cagcctctgg 960
gaccacagac cttcccctac cccaacgtta gaagccggag cccagcaagg agaagcgcgc 1020
acctcctgct gtgaacgcgc acgacgccag ggcagctgcc agaggccatg gcctggcgtg 1080
ggcctggagc ccctctggcc agcctgcacg gggccagggc tacgggatac cagcagcgtg 1140
ccctgggctg gatggcagga gagacaggac ttgaggctgt cccagaatgg gctcaggcag 1200

-continued

```
ggcgaggata tcaggggagg tggtgtacag gaagcagccg cccagcttgc ctggcacaca   1260

gcaagccctg cccatgaagg cctactgcca gaacagtggg cgaggcccgg cgtctctgtg   1320

gagtcggtgg ggcccgggac agggcagcct gaggcaggtt tccactggcg gtgaaagggg   1380

ccgtgtggca aggacaggag agccagcctc agcccagcag gggaaggcgg cccctgagtc   1440

tccacctggc tgctggcagc cccactcgga gcatcggcga aactgaggct tgccaaagaa   1500

gcctttgtcc agagtcacgc agctggcgcg gtggagccag ggccagaacc cgtgcaggct   1560

gatcccagcc tgccttctcc actgtgcccc g                                  1591


<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

ccattcggag gtcttactt                                                  19


<210> SEQ ID NO 22
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

taagcttgat atcgaattcc cccgggggat ctcacttccc cacagaagct cttggcctgg     60

cctcctgcag tgccacgctc cattcggagg tcttacttct ccatgtggta gagaagtaag    120

acctccgaat ggagtgcggc acatgcttac cagtcagtgc ggcacatgct taccagctct    180

aggccagggc agatgggata tgacgaatgg actgccagct ggatacaagg atgctcaccg    240

acgtcgacgc gtaagggcga attcccccgg gggatccact agttctagag cggccaattc    300

gtcgagggac ctaataactt cgtatagcat acattatacg aagttat                  347
```

COMPOSITIONS AND METHODS FOR TREATING AMYOTROPHIC LATERAL SCLEROSIS

CROSS-REFERENCE TO RELATED APPLICATIONS

This application is a continuation application, pursuant to 35 U.S.C. § 111(a) of PCT International Application No. PCT/US2020/053826, filed Oct. 1, 2020 designating the United States and published in English, which claims priority to and the benefit of U.S. Provisional Application No. 62/908,942, filed Oct. 1, 2019, the entire contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 11, 2020, is named 167705-017001_PCT_SL.txt and is 35,030 bytes in size.

BACKGROUND OF THE INVENTION

Amyotrophic lateral sclerosis (ALS), also known as motor neuron disease or Lou Gehrig's disease, is a progressive neurodegenerative disease affecting motor neurons. There is not effective treatment for ALS, and the average survival is two to four years from the onset of disease, with only 10% of patients surviving past ten years. Approximately five new ALS cases per 100,000 inhabitants are diagnosed each year in the United States with an onset of about 50 to 60 years of age. The disease is characterized by muscular weakness, twitching, and atrophy due to the progressive loss of motor neurons in the brain.

Neuronal death activates microglia, a phagocytic immune cell resident of the central nervous system. Microglial cells are sensitive to neuronal injury and disease and adopt an activated morphology in response to such conditions. Generally neuroprotective, these cells can contribute to a neurotoxic environment and exacerbate the progressive ALS phenotype when exposed to certain stimuli, such as neuroinflammation. Thus, strategies are needed to modulate microglial response to such stimuli. This disclosure is directed to this and other important needs.

SUMMARY OF THE INVENTION

As described below, the present invention features compositions and methods for treating ALS.

In one aspect, the invention features a short hairpin RNA molecule (shRNA) that targets a Nox2 polynucleotide, the shRNA comprising the following sequence (SEQ ID NO: 1):

```
                              ▼
5' C    CCUCCU         A                             CAU
    CUGG      GCA-GUGCC CGCUNNNNNNNNNNNNNNNNNNNNNNCUC   G
                                                         U
    GACC      CGU CACGG GUGANNNNNNNNNNNNNNNNNNNNNNGAG   G
3'UC    ---AUU   A     C                             AUG
```

In another aspect, the invention features an inhibitory nucleic acid molecule that targets a Nox2 polynucleotide, where the inhibitory nucleic acid molecule is an siRNA, antisense polynucleotide, or shRNA.

In another aspect, the invention features a method of reducing a pro-inflammatory response in a cell, the method involving contacting the cell with an shRNA targeting Nox2 or a polynucleotide encoding the shRNA, thereby reducing pro-inflammatory response.

In another aspect, the invention features a method of reducing a pro-inflammatory response in a cell in response to immune stimulation, the method involving contacting the cell with an miRNA sponge that binds mir155 or a polynucleotide encoding the sponge, thereby reducing the pro-inflammatory response in the cell.

In another aspect, the invention features a method of reducing a pro-inflammatory response in a cell, the method involving contacting the cell with an shRNA targeting Nox2 or a polynucleotide encoding the shRNA and an miRNA sponge that binds mir155 or a polynucleotide encoding the sponge, thereby reducing pro-inflammatory response.

In another aspect, the invention features an expression vector or expression cassette comprising a polynucleotide encoding the shRNA of any of the above aspects, or the inhibitory nucleic acid molecule of any of the above aspects.

In various embodiments, the expression vector or expression cassette further contains an miRNA sponge that binds mir-155, where the sponge contains two or more miR-155 target sequences that bind miR-155. In some embodiments, the vector contains a 3' UTR containing 25 complementary binding sites recognizing the murine miR-155.

In some embodiments, the vector encodes an inhibitory nucleic acid molecule that targets a Nox2 polynucleotide and a polynucleotide that encodes a metallothionein; an miRNA sponge that binds mir-155 and a polynucleotide encoding a metallothionein; or an inhibitory nucleic acid molecule that targets a Nox2 polynucleotide, an miRNA sponge that binds mir-155, and a polynucleotide encoding a metallothionein. In some embodiments, the metallothionein is metallothionein 1G. In some embodiments, the vector is a lentiviral vector.

In some embodiments, the vector contains a promoter. In various embodiments, the promoter is the human phosphoglycerate kinase promoter. In some embodiments, the promoter is a microglia specific promoter. In some embodiments, the promoter is a TSPO, MHC class II, or CX3CR1 promoter.

In another aspect, the invention features a cell containing the shRNA of any of the above aspects, the inhibitory polynucleotide of any of the above aspects, or the expression vector of any of the above aspects.

In another aspect, the invention features a method of treating a subject having or having a propensity to develop amyotrophic lateral sclerosis (ALS), the method involving administering to the subject an effective amount of a composition containing a cell containing an shNox2 or a polynucleotide encoding the shNox2, thereby treating ALS.

In another aspect, the invention features a method of treating a subject having or having a propensity to develop amyotrophic lateral sclerosis (ALS), the method involving administering to the subject an effective amount of a composition containing a cell containing a miRNA sponge that binds mir155 or a polynucleotide encoding the sponge, thereby treating ALS.

In another aspect, the invention features a method of treating a subject having or having a propensity to develop amyotrophic lateral sclerosis (ALS), the method including administering to the subject an effective amount of a composition containing a cell containing an shRNA targeting Nox2 or a polynucleotide encoding the shRNA and an miRNA sponge that binds mir155 or a polynucleotide encoding the sponge, thereby treating ALS.

In any of the above aspects, the cell is a microglial cell or a precursor thereof or a hematopoietic stem progenitor cell (HSPC) or a cell descended therefrom. In any of the above aspects, the cell is a hematopoietic stem cell, hematopoietic stem progenitor cell (HSPC) or a cell descended therefrom. In some embodiments, the HSPC is $Lin^-$, $CD34^+$, $CD38^+$, and/or $CD90^+$. In any of the above aspects, the cell is hemizygous for the CX3CR1 gene. In any of the above embodiments, the cell is in vivo or in vitro. In any of the above aspects, the cell engrafts in the brain. In some embodiments, the engrafted cell is functionally equivalent to or expresses markers characteristic of a microglial progenitor cell. In any of the above aspects, the cell is an allogeneic or autologous cell.

In any of the above aspects, the cell is further contacted with a metallothionein or a polynucleotide encoding the metallothionein. In some embodiments, the metallothionein is metallothionein 1G. In any of the above aspects, the cell contains a metallothionein 1G polypeptide, or a fragment thereof or a nucleic acid molecule encoding the polypeptide.

In any of the above aspects, the method reduces reactive oxidative species in the cell. In any of the above aspects, the method reduces expression of one or more polypeptides selected from the group consisting of Iba1, Nox2, Arg-1, Mrc-1, Tnfa, IL-1b, Il-6 and Il-10 or a polynucleotide encoding the polypeptide. In any of the above aspects, the method reduces expression of a polypeptide selected from the group consisting of Bach1, Carhsp1, Cebpb, Csf1r, Inpp5d (Ship-1), Pea15a Olfml3 and Sall1, and Tnf alpha or a polynucleotide encoding the polypeptide.

In any of the above aspects the cell is present in a subject having or having a propensity to develop ALS. In any of the above aspects, the subject has early stage ALS. In any of the above aspects, the subject undergoes ablative conditioning prior to the method. In some embodiments, ablative conditioning involves administering to the subject an alkylating agent. In some embodiments, the alkylating agent is busulfan. In some embodiments, the conditioning involves administering a CSF-1R inhibitor. In some embodiments, the inhibitor is PLX3397, PLX5622, or liposomal clodronate. In any of the above aspects, the method reduces reactive oxygen species, delays the onset of ALS symptoms, reduces neuroinflammation, or extends life span.

In any of the above aspects, the administering is by intravenous, intracerebroventricular, or intra-thecal lumbar injection.

In any of the above aspects, the miRNA sponge contains the sequence identified in FIG. 2A (SEQ ID NOS 2-3).

In any of the above aspects, the shRNA further contains 5' and 3' flanking sequences derived from miR223.

The invention provides modified cells for the treatment of ALS and methods of delivering such cells to the brain. Compositions defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, “ablative conditioning” refers to administering to a subject a composition that destroys endogenous microglia.

By “agent” is meant any small molecule chemical compound, antibody, nucleic acid molecule, or polypeptide, or fragments thereof.

By “alteration” is meant a change (increase or decrease) in the expression levels or activity of a gene or polypeptide as detected by standard art known methods such as those described herein. As used herein, an alteration includes a 10% change in expression levels, a 25% change, a 40% change, and a 50% or greater change in expression levels.

By “ameliorate” is meant decrease, suppress, attenuate, diminish, arrest, or stabilize the development or progression of a disease.

By “biologic sample” is meant any tissue, cell, fluid, or other material derived from an organism. In this disclosure, “comprises,” “comprising,” “containing” and “having” and the like can have the meaning ascribed to them in U.S. Patent law and can mean “includes,” “including,” and the like; “consisting essentially of” or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the terms “determining”, “assessing”, “assaying”, “measuring” and “detecting” refer to both quantitative and qualitative determinations, and as such, the term “determining” is used interchangeably herein with “assaying,” “measuring,” and the like. Where a quantitative determination is intended, the phrase “determining an amount” of an analyte and the like is used. Where a qualitative and/or quantitative determination is intended, the phrase “determining a level” of an analyte or “detecting” an analyte is used.

“Detect” refers to identifying the presence, absence or amount of the analyte to be detected.

By “detectable label” is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include neurodegenerative diseases such as amyotrophic lateral sclerosis.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In particular embodiments, an effective amount is an amount that reduces neuroinflammation, increases muscle strength or function, or increases survival.

By "enhancer" is meant a polynucleotide that increases transcription of a gene of interest. In one embodiment, the enhancer comprises 50-1,500 nucleotides. Exemplary enhancers useful in the methods of the invention include, but are not limited to the following:

```
>MPP05A(hTSPO_upstream_enhancer)("E1.1")
                                          (SEQ ID NO: 4)
agactctgtctcaaaaaaaaaaaaaaaaaaaaaaaagagagagagaaaa
aggaagttagaaaaacagccctagaggccctacattctgagtaataggag
ttccagaaaggaagtgattgctgcacaacataaatttgaaaagaaagaga
agtgagaaaatagagggaaggaaatcaaagaaataatccaacttctgaaa
agtaaagaatgagcttccagcgggaaagtgcctgttgagtgcaggcacag
tggaggaaatgaagctgggtgtgttgccaggagttggaaacttgtctgag
caacatagcgcgaccctgtgtctacaaaaaaataaaaacaaaacaaaaaa
caaccaaagacttccgaaacagaatggctttagcctgctcaaccgcacac
tggcacctggccaacagcatctcttcatgattctgaaggacaacgatctg
cagctcagccaagcatcagccatctatggcctaggatgcaagaattcagc
aatgttaccttc
>MPP05B(hTSPO_upstream_enhancer)("E1.2")
                                          (SEQ ID NO: 5)
agactctgtctcaaaaaaaaaaaaaaaaaaaaaaaagagagagagaaaa
aggaagttagaaaaacagccctagaggccctacattctgagtaataggag
ttccagaaaggaagtgattgctgcacaacataaatttgaaaagaaagaga
agtgagaaaatagagggaaggaaatcaaagaaataatccaacttctgaaa
```

-continued

```
agtaaagaatgagcttccagcgggaaagtgcctgttgagtgcaggcacag
tggaggaaatgaagctgggtgtgttgccaggagttggaaacttgtctgag
caacatagcgcgaccctgtgtctacaaaaaaataaaaacaaaacaaaaaa
caaccaaagacttccgaaacagaatggctttagcctgctcaaccgcacac
tggcacctggccaacagcatctcttcatgattctgaaggacaacgatctg
cagctcagccaagcatcagccatctatggcctaggatgcaagaattcagc
aatgttaccttctgcatcaccgcgttgcggcctcatcagtcccacgactt
tgtgcccattttactcatgaggagatggaggcccagagagccagtcagaa
agtggctgggccaggactaagagtgcagcgcgctgcctccgtgccctgcg
tcaacagctcaaggaactggggtgctccggaaatggggccaaggctgctg
ggcagcaggacgctcagggccttggcctcaggagagcaaattccccactc
ggagatcggtcttgttgctgcattttattcatgggaaatctgaggctaga
agagacgacaaacgacacgccgttggacacacggcaacgttttagatgtt
gggtctggccgggcggccgtcaccggtcaccatggggaggaggaggagcc
gagagacttgctcgcggccgggggaggcagaagcgcgtcccgcgggaga
ggtggctttgaggagtgagctcccggtcccgcggggacgcgagtgggccc
agtgcccgggctgccaggcggggcggggcggggccgggcgactgagaggg
gcggggcctggcggctgggaggggCGGGGCGGATGCGGGGACAGCGGCCT
GGCTAACTCCTGCACGGCAGTGCCCTTCCCGGAGCGTGCCCTCGCCG
>MPP06(hTSPO_intronic_enhancer)("E2")
                                          (SEQ ID NO: 6)
Taggtggcttcacccctctgcctgagcctgagtcctgtccctgccaagac
tccgcccagccgacgcccaccccagctttccctggactcatccctcagca
gatatctggatcctgcctagcctggctcagcatgactcatcatgcagggt
accgcccctgcccacctgttccccaataccgcaattcaggagctgggcag
ttccccagaggccctaggaaactccccgcccccgaccaggctttctccac
tcctcccatctgaccgcctgttttctacgcctcacgaccctctgagcccc
ttggcgcactccgacataaccacagccaggcctgagaagccgccagcctc
cgcagcgagtgtgagcacgggactcagaactggctt
```

In various embodiments the enhancer is E1, which contains E1.1 and E1.2. In various embodiments the E1 enhancer comprises the sequences E1.1+E1.2 or E1.2+E1.1 in the indicated order from 5' to 3'.

Sequences comprising other regulatory elements useful in the methods of the invention follow:

```
>MPP03(hTSPO_upstream_enhancer_plus_upstream_and_intronic_prom)
                                                                              (SEQ ID NO: 7)
agactctgtctcaaaaaaaaaaaaaaaaaaaaaaaagagagagagaaaaaggaagttagaaaaacagccctagaggccctacattctgagt
aataggagttccagaaaggaagtgattgctgcacaacataaatttgaaaagaaagagaagtgagaaaatagagggaaggaaatcaaagaaata
atccaacttctgaaaagtaaagaatgagcttccagcgggaaagtgcctgttgagtgcaggcacagtggaggaaatgaagctgggtgtgttgcca
ggagttggaaacttgtctgagcaacatagcgcgaccctgtgtctacaaaaaaataaaaacaaaacaaaaaacaaccaaagacttccgaaacag
aatggctttagcctgctcaaccgcacactggcacctggccaacagcatctcttcatgattctgaaggacaacgatctgcagctcagccaagcatc
agccatctatggcctaggatgcaagaattcagcaatgttaccttcGAGtgcatcaccgcgttgcggcctcatcagtcccacgactttgtgcccat
tttactcatgaggagatggaggcccagagagccagtcagaaagtggctgggccaggactaagagtgcagcgcgctgcctccgtgccctgcgt
```

-continued caacagctcaaggaactggggtgctccggaaatggggccaaggctgctgggcagcaggacgctcagggccttggcctcaggagagcaaatt ccccactcggagatcggtcttgttgctgcattttattcatgggaaatctgaggctagaagagacgacaaacgacacgccgttggacacacggca acgttttagatgttgggtctggccgggcggccgtcaccggtcaccatggggaggaggaggagccgagagacttgctcgcggccgggggga ggcagaagcgcgtcccgcgggagaggtggctttgaggagtgagctcccggtcccgcggggacgcgagtgggcccagtgcccgggctgcc aggcggggcggggcggggccgggcgactgagaggggcggggcctggcggctgggaggggCGGGGCGGATGCGGGGA

CAGCGGCCTGGCTAACTCCTGCACGGCAGTGCCCTTCCCGGAGCGTGCCCTCGCCGCTG cacagtgaggacgggacgcggagggggcagcgggaacacgccgcccgcatggctgcgacagttggcagcgccgcgggacagagggaa actgaggccggagccgcagactggacacccgagggggcgacccggggcagcacttggggctcggctacgcgcacagggggcggcggg cagcagagtctgggcctccgcggccggggttccaccgccggccgcctccggctcgcgcaacgggagggaaaacttggacaaccctgccac gcccagcccttggccgcgtggcttctcctgctcgaagcgcggtcccaggagtggccgacgctccctctcctgcccattccgcggatgggcaat cccaggcggaactcccttgagggtctcagaatatctgggagacctcgggctcttgatctccgagacaccccgtttcgtagtggagaacagtcca gatcggggaagtttatttgcccaaagccgcatagaggccccctggccctcgattccctctgcggggctcagcagcgttgcagcctagacgggt cttactgtgagccgagcagcctctgggaccacagaccttcccctaccccaacgttagaagccggagcccagcaaggagaagcgcgcacctcc tgctgtgaacgcgcacgacgccagggcagctgccagaggccatggcctggcgtgggcctggagcccctctggccagcctgcacggggcca gggctacgggataccagcagcgtgccctgggctggatggcaggagagacaggacttgaggctgtcccagaatgggctcaggcagggcgag gatatcaggggaggtggtgtacaggaagcagccgcccagcttgcctggcacacagcaagccctgcccatgaaggcctactgccagaacagt gggcgaggcccggcgtctctgtggagtcggtggggcccgggacagggcagcctgaggcaggtttccactggcggtgaaaggggccgtgtg gcaaggacaggagagccagcctcagcccagcaggggaaggcggcccctgagtctccacctggctgctggcagccccactcggagcatcg gcgaaactgaggcttgccaaagaagcctttgtccagagtcacgcagctggcgcggtggagccagggccagaacccgtgcaggctgatccca gcctgccttctccactgtgccccg >MPP06-01(hTSPO_prximal5'prom_plus_proximal_upstream_promoter)

(SEQ ID NO: 8)

Taggtggcttcacccctctgcctgagcctgagtcctgtccctgccaagactccgcccagccgacgcccaccccagctttccctggactcatccc tcagcagatatctggatcctgcctagcctggctcagcatgactcatcatgcagggtaccgcccctgcccacctgttccccaataccgcaattcag gagctgggcagttccccagaggccctaggaaactccccgcccccgaccaggctttctccactcctcccatctgaccgcctgttttctacgcctca cgaccctctgagccccttggcgcactccgacataaccacagccaggcctgagaagccgccagcctccgcagcgagtgtgagcacgggactc agaactggctttgcatcaccgcgttgcggcctcatcagtcccacgactttgtgcccattttactcatgaggagatggaggcccagagagccagtc agaaagtggctgggccaggactaagagtgcagcgcgctgcctccgtgccctgcgtcaacagctcaaggaactggggtgctccggaaatggg gccaaggctgctgggcagcaggacgctcagggccttggcctcaggagagcaaattccccactcggagatcggtcttgttgctgcattttattcat gggaaatctgaggctagaagagacgacaaacgacacgccgttggacacacggcaacgttttagatgttgggtctggccgggcggccgtcacc ggtcaccatggggaggaggaggagccgagagacttgctcgcggccgggggggaggcagaagcgcgtcccgcgggagaggtggctttgag gagtgagctcccggtcccgcggggacgcgagtgggcccagtgcccgggctgccaggcggggcggggcggggccgggcgactgagagg ggcggggcctggcggctgggaggggCGGGGCGGATGCGGGGACAGCGGCCTGGCTAACTCCTGCAC

GGCAGTGCCCTTCCCGGAGCGTGCCCTCGCCG

>MPP03(hTSPO_upstream_plus_intronic_prom)

(SEQ ID NO: 9)

taggtggcttcacccctctgcctgagcctgagtcctgtccctgccaagactccgcccagccgacgcccaccccagctttccctggactcatccct cagcagatatctggatcctgcctagcctggctcagcatgactcatcatgcagggtaccgcccctgcccacctgttccccaataccgcaattcagg agctgggcagttccccagaggccctaggaaactccccgcccccgaccaggctttctccactcctcccatctgaccgcctgttttctacgcctcac gaccctctgagccccttggcgcactccgacataaccacagccaggcctgagaagccgccagcctccgcagcgagtgtgagcacgggactca gaactggcttGAGtgcatcaccgcgttgcggcctcatcagtcccacgactttgtgcccattttactcatgaggagatggaggcccagagagcc agtcagaaagtggctgggccaggactaagagtgcagcgcgctgcctccgtgccctgcgtcaacagctcaaggaactggggtgctccggaaat ggggccaaggctgctgggcagcaggacgctcagggccttggcctcaggagagcaaattccccactcggagatcggtcttgttgctgcattttat -continued

```
tcatgggaaatctgaggctagaagagacgacaaacgacacgccgttggacacacggcaacgttttagatgttgggtctggccgggcggccgt

caccggtcaccatggggaggaggaggagccgagagacttgctcgcggccggggggaggcagaagcgcgtcccgcgggagaggtggcttt

gaggagtgagctcccggtcccgcggggacgcgagtgggcccagtgcccgggctgccaggcggggcggggcggggccgggcgactgag

aggggcggggcctggcggctgggaggggCGGGGCGGATGCGGGGACAGCGGCCTGGCTAACTCCTGC

ACGGCAGTGCCCTTCCCGGAGCGTGCCCTCGCCGCTGcacagtgaggacgggacgcggagggggcagc

gggaacacgccgcccgcatggctgcgacagttggcagcgccgcgggacagagggaaactgaggccggagccgcagactggacacccga

gggggcgacccggggcagcacttggggctcggctacgcgcacagggggcggcgggcagcagagtctgggcctccgcggccggggttcc

accgccggccgcctccggctcgcgcaacgggagggaaaacttggacaaccctgccacgcccagcccttggccgcgtggcttctcctgctcg

aagcgcggtcccaggagtggccgacgctccctctcctgcccattccgcggatgggcaatcccaggcggaactcccttgagggtctcagaatat

ctgggagacctcgggctcttgatctccgagacaccccgtttcgtagtggagaacagtccagatcggggaagtttattttgcccaaagccgcatag

aggccccctggccctcgattccctctgcggggctcagcagcgttgcagcctagacgggtcttactgtgagccgagcagcctctgggaccacag

accttcccctaccccaacgttagaagccggagcccagcaaggagaagcgcgcacctcctgctgtgaacgcgcacgacgccagggcagctgc

cagaggccatggcctggcgtgggcctggagcccctctggccagcctgcacggggccagggctacgggataccagcagcgtgccctgggct

ggatggcaggagagacaggacttgaggctgtcccagaatgggctcaggcagggcgaggatatcaggggaggtggtgtacaggaagcagcc

gcccagcttgcctggcacacagcaagccctgcccatgaaggcctactgccagaacagtgggcgaggcccggcgtctctgtggagtcggtgg

ggcccgggacagggcagcctgaggcaggtttccactggcggtgaaaggggccgtgtggcaaggacaggagagccagcctcagcccagca

ggggaaggcggcccctgagtctccacctggctgctggcagccccactcggagcatcggcgaaactgaggcttgccaaagaagcctttgtcca

gagtcacgcagctggcgcggtggagccagggccagaacccgtgcaggctgatcccagcctgccttctccactgtgccccg
```

"Exogenous nucleic acid molecule," as used herein, refers to a nucleic acid molecule that is not an endogenous nucleic acid molecule, i.e., it is a nucleic acid molecule that does not naturally occur in a cell.

By "expression cassette" is meant those vector elements needed for expression of a gene. In one embodiment, an expression cassette comprises a promoter, a polynucleotide encoding a polypeptide of interest, and a terminator.

By "fragment" is meant a portion of a protein or nucleic acid that is substantially identical to a reference protein or nucleic acid. In some embodiments the portion retains at least 50%, 75%, or 80%, or more preferably 90%, 95%, or even 99% of the biological activity of the reference protein or nucleic acid described herein.

By "gene locus" is meant a position within a genome where a particular gene sequence is disposed.

By "hematopoietic stem cell (HSC)" is meant a stem cell that gives rise to a variety of blood cells.

By "hematopoietic stem progenitor cell (HSPC)" is meant a cell that gives rise to a hematopoietic stem cell.

Cells (e.g., HSCs, HSPCs) that may be used in conjunction with the compositions and methods described herein include CD34+/CD90+ cells, CD34+CD38− cells and CD34+/CD164+ cells. These cells may contain a higher percentage of HSCs or HSPCs. These cells are described in WO2015/059674, WO2017/218948, Radtke et al. Sci. Transl. Med. 9:1-10, 2017, Radtke et al. Mol Ther Methods Clin Dev. 18:679-691, 2020, and Pellin et al. Nat. Comm. 10:2395, 2019, the disclosures of each of which are hereby incorporated by reference in their entirety".

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "metallothionein 1G (MT1G) polypeptide" is meant a protein having at least about 85% amino acid sequence identity to UniProt Accession No. P13640-1 or a fragment thereof and having heavy metal binding activity. An exemplary MT1G polypeptide sequence is provided below.

>sp|P13640|MT1G_HUMAN Metallothionein-1G OS = *Homo sapiens* OX = 9606 GN = MT1G PE = 1 SV = 2

(SEQ ID NO: 10)

MDPNCSCAAAGVSCTCASSCKCKECKCTSCKKSCCSCCPVGCAKCAQGCI

CKGASEKCSCCA

By "metallothionein 1G (MT1G) polynucleotide" is meant a nucleic acid molecule encoding an MT1G polypeptide. The MT1G gene encodes a protein that binds heavy metals. An exemplary MT1G polynucleotide sequence is provided below:

>NM_005950.2 *Homo sapiens* metallothionein 1G (MT1G), transcript variant 1, mRNA (SEQ ID NO: 11)

ACTCCGCCTTCCACGTGCACCCACTGCCTCTTCCCTTCTCGCTTGGGAAC

TCTAGTCTCGCCTCGGGTTGCAATGGACCCCAACTGCTCCTGTGCCGCTG

GTGTCTCCTGCACCTGCGCCAGCTCCTGCAAGTGCAAAGAGTGCAAATGC

ACCTCCTGCAAGAAGAGCTGCTGCTCCTGCTGCCCTGTGGGCTGTGCCAA

GTGTGCCCAGGGCTGCATCTGCAAAGGGGCATCGGAGAAGTGCAGCTGCT

GCGCCTGATGTCGGGACAGCCCTGCTCCCAAGTACAAATAGAGTGACCCG

TAAAATCCAGGATTTTTTGTTTTTTGCTACAATCTTGACCCCTTTGCTAC

ATTCCTTTTTTTCTGTGAAATATGTGAATAATAATTAAACACTTAGACTT

GAAAAAAAAAAAAAAAAAAA

By "microglia" is meant an immune cell of the central nervous system.

By "microRNA" is meant a small non-coding RNA molecule involved in RNA silencing and/or post-transcriptional regulation of gene expression. miRNAs base-pair with complementary sequences in mRNA molecules and impair translation by facilitating deadenylation of the poly-A tail of the mRNA, cleavage of the mRNA molecule, and translational repression due to inefficient binding of the mRNA: miRNA hybrid by the ribosome.

By "microRNA 155 (miR155) polynucleotide" is meant a nucleic acid molecule having the polynucleotide sequence is provided below.

>NR_030784.1 *Homo sapiens* microRNA 155 (MIR155), microRNA (SEQ ID NO: 12)

CTGTTAATGCTAATCGTGATAGGGGTTTTTGCCTCCAACTGACTCCTACA

TATTAGCATTAACAG

By "nanoparticle" is meant a composite structure of nanoscale dimensions. In particular, nanoparticles are typically particles of a size in the range of from about 1 to about 1000 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in several therapeutic applications typically have a size of about 200 nm or below, and the ones used, in particular, for delivery associated with therapeutic agents typically have a diameter from about 1 to about 100 nm.

By "NADPH Oxidase 2 (Nox2) polypeptide" is meant a protein having at least about 85% amino acid sequence identity to UniProt Accession No. P04839 or a fragment thereof and having immunomodulatory activity. An exemplary Nox2 polypeptide sequence is provided below.

>sp|P04839|CY24B_HUMAN Cytochrome b-245 heavy chain OS = *Homo sapiens* OX = 9606 GN = CYBB PE = 1 SV = 2

(SEQ ID NO: 13)

MGNWAVNEGLSIFVILVWLGLNVFLFVWYYRVYDIPPKFFYTRKLLGSAL

ALARAPAACLNFNCMLILLPVCRNLLSFLRGSSACCSTRVRRQLDRNLTF

HKMVAWMIALHSAIHTIAHLFNVEWCVNARVNNSDPYSVALSELGDRQNE

SYLNFARKRIKNPEGGLYLAVTLLAGITGVVITLCLILIITSSTKTIRRS

YFEVFWYTHHLFVIFFIGLAIHGAERIVRGQTAESLAVHNITVCEQKISE

WGKIKECPIPQFAGNPPMTWKWIVGPMFLYLCERLVRFWRSQQKVVITKV

VTHPFKTIELQMKKKGFKMEVGQYIFVKCPKVSKLEWHPFTLTSAPEEDF

FSIHIRIVGDWTEGLFNACGCDKQEFQDAWKLPKIAVDGPFGTASEDVFS

YEVVMLVGAGIGVTPFASILKSVWYKYCNNATNLKLKKIYFYWLCRDTHA

FEWFADLLQLLESQMQERNNAGFLSYNIYLTGWDESQANHFAVHHDEEKD

-continued

VITGLKQKTLYGRPNWDNEFKTIASQHPNTRIGVFLCGPEALAETLSKQS

ISNSESGPRGVHFIFNKENF

By "NADPH Oxidase 2 (Nox2) polynucleotide" is meant a nucleic acid molecule encoding a Nox2 polypeptide. The Nox2 gene encodes a protein that participates in the regulation of cellular pH. An exemplary Nox2 polynucleotide sequence is provided below.

>CYBB-201 cds: protein_coding (SEQ ID NO: 14)

ATGGGGAACTGGGCTGTGAATGAGGGGCTCTCCATTTTTGTCATTCTGGT

TTGGCTGGGGTTGAACGTCTTCCTCTTTGTCTGGTATTACCGGGTTTATG

ATATTCCACCTAAGTTCTTTTACACAAGAAAACTTCTTGGGTCAGCACTG

GCACTGGCCAGGGCCCCTGCAGCCTGCCTGAATTTCAACTGCATGCTGAT

TCTCTTGCCAGTCTGTCGAAATCTGCTGTCCTTCCTCAGGGGTTCCAGTG

CGTGCTGCTCAACAAGAGTTCGAAGACAACTGGACAGGAATCTCACCTTT

CATAAAATGGTGGCATGGATGATTGCACTTCACTCTGCGATTCACACCAT

TGCACATCTATTTAATGTGGAATGGTGTGTGAATGCCCGAGTCAATAATT

CTGATCCTTATTCAGTAGCACTCTCTGAACTTGGAGACAGGCAAAATGAA

AGTTATCTCAATTTTGCTCGAAAGAGAATAAAGAACCCTGAAGGAGGCCT

GTACCTGGCTGTGACCCTGTTGGCAGGCATCACTGGAGTTGTCATCACGC

TGTGCCTCATATTAATTATCACTTCCTCCACCAAAACCATCCGGAGGTCT

TACTTTGAAGTCTTTTGGTACACACATCATCTCTTTGTGATCTTCTTCAT

TGGCCTTGCCATCCATGGAGCTGAACGAATTGTACGTGGGCAGACCGCAG

AGAGTTTGGCTGTGCATAATATAACAGTTTGTGAACAAAAAATCTCAGAA

TGGGGAAAAATAAAGGAATGCCCAATCCCTCAGTTTGCTGGAAACCCTCC

TATGACTTGGAAATGGATAGTGGGTCCCATGTTTCTGTATCTCTGTGAGA

GGTTGGTGCGGTTTTGGCGATCTCAACAGAAGGTGGTCATCACCAAGGTG

GTCACTCACCCTTTCAAAACCATCGAGCTACAGATGAAGAAGAAGGGGTT

CAAAATGGAAGTGGGACAATACATTTTTGTCAAGTGCCCAAAGGTGTCCA

AGCTGGAGTGGCACCCTTTTACACTGACATCCGCCCCTGAGGAAGACTTC

TTTAGTATCCATATCCGCATCGTTGGGGACTGGACAGAGGGGCTGTTCAA

TGCTTGTGGCTGTGATAAGCAGGAGTTTCAAGATGCGTGGAAACTACCTA

AGATAGCGGTTGATGGGCCCTTTGGCACTGCCAGTGAAGATGTGTTCAGC

TATGAGGTGGTGATGTTAGTGGGAGCAGGGATTGGGGTCACACCCTTCGC

ATCCATTCTCAAGTCAGTCTGGTACAAATATTGCAATAACGCCACCAATC

TGAAGCTCAAAAAGATCTACTTCTACTGGCTGTGCCGGGACACACATGCC

TTTGAGTGGTTTGCAGATCTGCTGCAACTGCTGGAGAGCCAGATGCAGGA

AAGGAACAATGCCGGCTTCCTCAGCTACAACATCTACCTCACTGGCTGGG

ATGAGTCTCAGGCCAATCACTTTGCTGTGCACCATGATGAGGAGAAAGAT

GTGATCACAGGCCTGAAACAAAAGACTTTGTATGGACGGCCCAACTGGGA

TAATGAATTCAAGACAATTGCAAGTCAACACCCTAATACCAGAATAGGAG

TTTTCCTCTGTGGACCTGAAGCCTTGGCTGAAACCCTGAGTAAACAAAGC

-continued

ATCTCCAACTCTGAGTCTGGCCCTCGGGGAGTGCATTTCATTTTCAACAA

GGAAAACTTCTAA

As used herein "neurodegenerative disease" refers to any of a group of diseases characterized by the progressive loss of structure and/or function of neurons, including death of neurons. Exemplary neurodegenerative diseases include, without limitation, amyotrophic lateral sclerosis (ALS).

The term "nucleotide molecule", "polynucleotide", or "nucleic acid sequence" are used interchangeably to refer to a molecule comprising RNA or DNA. In various embodiments, the nucleotide molecule or polynucleotide comprises modified nucleotides (e.g., locked nucleic acids (LNA)). In some embodiments, the nucleotide molecule or polynucleotide comprises RNA and DNA. The sugar backbone of the nucleotide molecule is non-limiting and may comprise ribose, deoxyribose, or various other suitable sugars. In some embodiments, the nucleic acid molecule comprises at least two nucleotides covalently linked together. In some embodiments, the nucleic acid molecule of the present invention is single-stranded. In some embodiments, the nucleic acid molecule is double stranded. In some embodiments, the nucleic acid molecule is triple-stranded. In some embodiments, the nucleic acid molecule comprises phosphodiester bonds. In some embodiments, the nucleic acid molecule comprises a single-stranded or double-stranded deoxyribonucleic acid (DNA) or a single-stranded or double-stranded ribonucleic acid (RNA). In some embodiments, the nucleic acid molecule comprises a nucleic acid analog. In some embodiments, the nucleic acid analog has a backbone, comprising a bond other than and/or in addition to a phosphodiester bond, such as, by non-limiting example, phosphoramide, phosphorothioate, phosphorodithioate or O-methylphophoroamidite linkage. In some embodiments, the nucleic acid analog is selected from a nucleic acid analog with a backbone selected from a positive backbone; a non-ionic backbone and a non-ribose backbone. In some embodiments, the nucleic acid molecule contains one or more carbocyclic sugars. In some embodiments, the nucleic acid molecule comprises modifications of its ribose-phosphate backbone. In some embodiments, these modifications are performed to facilitate the addition of additional moieties, such as labels. In some embodiments, these modifications are performed to increase the stability and half-life of such molecules in physiological environments. In some embodiments, the term "polynucleotide" captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil,-uracil-5-oxyacetic acid methylester, uracil-5-oxyacetic acid, pseudouracil, queosine, 2-thiocytosine, and 2,6-diaminopurine.

As used herein, "obtaining" as in "obtaining an agent" includes synthesizing, purchasing, or otherwise acquiring the agent.

By "PLX3397" is meant a colony stimulating factor-1 receptor (CSF-1R) inhibitor having the structure

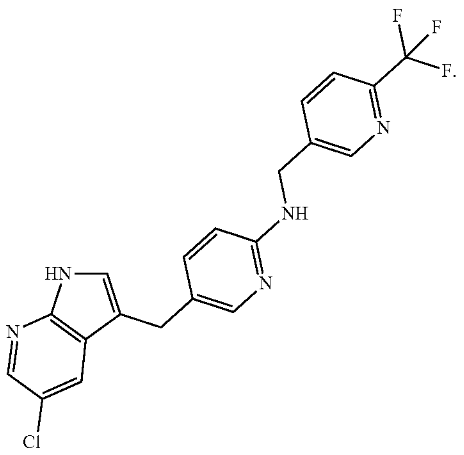 [SMILES: FC(F)(F)c1ccc(CNc2ccc(Cc3c[nH]c4ncc(Cl)cc34)cn2)cn1]

By "PLX5622" is meant a colony stimulating factor-1 receptor (CSF-1R) inhibitor having the structure

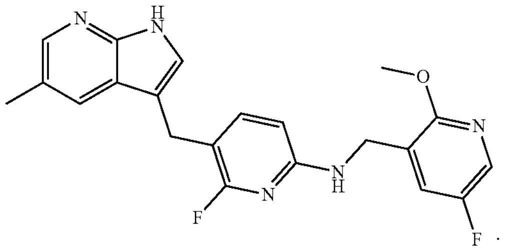 [SMILES: COc1ncc(F)cc1CNc1ccc(Cc2c[nH]c3ncc(C)cc23)c(F)n1]

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "promoter" is meant a polynucleotide sufficient to direct transcription. In some embodiments, the promoter is a translocator protein promoter (TSPO). In some embodiments, the promoter is a CX3CR1 promoter. In an exemplary embodiment, the CX3CR1 promoter comprises a sequence with at least 85% sequence identity to the sequence of GeneBank Accession number GQ258357.1 or a fragment thereof. The sequence of GeneBank Accession number GQ258357.1 is provided below.

```
GeneBank Accession number GQ258357.1:
                                        (SEQ ID NO: 15)
GCAACCTCCACCTTCCGGTTTCAAGCGATTCTCCTGCCTCAGCCTCCCAA

GTAGTTGGGATTACAGGCACCCGCCACCACGCCTGGCTAATTTTTATATT

TTTAGTAAAGACAGGGTTTCACCATTTTGGCCAGGCTGGTCTTGAACCCC

TGATCTCGTGATCCACCCACGTTGGCCTCCCAAAGTGCTGGAATTACAGG

CGTGAGCCACCATGCCTGGCCCACATTACATTCTTACTCACCTCCCCCTA
```

-continued

```
CCATGGAATTTTATTCCACAGATATGCTATTGGTTTAGCTACTATATGTA

TATCTGTGTTTTATACATAAAGCACAAGAACCTTCCAGAACCAATTTTCG

CCACCTTGGAAGTAATACCACCTCTACTAAGAATGCACAGCATAGACCAT

AAAACCTCAATGCTAAGTTCAAATATTGGCCCTACCACACATGAGCTGTG

TGGTCTTGTACAAGTTACATAACTTCTCCTCCTTGTCTCAAACTCCTCAC

ATATAAGATGAGGATAATAATAGTACCTGCGGCCACACACAGTGGCTTAA

ACGTGTAATCCCAGCACTTTGGGAGGCTGCGGCAGAAGGATCACTCAAAC

TCAGGAGTTCAAGAGCAGCCTGGGTACATGGCGAAACTCTGTCTCTACAA

AAAATACAAAAATTAGCTGGGTGTGGTGATGTGTGCCTGTAGTTCCAGCT

ACTTGGGAGGCTGAGGTGAGAGGATCGTTCGAGCCCAGGAGATCAAGGAT

GCAGTGAGCTATGATCATGTGGCTGCACTCCAGCCTGGATAACAGAGCCA

GACCCTGTCTGAAAGAAACAAAAACAAAAACATTAGCACCTGCATCATAG

GGTCACTGGGGGCACTACATGAGTTCATGTACATCGAGGACTTAGGACAT

TGCCTCAGGCAGACCTAGTGCTGCACAATTGCTTATGTAATTATTCCCAA

ATTTCTCCAGGGCCCACAGAAGAACATGGAAGTATCTTGGTTTGGCAATT

AAGGTGAATCACATTCTCACTCTCCTTTTCTGCATCTCTACCCCACATTC

CCACAAAGCTTTATTCACACCAAGTCTCCAGTCCTTGCCTGCATTGTGTG

ATGGGTGCCTGCAGTGATGGGTGGGGACACCCATCACTGTCCAGGGCGTC

CCCACCATCCTCACAGCCTCTCTGTCTGGCCTCCTGCCTTTGAGCCAGCC

CACCACACTCTCATTTCTCTGCCCAGCAGAAACCAAACTGTCCTCTGCAT

TTACTGTCTCAACTGGAAGAGAAATGCAGAATGACAAAGAACTTGTGAAC

AAGGGTCAGCTCCAACAGAGAGTGAAGCCAAAGGGGCTGGGCAGAAAGAG

AGATGAAGACGGGGGTCTGAGGAATAAGGCTGTACCAGAGTGAGAGTACG

GGGGAGGGGGTTGAACAAGAGTTCAGGGAGGAGAGAATTCCCAGCGCTGAG

CCAGAGACTCCTTTACAGAGGCCCAAGGAGGCGTGGAGGGAGGGGGAAGG

CTGCCAAGGCTCTTTCTGTCTCCATGAGTGTGTCAAGAATGCAAAGCACT

AATGCTCTTCACTTGGTCCATCTTGCAGGGTTGAGTTTGCAGTGAGCAAC

CTTGAAGGATGAGCTGACATCTCGCTCAGGGCCAAATAACCGACTTGCTT

ACTGCTTGCTATAAAATGGCACGTTACCCAAGGTCAGAGTTCCCTTCCTA

TAACCTCCCCATCCCTCACACATTCACAGGTATCTATCCAAGCCATGGCA

TCACTCTGTGGGGCTTGGGGGCAAGGCAACTGACACTGCACGCTGGTTCT

CATGCTTGCCAAGCATGAAGCCCTGTGCTGCTAGCAGCTGTGGAACATAG

CCGTTAGCTTTAAAAGAGGGTAAAATCACGTCCTGGACAGGACAGCCAGG

TGAGTTGGGAAGGGAAGAGAGCCTGCCACGGGCACAGGCATGTTGGGGGA

AGTGGAAGTGGTGAGAGCACAGTAGGAAGTGAGAAGGGGCGGGCCGTGCT

TACCAGGCCGTGGACTTAAACCAGG
```

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be, in some embodiments at least about 16 amino acids, at least about 20 amino acids, at least about 25 amino acids, or about 35 amino acids, about 50 amino acids, or about 100 amino acids, or any integer thereabout or therebetween. For nucleic acids, the length of the reference nucleic acid sequence will generally be at least about 50 nucleotides, at least about 60 nucleotides, at least about 75 nucleotides, at least about 100 nucleotides, or at least about 300 nucleotides, or any integer thereabout or therebetween.

By "short hairpin RNA (shRNA)" is meant an artificial RNA molecule having a tight hairpin turn and a nucleotide sequence complementary to a target polynucleotide molecule to be degraded or silenced. After expression, shRNAs are processed and loaded into the RNA-induced silencing complex. This complex, due to the complementary nucleotide sequence, reduces the activity or translation of the target polynucleotide.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or about 250 mM NaCl and 25 mM trisodium citrate. Low stringency hybridization can be obtained in the absence of organic solvent, e.g., formamide, while high stringency hybridization can be obtained in the presence of at least about 35% formamide, and in some embodiments, at least about 50% formamide. Stringent temperature conditions will ordinarily include temperatures of at least about 30° C. at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 μg/ml denatured salmon sperm DNA (ssDNA). In yet another embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will comprise less than about 30 mM NaCl and 3 mM trisodium citrate or less than about 15 mM NaCl and 1.5 mM trisodium citrate. Stringent temperature conditions for the wash steps will ordinarily include a temperature of at least about 25° C., at least about 42° C., or at least about 68° C. In some embodiments, wash steps will occur at 25° C. in 30 mM NaCl, 3 mM trisodium citrate, and 0.1% SDS. In other embodiments, wash steps will occur at 42 C in 15 mM NaCl, 1.5 mM trisodium citrate, and 0.1% SDS. In other embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In some embodiments, such a sequence is at least 60%, 80% or 85%, 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "translocator protein promoter" or "TSPO promoter" is meant a polynucleotide sufficient to direct expression of a transgene in a microglial cell. In one embodiment the TSPO promoter is responsive to inflammation. Exemplary promoters useful in the methods of the invention include, but are not limited to, the following:

>MPP01(hTSPO_prximal5'prom)("P1")

(SEQ ID NO: 16)

Tgcatcaccgcgttgcggcctcatcagtcccacgactttgtgcccatttt actcatgaggagatggaggcccagagagccagtcagaaagtggctgggcc aggactaagagtgcagcgcgctgcctccgtgccctgcgtcaacagctcaa ggaactggggtgctccggaaatggggccaaggctgctgggcagcaggacg ctcagggccttggcctcaggagagcaaattccccactcggagatcggtct tgttgctgcattttattcatgggaaatctgaggctagaagagacgacaaa cgacacgccgttggacacacggcaacgttttagatgttgggtctggccgg -continued gcggccgtcaccggtcaccatggggaggaggaggagccgagagacttgct cgcggccgggggggaggcagaagcgcgtcccgcgggagaggtggctttgag gagtgagctcccggtcccgcggggacgcgagtgggcccagtgcccgggct gccaggcggggcggggcggggccgggcgactgagaggggcggggcctggc ggctgggaggggCGGGGCGGATGCGGGGACAGCGGCCTGGCTAACTCCTG

CACGGCAGTGCCCTTCCCGGAGCGTGCCCTCGCCG

The P1 promoter comprises 635 bp that correspond to nucleotide residues-562 to +73 (capital letters) of the hTspo immediate 5' promoter. of the hTspo immediate 5' promoter.

>MPP02(hTSPO_intronic5'prom)("P2")

(SEQ ID NO: 17)

CTGcacagtgaggacgggacgcggagggggcagcgggaacacgccgcccgcatggctgcgacagttggcagcgccgcgggacagag ggaaactgaggccggagccgcagactggacacccgagggggcgacccggggcagcacttggggctcggctacgcgcacagggggcgg cgggcagcagagtctgggcctccgcggccggggttccaccgccggccgcctccggctcgcgcaacgggagggaaaacttggacaaccctg ccacgcccagcccttggccgcgtggcttctcctgctcgaagcgcggtcccaggagtggccgacgctccctctcctgcccattccgcggatggg caatcccaggcggaactcccttgagggtctcagaatatctgggagacctcgggctcttgatctccgagacaccccgtttcgtagtggagaacagt ccagatcggggaagtttattttgcccaaagccgcatagaggccccctggccctcgattccctctgcggggctcagcagcgttgcagcctagacg ggtcttactgtgagccgagcagcctctgggaccacagaccttcccctaccccaacgttagaagccggagcccagcaaggagaagcgcgcac ctcctgctgtgaacgcgcacgacgccagggcagctgccagaggccatggcctggcgtgggcctggagcccctctggccagcctgcacggg gccagggctacgggataccagcagcgtgccctgggctggatggcaggagagacaggacttgaggctgtcccagaatgggctcaggcaggg cgaggatatcaggggaggtggtgtacaggaagcagccgcccagcttgcctggcacacagcaagccctgcccatgaaggcctactgccagaa cagtgggcgaggcccggcgtctctgtggagtcggtggggcccgggacagggcagcctgaggcaggtttccactggcggtgaaaggggccg tgtggcaaggacaggagagccagcctcagcccagcaggggaaggcggcccctgagtctccacctggctgctggcagccccactcggagca tcggcgaaactgaggcttgccaaagaagcctttgtccagagtcacgcagctggcgcggtggagccagggccagaacccgtgcaggctgatc ccagcctgccttctccactgtgccccg >MPP03(hTSPO_upstream_plus_intronic_prom)("P1 + P2")

(SEQ ID NO: 18)

GAGtgcatcaccgcgttgcggcctcatcagtcccacgactttgtgcccattttactcatgaggagatggaggcccagagagccagtcagaaa gtggctgggccaggactaagagtgcagcgcgctgcctccgtgccctgcgtcaacagctcaaggaactggggtgctccggaaatggggccaa ggctgctgggcagcaggacgctcagggccttggcctcaggagagcaaattccccactcggagatcggtcttgttgctgcattttattcatgggaa atctgaggctagaagagacgacaaacgacacgccgttggacacacggcaacgttttagatgttgggtctggccgggcggccgtcaccggtca ccatggggaggaggaggagccgagagacttgctcgcggccgggggggaggcagaagcgcgtcccgcgggagaggtggctagaggagtg agctcccggtcccgcggggacgcgagtgggcccagtgcccgggctgccaggcggggcggggcggggccgggcgactgagaggggcg gggcctggcggctgggaggggCGGGGCGGATGCGGGGACAGCGGCCTGGCTAACTCCTGCACGG CAGTGCCCTTCCCGGAGCGTGCCCTCGCCGCTGcacagtgaggacgggacgcggagggggcagcgggaaca cgccgcccgcatggctgcgacagttggcagcgccgcgggacagagggaaactgaggccggagccgcagactggacacccgagggggcg acccggggcagcacttggggctcggctacgcgcacagggggcggcgggcagcagagtctgggcctccgcggccggggttccaccgccg gccgcctccggctcgcgcaacgggagggaaaacttggacaaccctgccacgcccagcccttggccgcgtggcttctcctgctcgaagcgcg gtcccaggagtggccgacgctccctctcctgcccattccgcggatgggcaatcccaggcggaactcccttgagggtctcagaatatctgggag acctcgggctcttgatctccgagacaccccgtttcgtagtggagaacagtccagatcggggaagtttattttgcccaaagccgcatagaggcccc ctggccctcgattccctctgcggggctcagcagcgttgcagcctagacgggtcttactgtgagccgagcagcctctgggaccacagaccttccc ctaccccaacgttagaagccggagcccagcaaggagaagcgcgcacctcctgctgtgaacgcgcacgacgccagggcagctgccagagg -continued ccatggcctggcgtgggcctggagcccctctggccagcctgcacggggccagggctacgggataccagcagcgtgccctgggctggatgg caggagagacaggacttgaggctgtcccagaatgggctcaggcagggcgaggatatcaggggaggtggtgtacaggaagcagccgccca gcttgcctggcacacagcaagccctgcccatgaaggcctactgccagaacagtgggcgaggcccggcgtctctgtggagtcggtggggccc gggacagggcagcctgaggcaggtttccactggcggtgaaaggggccgtgtggcaaggacaggagagccagcctcagcccagcagggga aggcggcccctgagtctccacctggctgctggcagccccactcggagcatcggcgaaactgaggcttgccaaagaagcctttgtccagagtca cgcagctggcgcggtggagccagggccagaacccgtgcaggctgatcccagcctgccttctccactgtgccccg >MPP04(hTSPO_intronic_plus_upstream_prom)("P2 + P1")

(SEQ ID NO: 19)

CTGcacagtgaggacgggacgcggaggggggcagcgggaacacgccgcccgcatggctgcgacagttggcagcgccgcgggacagag ggaaactgaggccggagccgcagactggacacccgagggggcgacccggggcagcacttggggctcggctacgcgcacaggggggcgg cgggcagcagagtctgggcctccgcggccggggttccaccgccggccgcctccggctcgcgcaacgggagggaaaacttggacaaccctg ccacgcccagcccttggccgcgtggcttctcctgctcgaagcgcggtcccaggagtggccgacgctccctctcctgcccattccgcggatggg caatcccaggcggaactcccttgagggtctcagaatatctgggagacctcgggctcttgatctccgagacaccccgtttcgtagtggagaacagt ccagatcggggaagtttattttgcccaaagccgcatagaggcccccctggccctcgattccctctgcggggctcagcagcgttgcagcctagacg ggtcttactgtgagccgagcagcctctgggaccacagaccttcccctaccccaacgttagaagccggagcccagcaaggagaagcgcgcac ctcctgctgtgaacgcgcacgacgccagggcagctgccagaggccatggcctggcgtgggcctggagcccctctggccagcctgcacggg gccagggctacgggataccagcagcgtgccctgggctggatggcaggagagacaggacttgaggctgtcccagaatgggctcaggcaggg cgaggatatcaggggaggtggtgtacaggaagcagccgcccagcttgcctggcacacagcaagccctgcccatgaaggcctactgccagaa cagtgggcgaggcccggcgtctctgtggagtcggtggggcccgggacagggcagcctgaggcaggtttccactggcggtgaaaggggccg tgtggcaaggacaggagagccagcctcagcccagcaggggaaggcggcccctgagtctccacctggctgctggcagccccactcggagca tcggcgaaactgaggcttgccaaagaagcctttgtccagagtcacgcagctggcgcggtggagccagggccagaacccgtgcaggctgatc ccagcctgccttctccactgtgccccgtgcatcaccgcgttgcggcctcatcagtcccacgactttgtgcccattttactcatgaggagatggagg cccagagagccagtcagaaagtggctgggccaggactaagagtgcagcgcgctgcctccgtgccctgcgtcaacagctcaaggaactgggg tgctccggaaatggggccaaggctgctgggcagcaggacgctcagggccttggcctcaggagagcaaattccccactcggagatcggtcttg ttgctgcattttattcatgggaaatctgaggctagaagagacgacaaacgacacgccgttggacacacggcaacgttttagatgttgggtctggcc gggcggccgtcaccggtcaccatggggaggaggaggagccgagagacttgctcgcggccgggggggaggcagaagcgcgtcccgcggg agaggtggctttgaggagtgagctcccggtcccgcggggacgcgagtgggcccagtgcccgggctgccaggcggggcggggcggggcc gggcgactgagaggggcggggcctggcggctgggaggggCGGGGCGGATGCGGGGACAGCGGCCTGGCTA

ACTCCTGCACGGCAGTGCCCTTCCCGGAGCGTGCCCTCGCCGGGATCC

>MPP02(hTSPO_intronic5'prom)

(SEQ ID NO: 20)

taggtggcttcacccctctgcctgagcctgagtcctgtccctgccaagactccgcccagccgacgcccaccccagctttccctggactcatccct cagcagatatctggatcctgcctagcctggctcagcatgactcatcatgcagggtaccgcccctgcccacctgttccccaataccgcaattcagg agctgggcagttccccagaggccctaggaaactccccgcccccgaccaggctttctccactcctcccatctgaccgcctgttttctacgcctcac gaccctctgagccccttggcgcactccgacataaccacagccaggcctgagaagccgccagcctccgcagcgagtgtgagcacgggactca gaactggcttCTGcacagtgaggacgggacgcggaggggggcagcgggaacacgccgcccgcatggctgcgacagttggcagcgccgc gggacagagggaaactgaggccggagccgcagactggacacccgagggggcgacccggggcagcacttggggctcggctacgcgcaca gggggcggcgggcagcagagtctgggcctccgcggccggggttccaccgccggccgcctccggctcgcgcaacgggagggaaaacttg gacaaccctgccacgcccagcccttggccgcgtggcttctcctgctcgaagcgcggtcccaggagtggccgacgctccctctcctgcccattc cgcggatgggcaatcccaggcggaactcccttgagggtctcagaatatctgggagacctcgggctcttgatctccgagacaccccgtttcgtag tggagaacagtccagatcggggaagtttattttgcccaaagccgcatagaggcccccctggccctcgattccctctgcggggctcagcagcgttg cagcctagacgggtcttactgtgagccgagcagcctctgggaccacagaccttcccctaccccaacgttagaagccggagcccagcaaggag aagcgcgcacctcctgctgtgaacgcgcacgacgccagggcagctgccagaggccatggcctggcgtgggcctggagcccctctggccag -continued

```
cctgcacggggccagggctacgggataccagcagcgtgccctgggctggatggcaggagagacaggacttgaggctgtcccagaatgggc

tcaggcagggcgaggatatcaggggaggtggtgtacaggaagcagccgcccagcttgcctggcacacagcaagccctgcccatgaaggcc

tactgccagaacagtgggcgaggcccggcgtctctgtggagtcggtggggcccgggacagggcagcctgaggcaggtttccactggcggtg

aaaggggccgtgtggcaaggacaggagagccagcctcagcccagcaggggaaggcggcccctgagtctccacctggctgctggcagccc

cactcggagcatcggcgaaactgaggcttgccaaagaagcctttgtccagagtcacgcagctggcgcggtggagccagggccagaacccgt

gcaggctgatcccagcctgccttctccactgtgccccg
```

As used herein, the terms “treat,” treating,” “treatment,” and the like refer to reducing or ameliorating a disorder and/or symptoms associated therewith. It will be appreciated that, although not precluded, treating a disorder or condition does not require that the disorder, condition or symptoms associated therewith be completely eliminated.

By “transgene” is meant an exogenous nucleic acid molecule, introduced into a host cell, that encodes a polypeptide or polynucleotide to be expressed in the host cell.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms “treat,” treating,” “treatment,” and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term “or” is understood to be inclusive. Unless specifically stated or obvious from context, as used herein, the terms “a”, “an”, and “the” are understood to be singular or plural.

Unless specifically stated or obvious from context, as used herein, the term “about” is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2A is an alignment of the target sequences to be repeated in tandem to sequester miR-155. FIG. 2B is a map of the plasmid encoding the miR-155-Sponge, which contains a tandem of miR-155 target sequences in the 3' untranslated region of a phosphoglycerate kinase I (PGK)-GFP cassette and 5' of the mRNA stabilizer element Woodchuck Hepatitis Virus (WHP) Post-transcriptional Regulatory Element (Wpre). FIG. 2A discloses SEQ ID NOS: 2-3, respectively, in order of appearance.

FIG. 3A is a graph depicting miR155 levels in response to lipopolysaccharide stimulation in untransduced or in BV2 cells transduced at different multiplicities of infection (MOIs) by the miR155 sponge lentiviral vector. FIG. 3B is a graph depicting miR155 effect on BTB and CNC homology 1 (Bach1) expression levels in response to lipopolysaccharide stimulation in untransduced cells or in BV2 cells transduced at different MOIs by the miR155 sponge lentiviral vector. FIG. 3C is a graph depicting miR155 effect on CCAAT enhancer binding protein beta (Cebpb) expression levels in response to lipopolysaccharide stimulation in untransduced cells or in BV2 cells transduced at different MOIs by the miR155 sponge lentiviral vector. FIG. 3D is a graph depicting miR155 effect on inositol polyphosphate-5-phosphatase D (Inpp5d) expression levels in response to lipopolysaccharide stimulation in untransduced cells or in BV2 cells transduced at different MOIs by the miR155 sponge lentiviral vector. FIG. 3E is a graph depicting miR155 effect on tumor necrosis factor alpha (Tnfa) levels in response to lipopolysaccharide stimulation in untransduced cells or in BV2 cells transduced at different MOIs by the miR155 sponge lentiviral vector. In FIGS. 3B to 3E, expression of the analyzed gene was compared to the expression of glyceraldehyde-3-phosphate dehydrogenase (Gapdh).

FIG. 6A is a survival curve showing Nox2 shRNA (+/−MT1G) mice exceeded survival of control SOD1 transplanted. FIG. 6B is a survival curve showing miR-155-SP transplanted mice had an apparent survival advantage over controls during early and symptomatic phases but not in long term.

FIG. 7A is a bar graphs. Transduced cell engraftment was measured by ddPCR as lentiviral vector (LV) VCN (vector copy number) in brain DNA extracts from treated and control mice. FIGS. 7B and 7C are bar graphs. GFP+ cell chimerism was evaluated on the myeloid (CD45+CD11b+) compartment of the brain (FIG. 7B) and spinal cord (FIG. 7C) of treated and control mice by fluorescence activated cell sorting (FACS). Mean+/−SEM.

FIG. 8A is a bar graph presenting Iba1+ signal quantification (Mean+/−SEM) (asterisks indicate significance versus SOD&FP controls, at One Way Anova with Dunnet's post test). FIG. 8B provides representative images of the stained lumbar spinal cords.

DETAILED DESCRIPTION OF THE INVENTION

Figure 1:
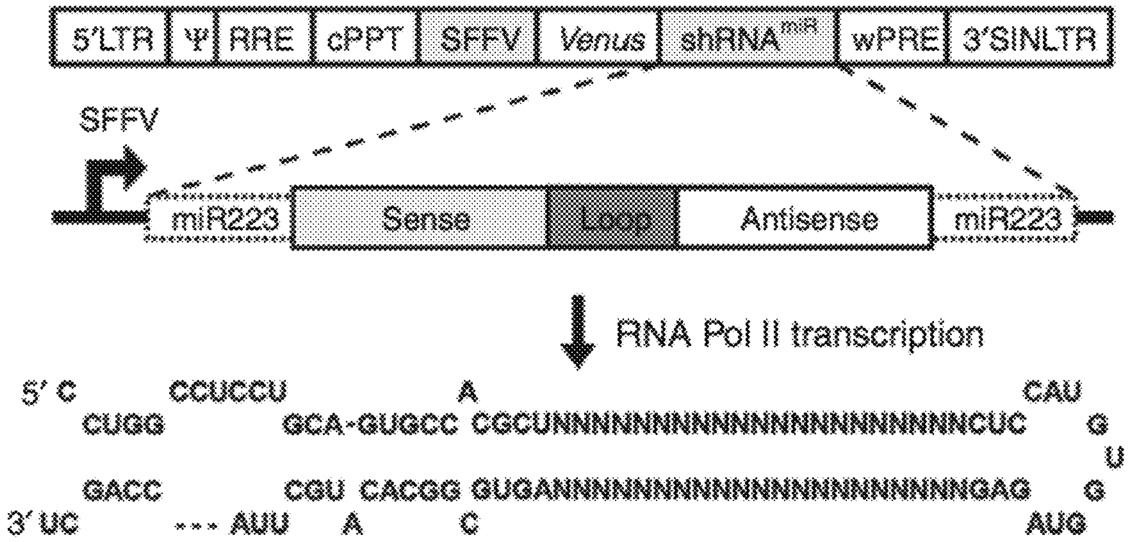
FIG. 1 is a diagram of a micro RNA 223 (miR223) retargeted microRNA 155 (miR155) shRNA. The abbreviations have the following meanings. LTR: long terminal repeat; RRE: Rev Response Element; cPPT: central polypurine tract; SFFV: spleen focus-forming virus; wPRE: Woodchuck Hepatitis Virus (WHP) Posttranscriptional Regulatory Element; SINLTR: Self-Inactivating Long Terminal Repeat. Figure discloses SEQ ID NO: 1.

The invention features compositions and methods for treating amyotrophic lateral sclerosis (ALS).

The invention is based at least in part on the discoveries that HSPCs engineered with lentiviral vectors (LVs) to express an shRNA targeting Nox2 (shNox2) or a microRNA sponge that targets microRNA 155 each inhibits neuroinflammation and supports neuronal survival in ALS. Additionally, the HSPCs used to reconstitute microglial populations can be modified to express a therapeutic agent that can mitigate neuroinflammation or other neurodegenerative stimuli. Among other things, the invention provides approaches for effective genetic engineering of central nervous system (CNS) microglia and myeloid cells for delivery of therapeutics to the brain for treatment of neurodegenerative diseases. Microglia replacement after transplantation of genetically modified hematopoietic stem cells (HSCs) in gene therapy clinical trials has demonstrated potential to restrain neural deterioration in monogenic neurodegenerative diseases. Not wishing to be bound by theory, early, during development, a group of myeloid hematopoietic progenitors integrate in the central nervous system (CNS) to provide life-long support. Indeed, recent advances in hematopoietic cell transplantation (HCT) provided evidence that, after myeloablation and infusion of HSCs, new microglia-like cells arise and settle in the central nervous system (CNS). These cells can integrate locally and functionally, and besides providing therapeutic molecules to surrounding cells can potentially positively contribute to the neural environment by defining and reshaping the neuronal network, maintaining neuron homeostasis, pruning synaptic spines, and of course being a functional part of the immune system for both surveillance and phagocytosis. Gene therapy clinical trials have been developed to target monogenic neurodegenerative disorders in which paracrine release of critical lysosomal enzymes demonstrated therapeutic benefit. Thus, engineering microglia via intra-CNS transplantation of genetically modified hematopoietic stem cells (HSCs) could offer a route for medical intervention for currently incurable neurodegenerative disorders, such as amyotrophic lateral sclerosis (ALS) and Alzheimer's disease (AD).

Nox2 and Micro RNA 155

Not wishing to be bound by any theory, Nox2 (gp91phox) is an important enzyme promoting the production of reactive oxygen species (ROS) in pathological conditions. NADPH-oxidase (NOX2), a multi-subunit enzyme complex involved in redox stress and induction of pro-inflammatory cytokines. Knockout of NOX2 in amyotrophic lateral sclerosis (ALS) mice ameliorates disease progression leading to increased survival of almost 100 days; this represents one of the largest effects observed for this mouse model. Lower NOX2 activity correlates with increased survival in ALS patients, suggesting that NOX2 may be a crucial disease modifier for ALS; thus, tight modulation of NOX2 activity may impact significantly on disease progression. miR-155 is one of the pro-inflammatory miRNAs most highly up-regulated in the spinal cord resident microglia in amyotrophic lateral sclerosis (ALS) mice and in post-mortem samples from ALS patients. miR-155 is associated with a loss of the molecular signature that characterizes homeostatic microglia in favor of a more neurotoxic phenotype. Thus, miR-155 may represent a crucial target acting as a master-regulator for restoration of a physiological neuro-supportive microglia function. In line with this observation, treatment with a miR-155 inhibitor has been shown to partially restore homeostatic microglia genes and prolonged survival of ALS mice. Increased ROS are a mediator of neurodegeneration in ALS. micro RNA 155 is a critical part of the machinery promoting cytotoxic neuroinflammatory responses in brain microglia. The present invention provides compositions that target Nox2 and miR-155, thereby reducing their expression in microglia, as well as cells, such as HSPCs, useful in the methods of the invention.

Regenerating Microglial Cells in the Central Nervous System

Microglia have a developmental origin distinct from that of bone marrow-derived myelomonocytes (Ginhoux et al. Science 330, 841-845 (2010)) the contents of which are incorporated herein by reference in their entirety). However, cells having a microglia-like phenotype can be derived from transplanted donor HSPCs. HSPCs capable generating microglia-like cells upon transplantation into myeloablated recipients are retained within human and murine long-term hematopoietic stem cells (HSCs), thereby providing a reservoir of pluripotent cells capable of differentiating into therapeutic microglia for the treatment of ALS.

HSPCs, systemically administered to a subject, can migrate to the brain and differentiate into microglia-like cells, thereby replacing the dead or damaged microglial cells. However, as described herein, an alternative process, intracerebroventricular administration of HSPCs, results in faster and more widespread microglia reconstitution. Thus, in some embodiments of the present disclosure, HSPCs are administered to a subject intracerebroventricularly. In some embodiments, the HSPCs are delivered into the cerebrospinal fluid of the cerebral ventricles. This administration route avoids inefficiencies associated with systemically administered compositions having to cross the blood brain barrier. In some embodiments of the present disclosure, intracerebroventricular administration results in faster establishment of progeny cells in the recipient's brain than systemic administration. In some embodiments, the replacement of microglial cells is more widespread using this direct delivery method.

Engraftment and differentiation of HSPCs may be difficult in environments comprising endogenous microglial cells. Endogenous microglial cells may be able to outcompete transplanted HSPCs, and neuroinflammation associated with dying microglial cells may generate an unfavorable environment (e.g., increased inflammation) for HSPC engraftment. To overcome these barriers to HSPC engraftment, in some embodiments, the existing microglial cells are ablated by exposure to an agent capable of removing endogenous microglial cells. For example, pre-transplant administration of a conditioning regimen employing an alkylating agent is an effective means for ablating endogenous microglia precursors (Capotondo et al. (2012); Wilkinson et al. Mol Ther 21, 868-876 (2013), the contents of which are incorporated herein by reference in their entirety). In some embodiments of the present disclosure, the alkylating agent is busulfan. The alkylating agent can be delivered to a subject by any method known in the art. For example, the alkylating agent can be delivered orally, intravenously, intraarterially, intraperitoneally, intramuscularly, subcutaneously, intrathecally, by perfusion through a regional catheter, or by any other means known in the art. In addition to alkylation agents, such as busulfan, CSF-IR inhibitors (e.g., PLX3397 having and PLX5622), and liposomal clodronate may be used (Han et al. Molecular Brain, 10:25, 2017), optionally they may be used in combination with the nanoparticles described, for example, in WO2019191650, which is incorporated herein.

In general, the term nanoparticle refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention. Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. In one embodiment, nanoparticles based on self-assembling bioadhesive polymers are contemplated, which may be applied to oral delivery of agents, intravenous delivery of agents and nasal delivery of agents, all to the brain. Other embodiments, such as oral absorption and ocular deliver of hydrophobic drugs are also contemplated. The molecular envelope technology involves an engineered polymer envelope which is protected and delivered to the site of the disease (Mazza et al. ACS Nano 7, 1016-1026 (2013); Siew et al. Mol Pharm 9, 14-28 (2012); Lalatsa et al. J Control Release 161, 523-536 (2012); Lalatsa et al. Mol Pharm 9, 1665-1680 (2012); Garrett et al. J Biophotonics 5, 458-468 (2012); Uchegbu, Expert Opin Drug Deliv 3, 629-640 (2006); Uchegbu et al. Int J Pharm 224, 185-199 (2001); Qu et al. Biomacromolecules 7, 3452-3459 (2006)).

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation, which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS).

Particle delivery systems within the scope of the present invention may be provided in any form, including but not limited to solid, semi-solid, emulsion, or colloidal particles. As such any of the delivery systems described herein may be provided as particle delivery systems within the scope of the present invention.

After ablation of endogenous microglial cells or precursors thereof, in some embodiments, HSPCs are administered to the subject. In some embodiments, HSPCs are delivered intracerebroventricularly after ablation of the endogenous microglial cells or precursors thereof. In some embodiments, HSPCs are delivered intravascularly after ablation of the endogenous microglial cells or precursors thereof.

Modified Cells

Some aspects of the present disclosure provide cells (e.g., HSPCs) that are modified to express one or more exogenous nucleic acid molecules. In some embodiments, an exogenous nucleic acid molecule encodes a neuroprotective agent that enhances the establishment or function of microglial cells in the central nervous system of a subject having or suspected of having ALS. In some embodiments, cells are provided that express a neuroprotective agent that inhibit neurodegeneration.

The modified cells of the present disclosure are HSPCs in some embodiments. In some embodiments, the cells are microglial cells derived from modified HSPCs. The HSPCs may be isolated from a subject having, suspected of having, or having a propensity to develop ALS. The cells are then modified, cultured, and administered to the subject. These autologous cells are less likely to elicit an immune response after being administered to the subject than an allogeneic cell. However, in some embodiments, the HSPCs are isolated from a healthy donor. Methods of isolating HSPCs from a donor are known in the art.

Nox2 shRNA

In some embodiments of the present disclosure, modified HSPCs or their progeny express a neuroprotective agent that down-regulates expression of Nox2, an enzyme involved in the production of reactive oxygen species (ROS), which can mediate neurodegeneration in ALS patients. In some embodiments, the neuroprotective agent that targets Nox2 is an inhibitory nucleic acid such as a RNAi molecule. In some embodiments, the RNAi molecule is a short hairpin RNA (shRNA) molecule that comprises a sharp hairpin turn, which provides the molecule's stem-loop structure. The double-stranded stem comprises a sense strand hybridized to a complementary antisense strand, and the loop is single stranded. The sense strand of the shRNA comprises a nucleotide sequence that is complementary to a mRNA polynucleotide encoding Nox2. Upon transcription of the shRNA, the shRNA is processed such that the loop and the antisense strand are degraded. The sense strand is incorporated into the RNA-interfering silencing complex, and upon binding of the sense strand to Nox2 mRNA, the RNAi machinery degrades or silences the Nox2 mRNA, thereby downregulating Nox2 activity.

In some embodiments, the modified cells of the present disclosure express more than one shRNA to down-regulate Nox2 activity. For example, a first shRNA will have a nucleotide sequence complementary to a first nucleotide sequence of Nox2 mRNA, and a second shRNA will have a sense strand comprising a nucleotide sequence complementary to a different Nox2 mRNA nucleotide sequence. Nox2 activity may be downregulated by multiple shRNA molecules having different sense strands that specifically bind different sequences in the Nox2 mRNA, even if the Nox2 mRNA comprises variation in the nucleotide sequence relative to a reference sequence. In particular embodiments, a lentiviral vector comprises a polynucleotide encoding shNox2.

miRNA Sponges micro RNAs (miRNAs) are small, noncoding RNA molecules involved in RNA silencing and other post-transcriptional gene expression regulation. There are dozens of families of miRNAs. While some miRNAs regulate many targets, some targets are regulated by multiple different miRNAs. Similar to the shRNA described above, miRNAs are incorporated into the RNA-interfering silencing complex to affect gene expression. Upon hybridization of the miRNA to its target mRNA, the RNA-interfering silencing complex degrades the mRNA-miRNA duplex, thereby inhibiting translation of the mRNA molecule.

miRNAs have been previously associated with disease and are attractive targets for therapeutic compositions and methods. For example, in some aspects of the present disclosure, modified cells express an agent that downregulates the activity of a miRNA that contributes to the ALS phenotype. In some embodiments, the agent is a polynucleotide that is complementary to the miRNA. In some embodiments, the agent is a miRNA sponge, wherein the miRNA sponge specifically binds the miRNA.

A miRNA sponge comprises multiple binding sites for two or more nucleic acid sequences in a target miRNA. Complementary sequences may be separated by noncomplementary sequences such that binding of the miRNA sponge to the target sequences of the miRNA induces formation of a single-stranded bulge in the miRNA that is susceptible to enzymatic degradation. Degradation of the miRNA is not required for its inhibition as binding of the miRNA to the sponge will sequester the miRNA and effectively downregulate its activity. In some embodiments, the miRNA sponge transgene may encode multiple binding sites for the same miRNA, but it is also contemplated that a composition encoding a miRNA sponge may encode multiple binding sites that have nucleotide sequences that are complementary to different miRNAs.

micro RNA 155 (miR155) plays a role in the pathology observed in SOD1 mice, a model organism for ALS. This proinflammatory miRNA is highly upregulated in microglia in the spinal cord of a mouse model of ALS and in post-mortem samples from human ALS patients (Parisi et al., Cell Death Dis., 4:e959 (2013); Butovsky et al., Ann Neurol., 77 (1): 75-99 (2015), the contents of which are herein incorporated by reference in their entirety). Specifically, miR155 contributes to cytotoxic neuroinflammatory responses in brain microglia. In some embodiments of the present disclosure, cells are modified to express a miRNA sponge to downregulate the activity of miRNA 155 (miR155).

Metallothioneins

Additionally, contemplated herein are modified HSPCs that express a metallothionein protein (e.g., MT1G) in combination with a shNox2 or a miRNA. Metallothioneins are intracellular cysteine-rich, metal-binding proteins involved in homeostasis of essential metals such as zinc and copper, detoxification of toxic metals such as cadmium, and protection against oxidative stress. Furthermore, metallothioneins have been implicated in neuroprotection and neurodegeneration in several neurological conditions (Juarez-Rebollar et al. (2017); Ruttkay-Nedecky et al. (2013), the contents of which are herein incorporated by reference in their entirety). Overexpression of metallothioneins (such as MT1G) contributes to neuroprotection in LSD mouse models for infantile neuronal ceroid lipofuscinosis and Krabbe disease. Thus, metallothioneins may be beneficial for ALS.

Some embodiments of the present disclosure provide a modified cell that expresses a metallothionein encoded by an exogenous nucleic acid molecule. The metallothionein is a MT1, MT2, MT3, or MT4 metallothionein in some embodiments. In some embodiments, the metallothionein is a MT1. In some embodiments the MT1 metallothionein is a MT1A, MT1B, MT1E, MT1F, MT1G, MT1H, MT1L, MT1M, or a MT1X metallothionein. In some embodiments, a cell expresses more than one metallothionein from an exogenous nucleic acid molecule. In some embodiments, a cell expresses MT1G from an exogenous nucleic acid molecule. In some embodiments, the cell is an HSPC or its progeny. In some embodiments, the cell is a microglia or microglia-like cell. Metallothioneins are described in International Application Nos. PCT/US2018/013908 and PCT/US2018/013909, the contents of which are incorporated herein by reference in their entirety.

Some embodiments of the present disclosure provide a modified cell that expresses a metallothionein encoded by an exogenous nucleic acid molecule and a miRNA sponge. The metallothionein is a MT1, MT2, MT3, or MT4 metallothionein in some embodiments. In some embodiments, the modified cell expresses a MT1A, MT1B, MT1E, MT1F, MT1G, MT1H, MT1L, MT1M, or a MT1X metallothionein and a miRNA sponge. In some embodiments, a cell expresses MT1G from an exogenous transgene and a miR155 sponge. In some embodiments, the cell is an HSPC or its progeny. In some embodiments, the cell is a microglia or microglia-like cell.

Some embodiments of the present disclosure provide a modified cell that expresses an anti-Nox2 shRNA and a metallothionein encoded by exogenous transgenes. In some embodiments, the metallothionein is a MT1, MT2, MT3, or MT4 metallothionein. In some embodiments, the modified cell expresses a MT1A, MT1B, MT1E, MT1F, MT1G, MT1H, MT1L, MT1M, or a MT1X metallothionein and an anti-Nox2 shRNA. In some embodiments, the modified cell expresses MT1G and an anti-Nox2 shRNA from exogenous transgenes. In some embodiments, the cell is an HSPC or its progeny. In some embodiments, the cell is a microglia or microglia-like cell.

Some embodiments of the present disclosure provide a modified cell that expresses anti-Nox2 shRNA, a miRNA sponge, and a metallothionein encoded by exogenous nucleic acid molecules. In some embodiments, the metallothionein is a MT1, MT2, MT3, or MT4 metallothionein. In some embodiments, the modified cell expresses a MT1A, MT1B, MT1E, MT1F, MT1G, MT1H, MT1L, MT1M, or a MT1X metallothionein, an anti-Nox2 shRNA, and a miRNA sponge. In some embodiments, the modified cell expresses MT1G, anti-Nox2 shRNA, a miRNA sponge from exogenous nucleic acid molecules. In some embodiments, the cell is an HSPC or its progeny. In some embodiments, the cell is a microglia or microglia-like cell.

In some embodiments, a modified cell expresses a Nox2 shRNA, a miRNA sponge, a metallothionein (or fragment thereof), or any combination thereof, wherein the anti-Nox2 shRNA, the miRNA sponge, and/or the metallothionein are encoded by exogenous nucleic acid molecules. In some embodiments, the metallothionein is a MT1, MT2, MT3, or MT4 metallothionein. In some embodiments, the modified cell expresses a MT1A, MT1B, MT1E, MT1F, MT1G, MT1H, MT1L, MT1M, or a MT1X metallothionein, an anti-Nox2 shRNA, and/or a miRNA sponge. In some embodiments, the modified cell expresses MT1G, anti-Nox2 shRNA, and a miRNA sponge from exogenous nucleic acid molecules. In some embodiments, the cell is an HSPC or its progeny. In some embodiments, the cell is a microglia or microglia-like cell.

Hemizygous CX3CR1 Cells

CX3CR1, also known as the fractalkine receptor, is a seven-transmembrane domain receptor belonging to G protein-coupled receptors family. Being a G protein-coupled receptor, CX3CR1's role is mostly inhibitory as it acts to reduce production of cAMP and prevent triggering signaling cascades mediated by second messengers. The intracellular pathways controlled by CX3CR1 signaling involve mainly PLC, PI3K, and ERK regulation, which modulate cell migration, adhesion, proliferation and survival. It is expressed in several cell types (e.g., monocytes, natural killer cells, T cells, and smooth muscle cells). Microglia are the only cell in the central nervous system that express CX3CR1, which they express at high levels, particularly during development and in response to brain damage/pathology.

Fractalkine (CX3CL1) is the unique ligand for the chemokine receptor CX3CR1 and is expressed either as membrane-bound molecule or in a soluble form. Fractalkine cleavage is mediated by at least two enzymes, ADAM10 and ADAM17, which are active in homeostatic and inflammatory conditions, respectively. Fractalkine acts mainly as adhesion molecule in its membrane-bound form, while it has chemotactic properties towards CX3CR1 in its soluble form. Local production and membrane expression of CX3CL1 and CX3CR1 are controlled by other cytokines, like TNF$\alpha$, IL-1, IFN$\gamma$, NO, and hypoxia.

Activation of the CX3CR1-CX3CL1 axis leads to maintenance of microglia in a quiescent state and of homeostasis in the neuronal network. Under physiological conditions, CX3CL1 seems to inhibit microglial activation, while in particular conditions a paradoxical promotion of an inflammatory response may occur. Neurons are the greater producers of CX3CL1 in the brain and this axis is important for communication with microglia cells. Astrocytes (GFAP+) also display constitutive mRNA expression for CX3CL1. Endothelial cells in the brain and spinal cord, as opposed to those in other locations, do not present constitutive CX3CL1 expression on the surface, which suggests that it is rather dependent on their activation. CX3CL1 and CX3CR1 are also expressed in the choroid plexus.

To enhance the ability of HSPCs to generate microglia-like progeny upon transplantation, a mouse model, hemizygous for CX3CR1, and in which a GFP reporter gene has replaced one CX3CR1 allele (B6.129P-CX3CR1tm1Litt/J) was used to demonstrated that i) transplantation of total bone marrow or HSPCs from donor mice haplo-insufficient for the CX3CR1 gene results in an greater and faster appearance of microglia like donor cells in the recipients' brain, as compared to standard wild type donors, and that ii) in the context of competitive transplantation, haplo-insufficient donor derived cells contribute to a greater extent as compared to wild type donor cells to the repopulation of the hematopoietic organs and brain myeloid compartment of the recipients. A branching study performed on the engrafted cells, showed that CX3CR1+/GFP cells also acquire a more mature microglia-like morphology.

Thus, the present disclosure contemplates isolating HSPCs and knocking out one allele of CX3CR1 to create a hemizygous cell, which may be modified as described herein to express shNox2 and/or a miR155 sponge, and the modified cells administered to a subject in need thereof. The present disclosure also contemplates modifying a CX3CR1 hemizygous HSPC to incorporate a nucleic acid sequence encoding a peptide in the missing CX3CR1 allele locus. In this way, the hemizygous HSPCs are manipulated to express a therapeutic agent. Alternatively, an isolated HSPC may be edited to remove one copy of CX3CR1 to generate a hemizygous HSPC. Editing a single copy of the CX3CR1 comprises, in some embodiments, replacing the CX3CR1 allele with an exogenous nucleic acid molecule encoding a therapeutic agent. Such editing is carried out using any method known in the art.

Gene editing is a major focus of biomedical research, embracing the interface between basic and clinical science. "Gene editing" tools can manipulate a cell's DNA sequence at a specific chromosomal locus without introducing mutations at other sites of the genome. This technology effectively enables a researcher to manipulate the genome of a cell in vitro or in vivo.

In one embodiment, gene editing involves targeting an endonuclease to a specific site in a genome to generate a double strand break at the specific location. If a donor DNA molecule (e.g., a plasmid or oligonucleotide) is introduced, interactions between the nucleic acid comprising the double strand break and the introduced DNA can occur, especially if the two nucleic acids share homologous sequences. In this instance, a process termed "gene targeting" can occur, in which the DNA ends of the chromosome invade homologous sequences of the donor DNA by homologous recombination. By using the donor plasmid sequence as a template for homologous recombination, a seamless knock out of the gene of interest can be accomplished. Importantly, if the donor DNA molecule includes a deletion within the target gene (e.g., CX3CR1), homologous recombination-mediated double strand break repair will introduce the donor sequence into the chromosome, resulting in the deletion being introduced within the chromosomal locus. By targeting the nuclease to a genomic site that contains the target gene, the concept is to use double strand break formation to stimulate homologous recombination and to thereby replace the functional target gene with a deleted form of the gene. The advantage of the homologous recombination pathway is that it has the potential to generate seamlessly a knockout of the gene in place of the previous wild-type allele.

Genome editing tools may use double strand breaks to enhance gene manipulation of cells. Such methods can employ zinc finger nucleases, described for example in U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; and 6,479,626; and U.S. Pat. Publ. Nos. 20030232410 and US2009020314, which are incorporated herein by reference); Transcription Activator-Like Effector Nucleases (TALENs; described for example in U.S. Pat. Nos. 8,440,431; 8,440,432; 8,450,471; 8,586,363; and 8,697,853; and U.S. Pat. Publ. Nos. 20110145940; 20120178131; 20120178169; 20120214228; 20130122581; 20140335592; and 20140335618; which are incorporated herein by reference), and the CRISPR (Clustered Regularly Interspaced Short Palindromic Repeats)/Cas9 system (described for example in U.S. Pat. Nos. 8,697,359; 8,771,945; 8,795,965; 8,871,445; 8,889,356; 8,906,616; 8,932,814; 8,945,839; 8,993,233; and 8,999,641; and U.S. Pat. Publ. Nos. 20140170753; 20140227787; 20140179006; 20140189896; 20140273231; 20140242664; 20140273232; 20150184139; 20150203872; 20150031134; 20150079681; 20150232882; and 20150247150, which are incorporated herein by reference). For example, zinc finger nuclease DNA sequence recognition capabilities and specificity can be unpredictable. Similarly, TALENs and CRISPR/Cas9 cleave not only at the desired site, but often at other "off-target" sites, as well. These methods have significant issues connected with off-target double-stranded break induction and the potential for deleterious mutations, including indels, genomic rearrangements, and chromosomal rearrangements, associated with these off-target effects. Zinc finger nucleases and TALENs entail use of modular sequence-specific DNA binding proteins to generate specificity for about 18 bases sequences in the genome.

RNA-guided nucleases-mediated genome editing, based on Type 2 CRISPR (Clustered Regularly Interspaced Short Palindromic Repeat)/Cas (CRISPR Associated) systems, offers a valuable approach to alter the genome. In brief, Cas9, a nuclease guided by single-guide RNA (sgRNA), binds to a targeted genomic locus next to the protospacer adjacent motif (PAM) and generates a double-strand break. The zinc finger nuclease is then repaired either by non-homologous end joining, which leads to insertion/deletion (indel) mutations, or by homology-directed repair, which requires an exogenous template and can generate a precise modification at a target locus (Mali et al., Science, Feb. 15, 2013; 339 (6121): 823-6, the contents of which are herein by reference in their entirety). Unlike gene therapy methods that add a functional, or partially functional, copy of a gene to a subject's cells but retain the original dysfunctional copy of the gene, this system can remove the defect in the dysfunctional copy. Genetic correction using modified nucleases has been demonstrated in tissue culture cells and rodent models of rare diseases.

CRISPR has been used in a wide range of organisms including baker's yeast (*S. cerevisiae*), zebra fish, nematodes (e.g., *C. elegans*), plants, mice, and several other organisms. Additionally, CRISPR has been modified to make programmable transcription factors that allow scientists to target and activate or silence specific genes. Libraries of tens of thousands of guide RNAs are now available. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length, with some CRISPR spacer sequences exactly matching sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define eight CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome: The sporadic distribution of the CRISPR/Cas subtypes suggests that the system is subject to horizontal gene transfer during microbial evolution.

Exogenous DNA is apparently processed by proteins encoded by Cas genes into small elements (about thirty base pairs in length), which are then inserted into the CRISPR locus near the leader sequence. RNAs from the CRISPR loci are constitutively expressed and are processed by Cas proteins to small RNAs comprising individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype Ecoli) proteins (called CasA-E in *E. coli*) form a functional complex, Cascade, that processes CRISPR RNA transcripts into spacer-repeat units that Cascade retains. In other prokaryotes, Cas6 processes CRISPR transcripts. Interestingly, CRISPR-based phage inactivation in *E. coli* requires Cascade and Cas3, but neither Cas1 nor Cas2. The Cmr (Cas RAMP module) proteins found in *Pyrococcus furiosus* and other prokaryotes form a functional complex with small CRISPR RNAs that recognizes and cleaves complementary target RNAs. RNA-guided CRISPR enzymes are classified as type V restriction enzymes.

See also U.S. Patent Publication 2014/0068797, which is incorporated by reference in its entirety.

gRNA

As an RNA guided protein, Cas9 requires an RNA molecule to direct the recognition of DNA targets. Though Cas9 preferentially interrogates DNA sequences containing a protospacer adjacent motif (PAM) sequence (i.e., NGG). However, the Cas9-gRNA complex requires a substantial complementarity between the guide RNA (gRNA) and the target nucleic acid sequence to create a double strand break. Synthetic gRNA can be designed to combine the essential RNA sequences for Cas9 targeting into a single RNA expressed with the RNA polymerase type 2I promoter U6 driving expression. Synthetic gRNAs are slightly over 100 bases at the minimum length and contain a portion which is targets the 20 protospacer nucleotides immediately preceding the PAM sequence NGG.

In one approach, an HSPC cell is altered to delete or inactivate a CX3CR1 allele using a CRISPR-Cas system. Cas9 can be used to target a CX3CR1 gene. Upon target recognition, Cas9 induces double strand breaks in the CX3CR1 target gene. Homology-directed repair (HDR) at the double-strand break site can allow insertion of an inactive or deleted form of the CX3CR1 sequence. In some embodiments, homology-directed repair (HDR) at the double-strand break site can allow insertion of an expression cassette of the invention.

In one approach, an HSPC cell is altered to delete or inactivate a TSPO allele using a CRISPR-Cas system. Cas9 can be used to target a TSPO gene. Upon target recognition, Cas9 induces double strand breaks in the TSPO target gene. Homology-directed repair (HDR) at the double-strand break site can allow insertion of an inactive or deleted form of the TSPO sequence. In some embodiments, homology-directed repair (HDR) at the double-strand break site can allow insertion of an expression cassette of the invention.

The following US patents and patent publications are incorporated herein by reference: U.S. Pat. No. 869,735; 20140170753; 20140179006; 20140179770; 20140186843; 20140186958; 20140189896; 20140227787; 20140242664; 20140248702; 20140256046; 20140273230; 20140273233; 20140273234; 20140295556; 20140295557; 20140310830; 20140356956; 20140356959; 20140357530; 20150020223; 20150031132; 20150031133; 20150031134; 20150044191; 20150044192; 20150045546; 20150050699; 20150056705; 20150071898; 20150071899; 20150071903; 20150079681; 20150159172; 20150165054; 20150166980; and 20150184139.

Expression of shNox2 or a microRNA 155 Sponge

To express a polynucleotide encoding shNox2 or a microRNA 155 sponge nucleic acid molecule encoding these polynucleotides can be inserted into expression vectors by techniques known in the art. For example, double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

The present disclosure also includes vectors (e.g., recombinant plasmids) that include nucleic acid molecules (e.g., transgenes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a polypeptide, or fragment thereof, operatively linked to regulatory sequences such as promoter sequences, terminator sequences, long terminal repeats, untranslated regions, enhancers, and the like, as defined herein. Recombinant expression vectors allow for expression of the genes or nucleic acids included in them. In particular embodiments, a promoter is described in U.S. Provisional Application No. 62/908,966, which is incorporated by reference in its entirety. In some embodiments, the promoter comprises a translocator protein (TPSO) promoter. In some embodiments, the regulatory sequences comprise a translocator protein (TPSO) promoter in combination with one or more enhancers. In some embodiments, the regulatory sequences comprise P1, P2, P1+P2, or P2+P1 alone or in combination with one or more of E1, E2, E1.1, and E1.2.

In some embodiments, the regulatory sequences comprises P1+P2, P1, or E1+P1, where the sequence to the left of "+" is oriented 5' to the sequence right of the "+".

In some embodiments of the present disclosure, one or more DNA molecule having a nucleotide sequence encoding one or more polypeptides or polynucleotides described herein are operatively linked to one or more regulatory sequences, which can integrate the desired DNA molecule into a eukaryotic cell. Cells which have been stably transfected or transduced by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection or co-transduction. Any additional elements needed for optimal synthesis of polynucleotides or polypeptides described herein would be apparent to one of ordinary skill in the art.

In some embodiments, an HSPC may be modified by introducing an exogenous nucleic acid molecule into the cell. The exogenous nucleic acid may comprise a transgene encoding a therapeutic agent for the treatment of ALS disease. The exogenous nucleic acid, in some embodiments, comprises regulatory elements for expressing a transgene. For example, an exogenous nucleic acid molecule may comprise a transgene encoding a therapeutic agent for the treatment of ALS and a promoter for expressing the transgene. In some embodiments, the promoter is a constitutively active promoter such as, for example, the cytomegalovirus (CMV), simian virus 40 (SV40) promoter. In some embodiments, the promoter may be a tissue-specific promoter, wherein the transgene is expressed upon engraftment and differentiation of the HSPC. For example, tetracycline is a drug that can be used to activate a tetracyclin-sensitive promoter. In some embodiments, a neuronal specific promoter is the synapsin (Syn) promoter. In some embodiments, the promoter may be an inducible promoter, wherein the transgene is expressed only in the presence or absence of a particular compound. In some embodiments, microglial or microglial-like cells derived from an HSPC comprising a transgene driven by a brain-specific promoter transplanted into the brain of a subject will express the transgene. In some embodiments, the exogenous nucleic acid molecule may comprise, in addition to a transgene, a detectable label or other marker that allows identification of cells that have been successfully modified or that are derived from cells that have been successfully modified to express the transgene.

Methods of introducing exogenous nucleic acid molecules into a cell are known in the art. For example, eukaryotic cells can take up nucleic acid molecules from the environment via transfection (e.g., calcium phosphate-mediated transfection). Transfection does not employ a virus or viral vector for introducing the exogenous nucleic acid into the recipient cell. Stable transfection of a eukaryotic cell comprises integration into the recipient cell's genome of the transfected nucleic acid, which can then be inherited by the recipient cell's progeny.

Eukaryotic cells (i.e., HSPCs) can be modified via transduction, in which a virus or viral vector stably introduces an exogenous nucleic acid molecule to the recipient cell. Eukaryotic transduction delivery systems are known in the art. Transduction of most cell types can be accomplished with retroviral, lentiviral, adenoviral, adeno-associated, and avian virus systems, and such systems are well-known in the art. While retroviruses systems are generally not compatible with neuronal cell transduction, lentiviruses are a genus of retroviruses well-suited for transducing stem cells as well as neuronal cells. Thus, in some embodiments of the present disclosure, the viral vector system is a lentiviral system. In some embodiments, the viral vector system is an avian virus system, for example, the avian viral vector system described in U.S. Pat. No. 8,642,570, DE102009021592, PCT/EP2010/056757, and EP2430167, the contents of which are incorporated herein by reference in their entirety. In some embodiments, the viral vectors are assembled or packaged in a packaging cell prior to contacting the intended recipient cell. In some embodiments, the vector system is a self-inactivating system, wherein the viral vector is assembled in a packaging cell, but after contacting the recipient cell, the viral vector is not able to be produced in the recipient cell.

The components of a viral vector are encoded on plasmids, and because efficiencies of transduction decrease with large plasmid size, multiple plasmids that have different viral sequences necessary for packaging may be necessary. For example, in a lentiviral vector system, a first plasmid may comprise a nucleotide sequence encoding a Group antigens (gag) and/or a reverse transcriptase (pol) gene, while a second plasmid encodes regulator of expression of virion proteins (rev) and/or envelope (env) genes. The exogenous nucleic acid molecule comprising a transgene can be packaged into the vector and delivered into a recipient cells where the transgene is integrated into the recipient cell's genome. Additionally, the transgene may be packaged using a split-packaging system as described in U.S. Pat. No. 8,642,570, DE102009021592, PCT/EP2010/056757, and EP2430167.

After the introduction of one or more vector(s), host cells are cultured prior to administration to a subject. In some embodiments, the Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography, and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Pharmaceutical Compositions

Compositions contemplated in the present disclosure include pharmaceutical compositions comprising cells expressing a neuroprotective agent. In some embodiments, the neuroprotective agent is an anti-Nox2 shRNA, a miRNA sponge (i.e., an miRNA155 sponge) a metallothionein, or a combination thereof. Pharmaceutical compositions can comprise autogenic or allogenic cells that are modified to express a therapeutic agent.

Hematopoietic stem progenitor cells (HSPCs) as described herein can be administered as therapeutic compositions (e.g., as pharmaceutical compositions). Cellular compositions as described herein can be provided as sterile liquid preparations, e.g., isotonic aqueous solutions, suspensions, emulsions, dispersions, or viscous compositions, which may be buffered to a selected pH. A liquid preparation may be easier to prepare than a gel, another viscous composition, and a solid composition. Additionally, a liquid composition may be more convenient to administer (i.e., by injection). Viscous compositions, on the other hand, can be formulated within the appropriate viscosity range to provide longer contact periods with specific tissues. Liquid or viscous compositions can comprise a carrier, which can be a solvent or dispersing medium comprising, for example, water, saline, phosphate buffered saline, polyol (e.g., glycerol, propylene glycol, liquid polyethylene glycol, and the like), and suitable mixtures thereof.

Sterile injectable solutions can be prepared by incorporating the cells described herein in a sufficient amount of an appropriate diluent. Such compositions may be in admixture with a suitable carrier or excipient such as sterile water, physiological saline, glucose, dextrose, or another carrier or excipient suitable for delivering live cells to a subject. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "Remington's Pharmaceutical Science", 17th edition, 1985, incorporated herein by reference, may be consulted to prepare suitable preparations, without undue experimentation.

Additives that enhance the stability and sterility of the cellular compositions, including antimicrobial preservatives, antioxidants, chelating agents, and buffers, can be added. Prevention of the action of microorganisms can be ensured by an antibacterial or antifungal agent including, but not limited to, parabens, chlorobutanol, phenol, and sorbic acid. According to the present disclosure, however, any vehicle, diluent, or additive used must be compatible with the cells.

The compositions can be isotonic, i.e., they have the same osmotic pressure as blood and cerebrospinal fluid. The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride may be suitable for buffers containing sodium ions.

Viscosity of the compositions, if desired, can be maintained at a selected level using a pharmaceutically acceptable thickening agent. In some embodiments, the thickening agent is methylcellulose, which is readily and economically available and is easy to work with. Other suitable thickening agents include, but are not limited to, xanthan gum, carboxymethyl cellulose, hydroxypropyl cellulose, and carbomer. The concentration of the thickener will depend upon the agent selected and the amount of the agent used. Suitable carriers and other additives may be chosen depending on the route of administration and the nature of the dosage form (e.g., a liquid dosage form can be formulated into a solution, a suspension, a gel, or another liquid form, such as a time release formulation or liquid-filled form).

An effective amount of cells to be administered can vary for the subject being treated. In one embodiment, between about $10^4$ to about $10^8$ cells, and in another embodiment between about $10^5$ to about $10^7$ cells are administered to a subject.

The skilled artisan can readily determine the amounts of cells and optional additives, vehicles, and/or carrier in compositions to be administered. In one embodiment any additive (in addition to the cell(s)) is present in an amount of about 0.001% to about 50% (weight) solution in phosphate buffered saline, and the active ingredient is present in the order of micrograms to milligrams, such as about 0.0001% to about 5 wt %. In another embodiment, the active ingredient is present at about 0.0001% to about 1 wt %. In yet another embodiment, the active ingredient is present at about 0.0001% to about 0.05 wt %. In still other embodiments, the active ingredient is present at about 0.001% to about 20 wt %. In some embodiments, the active ingredient is present at about 0.01% to about 10 wt %. In another embodiment, the active ingredient is present at about 0.05% to about 5 wt %. For any composition to be administered to an animal or human, and for any particular method of administration, toxicity can be determined by measuring the lethal dose (LD) and $LD_{50}$ in a suitable animal model e.g., a rodent such as mouse. The dosage of the composition(s), concentration of components therein, and timing of administering the composition(s), which elicit a suitable response can also be determined. Such determinations do not require undue experimentation in light of the knowledge of the skilled artisan, this disclosure, and the documents cited herein. The time for sequential administrations can also be ascertained without undue experimentation.

Methods of Treatment

A health care professional may diagnose a subject as having a neurodegenerative disease (ALS) by the assessment of one or more symptoms of a neurodegenerative disease in the subject. Non-limiting symptoms of a neurodegenerative disease in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disease. A health care professional may diagnose a subject as having a neurodegenerative disease upon presentation of a subject to a health care facility (e.g., a clinic or a hospital). In some instances, a health care professional may diagnose a subject as having a neurodegenerative disease (e.g., ALS) while the subject is admitted in an assisted care facility. Typically, a physician diagnoses a neurodegenerative disease in a subject after the presentation of one or more symptoms.

The present disclosure provides methods of treating ALS or symptoms thereof which comprise administering to a subject (e.g., a mammal, such as a human) a therapeutically effective amount of a pharmaceutical composition comprising a cell expressing a neuroprotective agent, such as an anti-Nox2 shRNA, a miRNA sponge (i.e., an miRNA155 sponge), a metallothionein, or a combination thereof. In some embodiments, the cell is a hematopoietic stem progenitor cell. In some embodiments, the cell is a microglial progenitor cell. Thus, the method in some embodiments comprises administering to the subject a therapeutically effective amount of a cell described herein sufficient to treat ALS or symptom thereof, under such conditions that ALS is treated.

The methods herein include administering to the subject (including a subject identified as in need of such treatment) an effective amount of cells described herein, or a composition comprising such cells as described herein to produce such effect. Such treatment will be suitably administered to a subject, particularly a human, suffering from, having, susceptible to, or at risk for, ALS, or a symptom thereof. In some embodiments, the methods herein include administering to the subject (including a subject identified as in need of such treatment) an effective amount of a compound described herein, or a composition described herein to produce such effect.

In some embodiments, the cell or the composition comprising the cell is administered to a subject in a targeted manner. For example, in some embodiments, a composition comprising a cell expressing an anti-Nox2 shRNA, a miR155 sponge, or a metalloprotein, or a combination thereof, is administered directly to a subject's brain. In some embodiments, the composition is delivered directly to the brain via intracerebroventricular administration. In some embodiments, the composition is delivered in this manner to the lateral ventricles of the subject's brain. Methods of administration useful in the present disclosure are described, for example in International Application No. PCT/US2020/045106, which is incorporated by reference in its entirety.

Alternatively, the composition may be delivered systemically, such as by intravenous administration. Cells administered in such a manner must traverse the blood brain barrier prior to engrafting in the subject's brain. Other modes of administration (parenteral, mucosal, implant, intraperitoneal, intradermal, transdermal, intramuscular, intracerebroventricular injection, intravenous including infusion and/or bolus injection, and subcutaneous) are generally known in the art. In some embodiments, cells are administered in a medium suitable for injection, such as phosphate buffered saline, into a subject. Because the cells being administered to the subject are intended to repopulate microglial cells, intracerebroventricular administration may be advantageous as other routes of administration require crossing the blood brain barrier.

Engraftment of transplanted cells into a subject's brain provides a population of cells that express a therapeutic agent. But because the transplanted cells are meant to replace endogenous cells (i.e., microglial cells), in certain embodiments, methods of treating a subject having, susceptible to, or at risk of developing ALS further comprise administering to a subject prior to administering an HSPC expressing a therapeutic agent, an agent for ablating endogenous microglia. In some embodiments, the agent is an alkylating agent. In some embodiments, the alkylating agent is busulfan. In particular, nanoparticle delivery of alkylating agents may be effective in creating a suitable environment for engraftment of transplanted HSPCs, as described in International Application No. PCT/US2017/056774, the contents of which are incorporated herein by reference in their entirety.

Kits

The present disclosure contemplates kits for the treatment or prevention of ALS. In some embodiments, the kit comprises a composition comprising a modified HSPC expressing a neuroprotective agent. In some embodiments, the neuroprotective protein is an anti-Nox2 shRNA, a miRNA sponge (i.e., an miRNA155 sponge), a metallothionein, or a combination thereof. The kit can include instructions for a treatment protocol, reagents, equipment (test tubes, reaction vessels, needles, syringes, etc.), and standards for calibrating or conducting the treatment protocol. The instructions provided in a kit according to the present disclosure may be directed to suitable operational parameters in the form of a detectable label or a separate insert. Optionally, the kit may further comprise a standard or control information so that the test sample can be compared with the control information standard to determine if a consistent result is achieved. In some embodiments, the kit includes a nanoparticle for ablative conditioning of endogenous microglial cells.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a neurological disease or disorder of the central nervous system. The instructions will generally include information about the use of the composition for the treatment or prevention of the disease or disorder. In other embodiments, the instructions include at least one of the following: description of the therapeutic agent; dosage schedule and administration for treatment or prevention of a neurological disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The following examples provide those of ordinary skill in the art with a complete description of how to make and use the compositions and therapeutic methods of the disclosure, and are not intended to limit the scope of what the inventors regard as their invention.

EXAMPLES

Example 1: Lentiviral Vector Generation and Testing miRNA-155 Sponge Lentivirus (LV) (LV012).

Figure 2A:
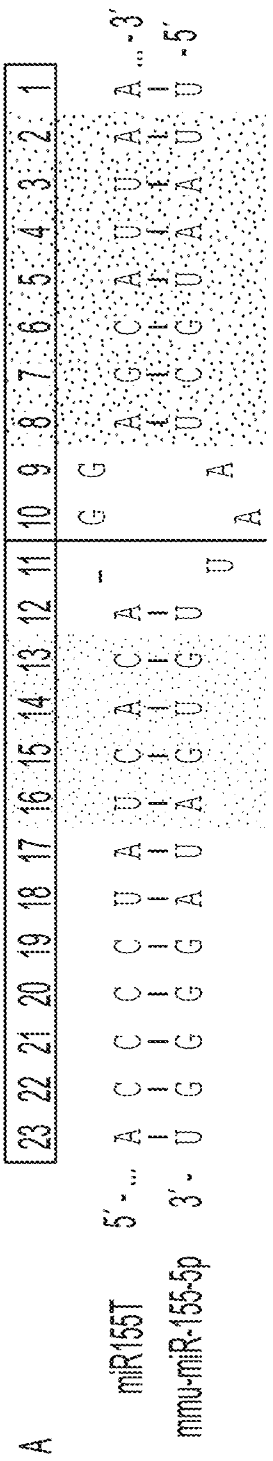
FIGS. 2A and 2B illustrate a micro RNA 155 (miR155) sponge lentiviral vector.
Figure 2B:
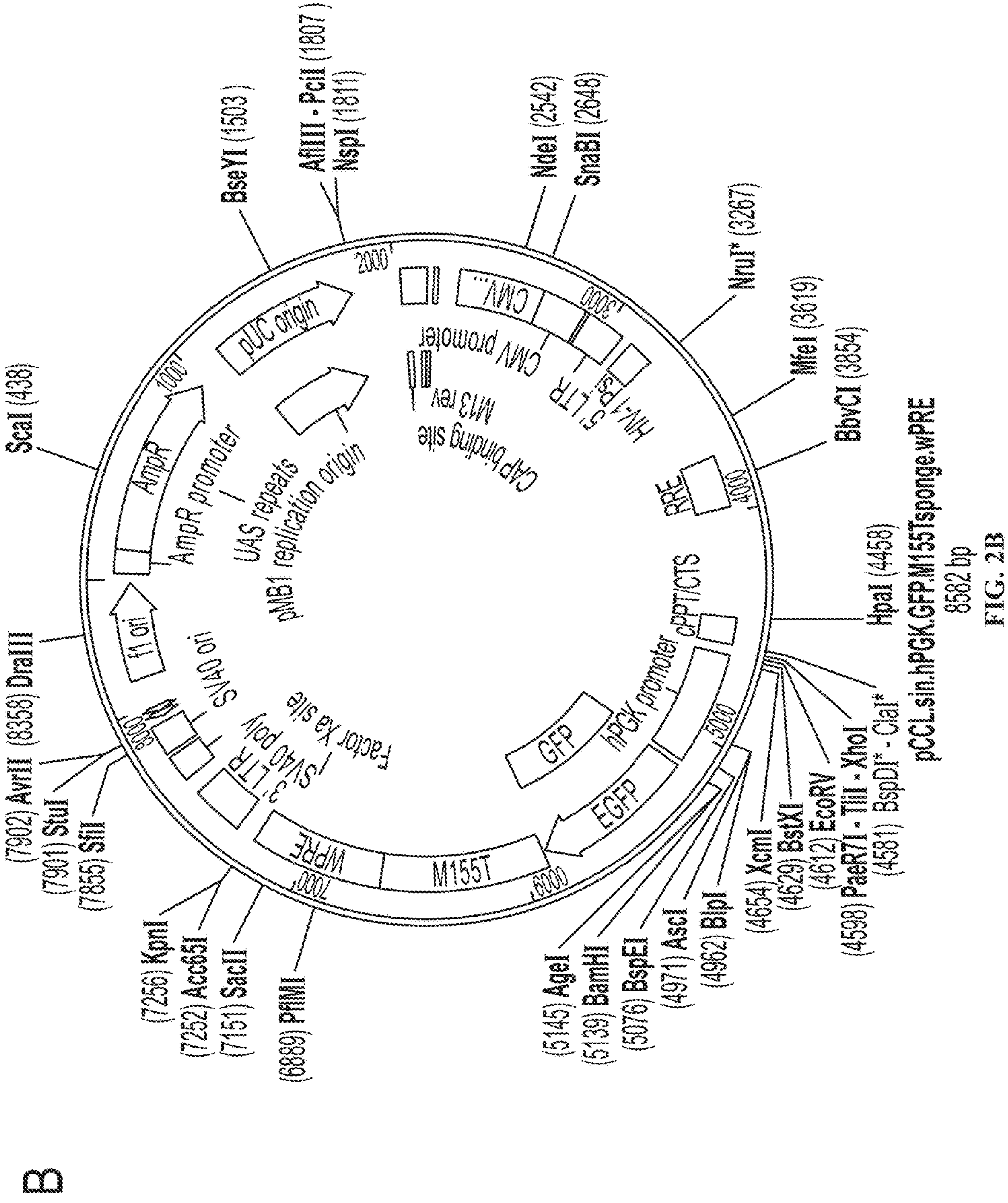

A silencing strategy for miR-155 uses miRNA sponge technology to sequester miR-155, thereby preventing its binding to endogenous targets (Bofill-De Ros et al., BMC Genomics (2015), the contents of which is herein incorporated by reference in its entirety). This results in normalization of gene expression of target genes in activated glial cells and the expected down-regulation of the pathologic cascade driven by miR-155. A lentiviral vector was generated to express EGFP with a 3'-UTR containing 25 complementary binding sites recognizing the murine miR-155 (mir-155-SP) (Bofill-De Ros et al. (2015)). The target sequences in the sponge contain bulged sites that are mispaired at positions 9 to 12, to prevent Ago2 from cleaving the transcript. This allows longer miRNA binding to the transcript and reduces availability of the miRNA to regulate other transcripts (FIG. 2A). A DNA block containing the sponge repeats flanked by restriction enzyme binding motifs was synthetized, and the sponge cloned downstream from a PGK-GFP transfer plasmid resulting in the plasmid shown in FIG. 2B.

Nox2 shRNA Lentivirus (LV) (LV013).

Nox2, also known as Cytochrome b or gp91phox, is encoded in mouse by the Cybb gene on chromosome X. Its product is an essential component of phagocytic NADPH-oxidase, a membrane-bound enzyme complex that generates large quantities of microbicidal superoxide and other oxidants upon activation. Active NADPH oxidase also requires several cytosolic proteins, including p47-phox, p67-phox, p40-phox, and a GTP-binding protein, either ras-related c3 botulinum toxin substrate 1 (RAC1) in macrophages or ras-related c3 botulinum toxin substrate 2 (RAC2) in neutrophils (Leusen et al. (1994), the contents of which is herein incorporated by reference in its entirety).

Small interference RNAs against the mRNA of Nox2 (Hingtgen et al. (2006) and Bae et al. (2009), the contents of which are herein incorporated by reference in their entirety) can inhibit the induction of Nox2 by stimuli, such as toll-like receptor 4, associated with stress and immune activation, and the production of ROS. LEGO design (FIG. 1), which takes advantage of the scaffold of miR223, was used in conjunction with an efficient Pol II promoter to express shRNAs (Brendel et al. (2016), the contents of which is herein incorporated by reference in its entirety) to retarget the dsRNA loop to bind the Nox2 sequence, 5'-CCATTCGGAGGTCTTACTT-3' (SEQ ID NO: 21), that was previously validated for down-regulation of Nox2 (Bae et al. (2009)). The following DNA-Block was synthetized and cloned directionally inside the LEGO vector downstream of the Venus fluorescent reporter:

```
                                          (SEQ ID NO: 22)
5'-TAAGCTTGATATCGAATTCCCCCGGGGGATCTCACTTCCCCACAGAA

GCTCTTGGCCTGGCCTCCTGCAGTGCCACGCTCCATTCGGAGGTCTTACT

TCTCCATGTGGTAGAGAAGTAAGACCTCCGAATGGAGTGCGGCACATGCT

TACCAGTCAGTGCGGCACATGCTTACCAGCTCTAGGCCAGGGCAGATGGG

ATATGACGAATGGACTGCCAGCTGGATACAAGGATGCTCACCGACGTCGA

CGCGTAAGGGCGAATTCCCCCGGGGGATCCACTAGTTCTAGAGCGGCCAA

TTCGTCGAGGGACCTAATAACTTCGTATAGCATACATTATACGAAGTTA

T-3'
```

Example 2: Nox2-Targeted shRNA Inhibited ROS in BV2 Cells

The cloned transfer vector was employed for the production of high titer VSV-G-pseudotyped lentiviral vectors (LVs), and titrated in HEK293T cells. Lentiviral function was validated in BV-2 microglia cells. Cells were transduced in bulk and propagated for at least 2 weeks to allow for dilution of non-integrated vector.

Figure 4:
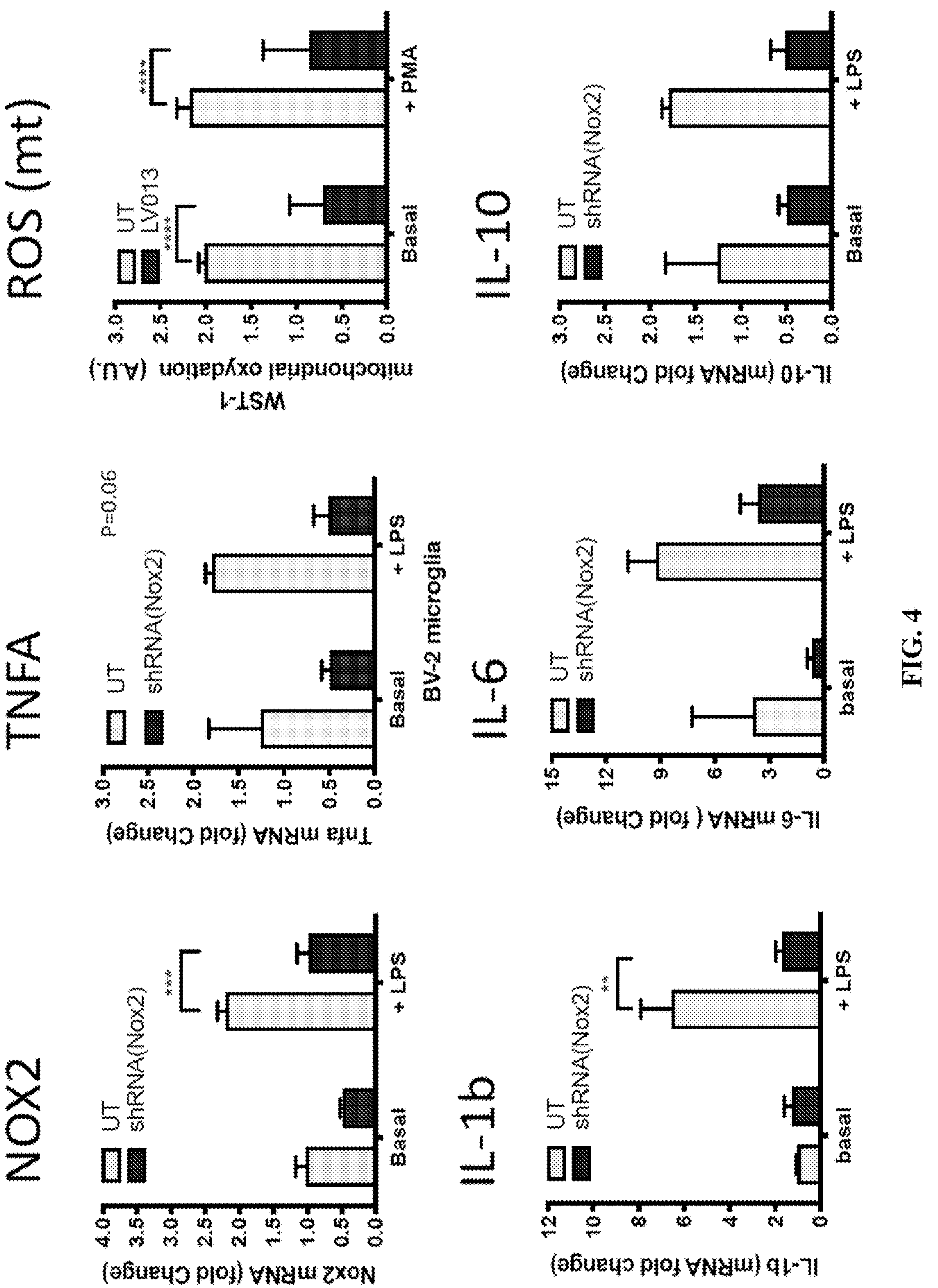
FIG. 4 presents bar graphs presenting Nox2 validation on mouse microglia cells. The BV-2 mouse microglia cell line was transduced with LV013 (Nox2 shRNA). Activation of the cells was forced by incubating them in presence of the lipopolysaccharide (LPS) and the mRNA levels of NOX2 and TNFA, and of ROS were compared. In presence of the Nox2 shRNA a down regulation of NOX2 was measured in basal and activated state, and prevention of LPS-dependent increased expression of TNFA and of ROS was measured. Also the increase of several amyotrophic lateral: sclerosis (ALS) hallmark inflammatory cytokines (IL-1b, Il-6, IL-10) was buffered in Nox2-shRNA transduced BV-2 cells upon lipopolysaccharide (LPS) stimulation. Mean+/−SD.

Microglia cells transduced with the Nox2 shRNA vector exhibited a 60% reduction of basal Nox2 mRNA levels (FIG. 4). Likewise, upon LPS induction, transduced cells had lower levels of Nox2. TNFalpha, a major activation molecule, mRNA levels were also reduced in BV-2 transduced cells under basal conditions and upon lipopolysaccharide (LPS) stimulation. The WST-1 assay also revealed lower reactive oxygen species (ROS) levels in the transduced BV-2 cells versus untransduced cells, both in basal conditions and under PMA (phorbol myristate acetate) activation. Cytokines IL-1b, IL-6 and IL-10, that are increased in ALS patients due to chronic microglia activation, were also reduced following lipopolysaccharide (LPS) induction in BV-2 cells transduced with the Nox2 shRNA (FIG. 4).

Example 3: Tnf-α Levels, a Marker of ALS, were Reduced by the miR-155 Sponge

Figure 3A:
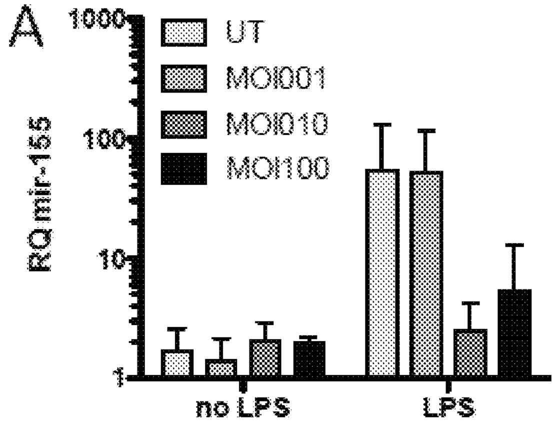
FIGS. 3A to 3E illustrate the effects of miR155 sponge lentiviral vector transduction on target expression in BV2 cells stimulated by lipopolysaccharide.
Figure 3B:
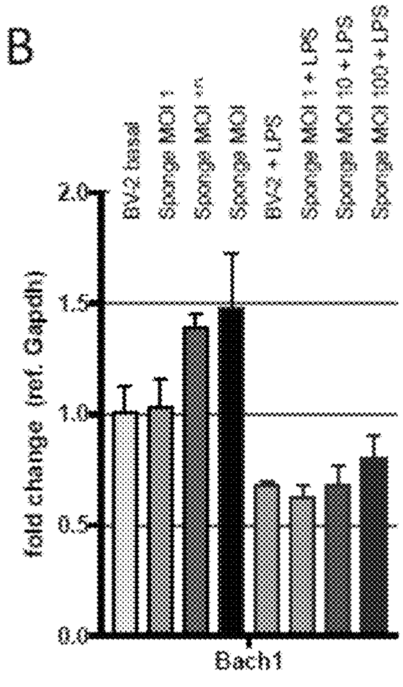
Figure 3C:
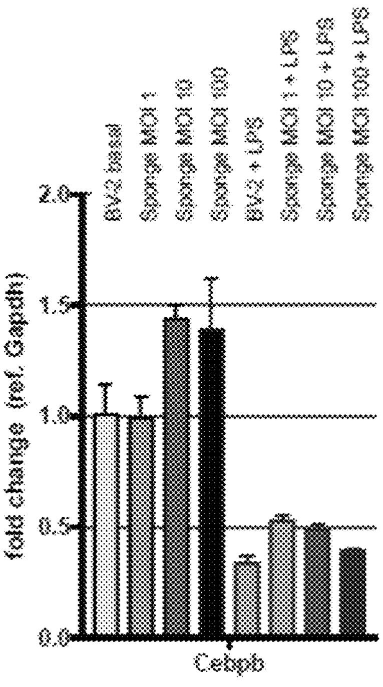
Figure 3D:
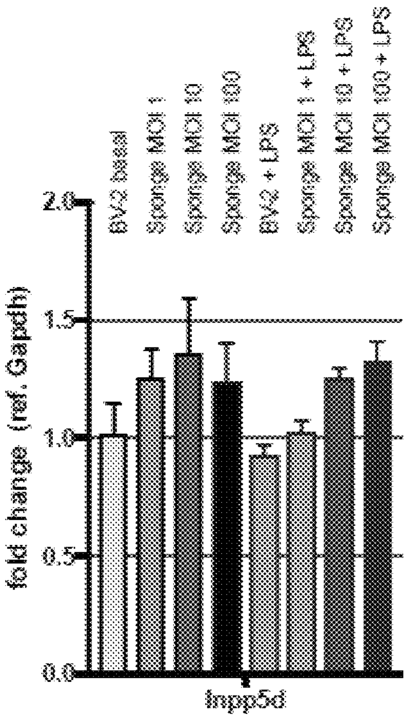
Figure 3E:
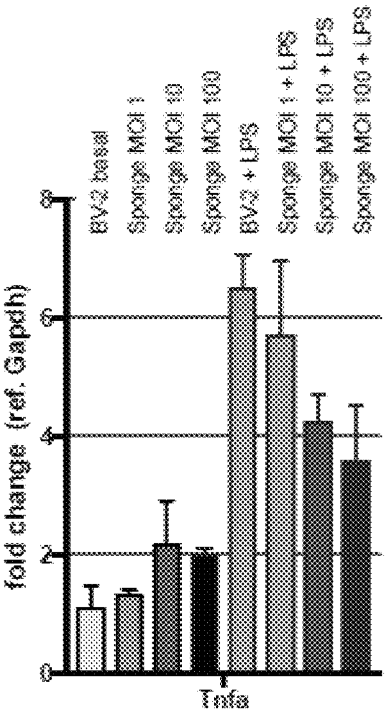

The miR-155 sponge plasmid was amplified to produce concentrated VSV-G pseudotyped lentiviral supernatants to test the effect of miR-155 down regulation on mouse microglia. Without wishing to be bound by theory, microglia cells are expected to express low levels of mir-155, but to increase miR-155 expression in the presence of an appropriate stimulus. LPS was chosen as the stimulus because it is an agonist of the TLR4. First, a BV-2 microglia cell line was transduced efficiently at different multiplicities of infection (MOIs). The transduced bulk population was cultured for several passages before testing to obtain a population with a stable vector copy number. miR155 in the stably transduced cells was quantified to assess the vector sponge sequestration of the miRNA produced following LPS stimulation. These studies demonstrated the functionality of the lentiviral vector sequence (FIG. 3A). mRNA levels of a set of genes that are putative mir-155 targets in microglia cells in ALS models (Butovsky et al. (2015)) were then quantified.

Bach1, Carhsp1, Cebpb, Csf1r, Inpp5d (Ship-1) and Pea15a were predicted to be miR-155 targets. Olfml3 and Sall1 are key microglia genes that were also predicted to be miR-155 targets. Tumor necrosis factor alpha (Tnf-α) mRNA levels were also measured as an indirect indicator of ALS. Under basal conditions, presence of the miR-155 sponge reduced the available miR-155 resulting in an increase in the expression of some target genes (FIGS. 3B-3E). Likewise, LPS increased mir-155 levels and reduced the expression of certain direct targets in the absence of the miR-155 sponge. In the case of Tnf-α, the mRNA increased in untransduced microglia cells in response to LPS and its levels were reduced in the presence of the miR-155 sponge. Some of the direct miR-155 targets (Bach1, Cebpb, and Inpp5d) and one indirect target (Tnfa) confirmed the effect of the miR-155 sponge in microglia (FIGS. 3B-3E).

Example 4: Hematopoietic Stem Cells (HSC) Gene Therapy in SOD1G93A Amyotrophic Lateral Sclerosis (ALS) Mice The SOD1G93A is a transgenic mouse model with up to 26 copies of the human mutant SOD1 that develops a syndrome similar to the amyotrophic lateral sclerosis (ALS) progression in humans. These animals were used as reliable disease models to test the efficacy of an intra-CNS (central nervous system) gene therapy approach.

Seven week-old male SOD1 donors were employed to purify lineage-Hematopoietic Stem and Progenitor Cells (HSPCs), equivalent to CD34+ HSCs in humans, from the bone marrow. Cells were then transduced over night with lentiviral vectors (LVs) LV012 or LV013 at MOI (multiplicity of infection)=100 or co-transduced at MOI (multiplicity of infection)=75 for the groups featuring metallothionein's. Green fluorescent protein (GFP) expression after 2 weeks of liquid culture expansion was comparable with LV 012 and LV013, and indicative of high transduction (>80% in all conditions). The percentage of green fluorescent protein (GFP) positive cells by fluorescence-activated cell sorting (FACS) was lower when cells were cotransduced with the MT1G vector as it did not contain a green fluorescent protein (GFP) reporter and transduction was conducted at MOI (multiplicity of infection)-75. Vector copy number (VCN) in the transduced cell liquid culture progeny ranged between 2 and 14 copies/genome, with the miR-155-SP alone or in combination with MT1G the cohort with the higher number of detected copies per cell.

Figure 5:
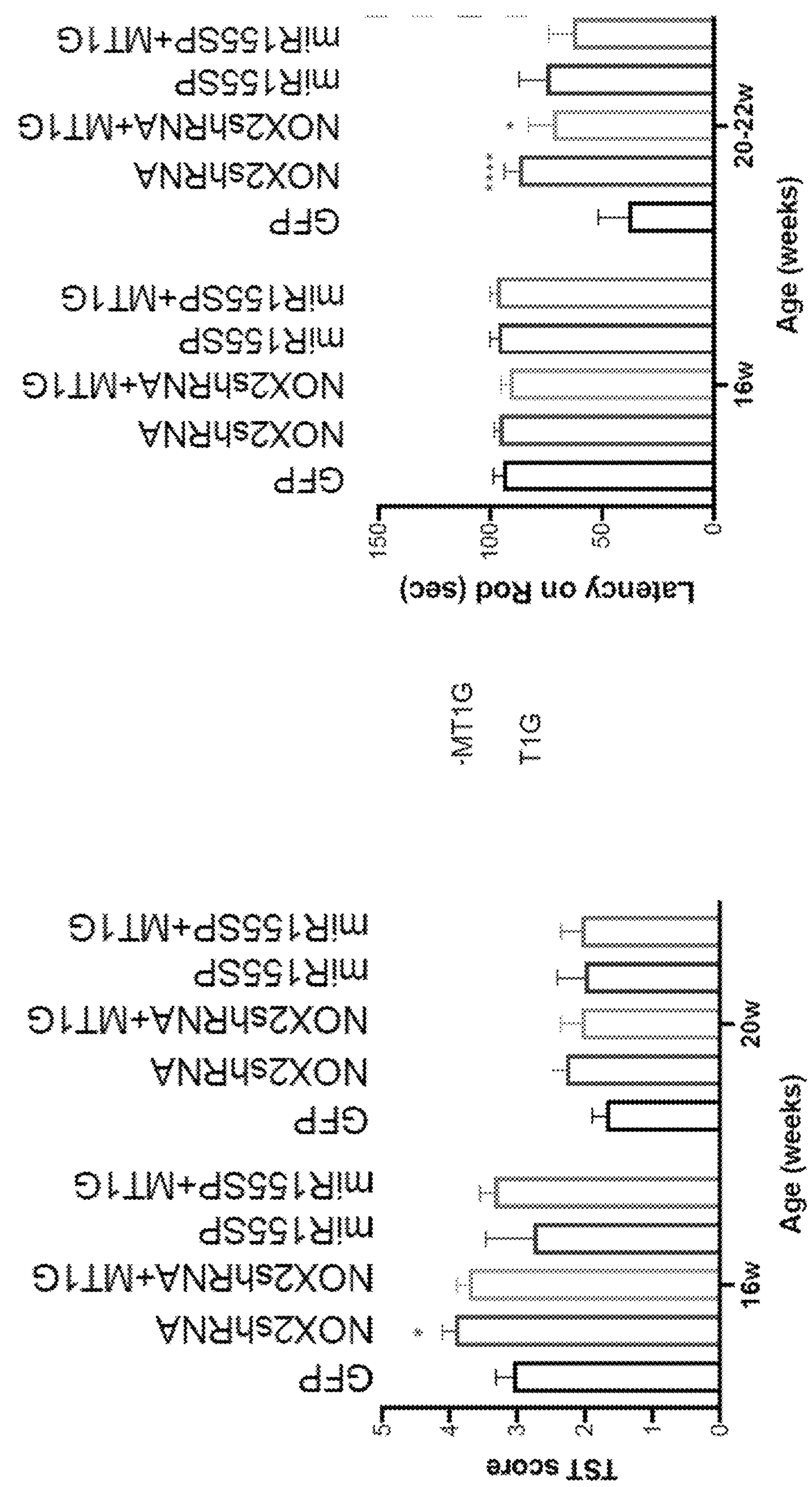
FIG. 5 is bar graphs of behavioral performance of hematopoietic stem cell (HSC) gene therapy treated SOD1 mice. The left panel of FIG. 5 presents Tail Suspension Test (TST) score results. Mice were suspended from the tail and the position and state of the hind limbs scored from 4, normal muscle and leg mobility; 3, reduced mobility, loss of muscle; 2, impaired mobility and muscle loss; 1, nonfunctional mobility and foot pad still can push; and 0, paraplegia. Animals were tested from the age of 12 weeks old, here data at 16 and 20 weeks (w) of age are shown. (* significance at unpaired t test versus green fluorescent protein (GFP) controls). The right panel of FIG. 5 prevents Rotarod test results. The animals were positioned on a rotating bar and subjected to the test measurement of motor coordination (rotarod is set to accelerate from zero rpm to 40 over the course of 120 seconds). The latencies to fall from the rotarod were recorded for each mouse for each run. If the mice fell off the rod before 120 sec, animals were given 5 minutes rest; then the trial was repeated up to maximum of 5 times. Best latency is here shown. Animals were tested from the age of 12 weeks old, here data at 16 and 20 weeks (w) of age are shown. (* significance at One Way Anova versus GFP control with Dunnet's correction). Mean+/−SEM.

Transduced SOD1 lin− cells were then infused into 6-8 weeks old female SOD1 mice. Recipients were pre-conditioned with 4 doses of busulfan 25 mg/kg i.p. (intraperitoneal injection), 24 hours apart starting 5 days prior to hematopoietic stem cell transplantation (HSCT). Twenty-four hours after last busulfan dose, each recipient received 300,000 transduced lin− in a single intra-cerebral ventricular (ICV) injection, as per Table 1 below. Control animals received GFP LV transduced SOD1 lin− cells. Five days after the intra-cerebral ventricular (ICV) transplant, all 10 recipients received 2 million total bone marrow cells from SOD1 donors, un-transduced, hematopoietic support infused in the tail vein.

phases, but mice cannot perform these tests in the late and end-stage while in many cases they can still maintain certain performance at Rotarod. Interestingly, at TST test animals transplanted with cells transduced with the LV012 (encoding Nox2 ShRNA) showed a delay in the early manifestations of the disease (at Tail Suspension Test (TST) test done at 16 weeks of age) at comparison with mock transplanted mice (FIG. 5). the grid test was poorly informative due to variability in treated and control mice performance. At the Rotarod test performed at 20 weeks of age, Nox2 ShRNA treated mice had a significantly better score than the control SOD1 mice. The addition of MT1G lentiviral vector (LV) did not affect the outcome of the treatment at behavioral assessment. LV013 treatment did not result in significant evidence of benefit at behavioral testing.

TABLE 1

| Experimental groups | | | | | | |
|---|---|---|---|---|---|---|
| GROUP | VECTOR | DONOR | RECIPIENT | CONDITIONING | TRANSPLANT | SUPPORT |
| A | NOX2_shRNA | SOD1 G93A | SOD1 G93A; 6-7 weeks | Busulfan: 4 × 25 mg/kg | ICV 300,000 lin-; MOI 100 | IV 2,000,000 tBM (5 dpt) |
| B | MiR-155T-SP | SOD1 G93A | SOD1 G93A; 6-7 weeks | Busulfan: 4 × 25 mg/kg | ICV 300,000 lin-; MOI 100 | IV 2,000,000 tBM (5 dpt) |
| C | GFP | SOD1 G93A | SOD1 G93A; 6-7 weeks | Busulfan: 4 × 25 mg/kg | ICV 300,000 lin-; MOI 100 | IV 2,000,000 tBM (5 dpt) |
| D | A + 4xMT1G | SOD1 G93A | SOD1 G93A; 6-7 weeks | Busulfan: 4 × 25 mg/kg | ICV 300,000 lin-; MOI 75 each | IV 2,000,000 tBM (5 dpt) |
| E | B + 4xMT1G | SOD1 G93A | SOD1 G93A; 6-7 weeks | Busulfan: 4 × 25 mg/kg | ICV 300,000 lin-; MOI 75 each | IV 2,000,000 tBM (5 dpt) |
| F | C + 4xMT1G | SOD1 G93A | SOD1 G93A; 6-7 weeks | Busulfan: 4 × 25 mg/kg | ICV 300,000 lin-; MOI 100 | IV 2,000,000 tBM (5 dpt) |

Amyotrophic lateral sclerosis (ALS) onset in SOD1 females occurs at about 12-14 weeks of age and in early stages (at 14-16 weeks) and can be spotted as a loss of performance in behavioral tests together with a loss of muscle in the hinder legs. Late symptomatic SOD1 females (16-18 weeks) suffer a rapid decay of behavioral performance and arrive to human end point around 20-21 weeks of age.

Figure 6A:
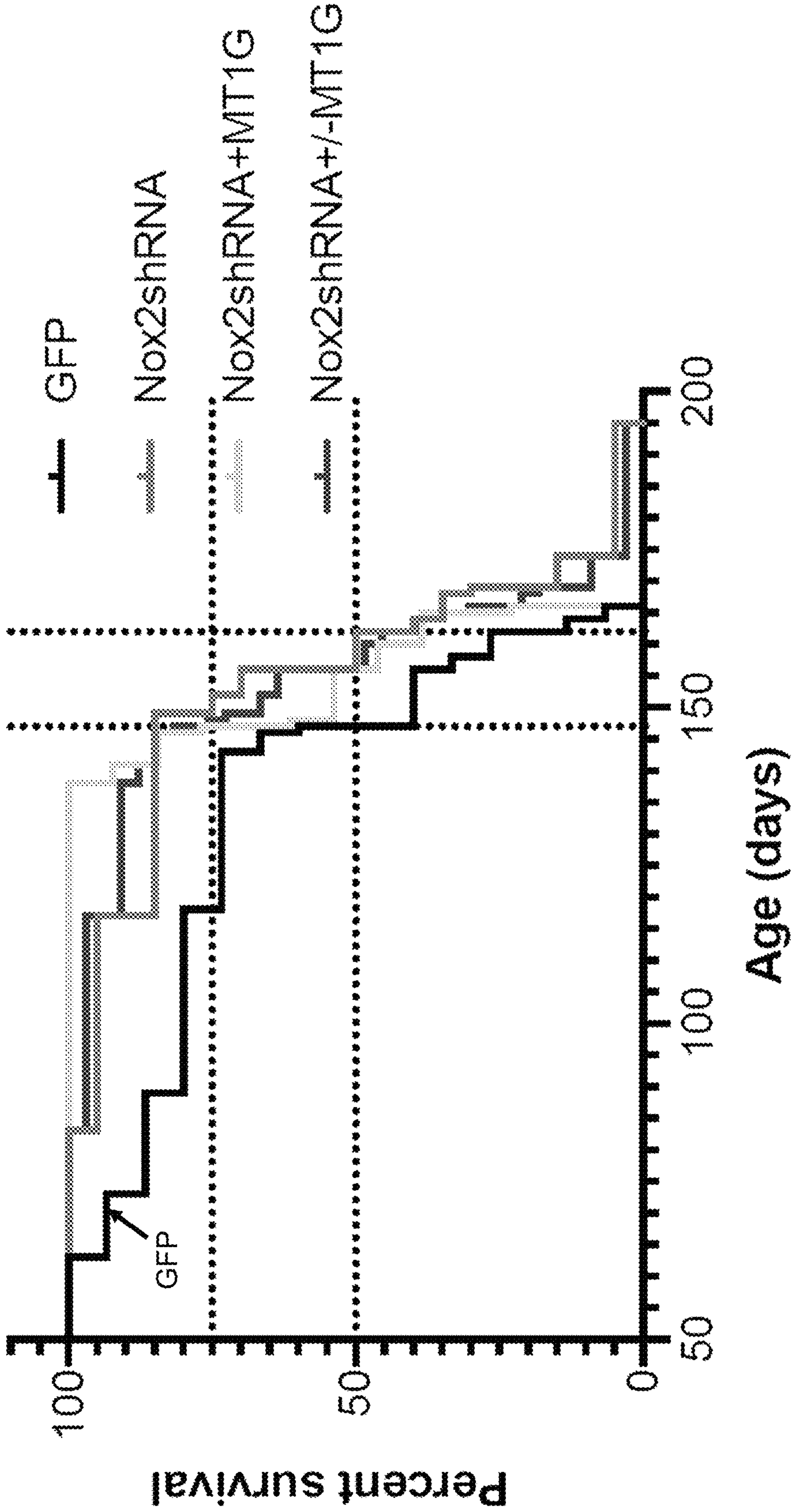
FIGS. 6A and 6B are survival curves. Transplanted mice survival were plotted in a Kaplan-Meyer to compare the different groups.
Figure 6B:
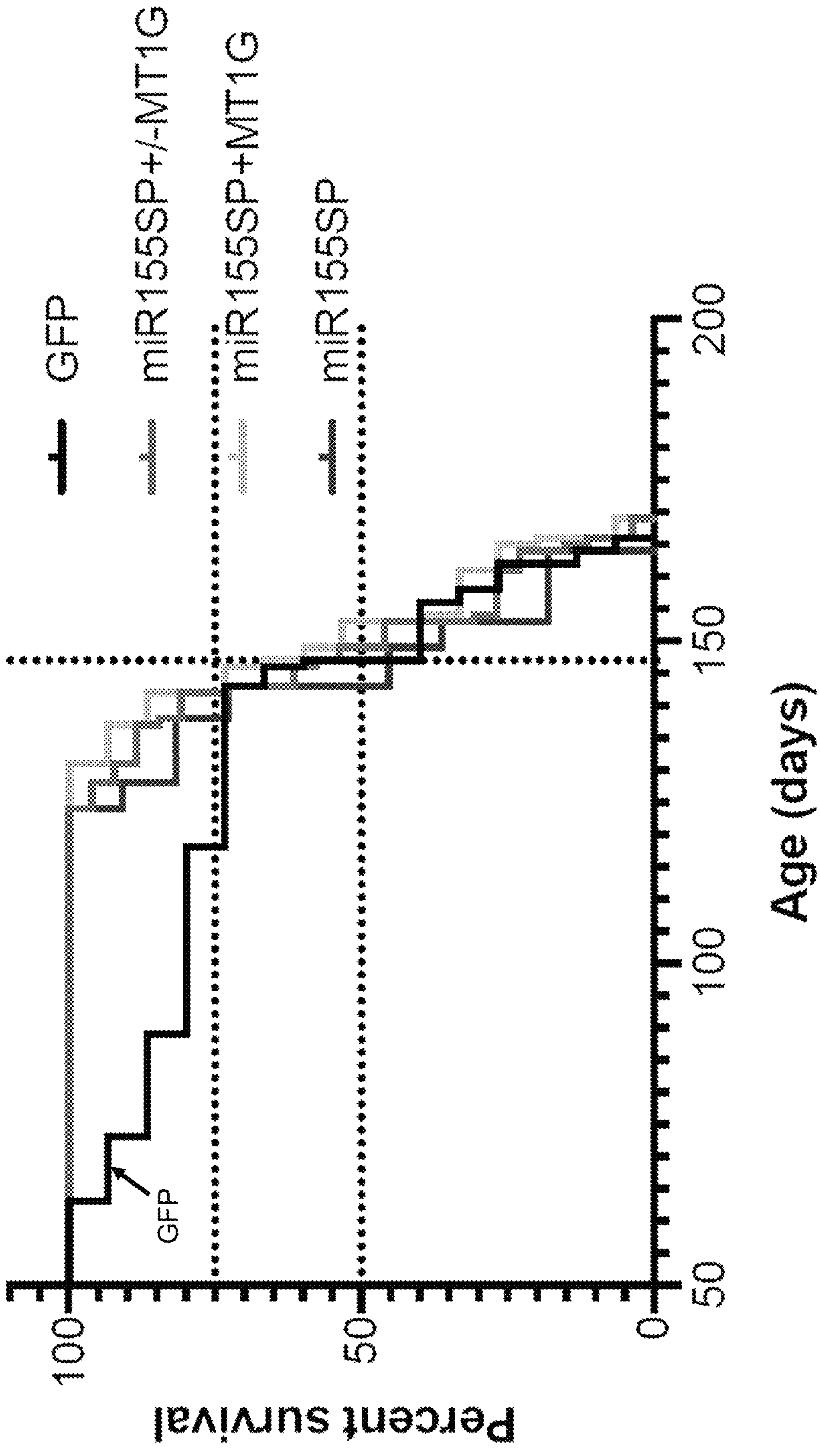

Starting 4 weeks after the transplant, mice (which reached 10-12 weeks of age) were enrolled in behavioral monitoring to evaluate the impact of the transplant of the transduced hematopoietic stem cells (HSCs) on the onset and progression of amyotrophic lateral sclerosis (ALS) symptoms. Behavioral evaluation of these mice consisted in a series of tests that included the Tail Suspension Test (TST), the Rotarod test for coordination and balance, and grid test to evaluate grip and strength. Tail Suspension Test (TST) and grid capture changes in performance at onset and early Treated and control animals were then evaluated for long term survival. Interestingly, Nox2 shRNA mice showed an extended lifespan as compared to green fluorescent protein-(GFP) treated controls. (FIG. 6A and Table 2). Survival of animals treated with the miR-155-SP lentiviral vector (LV), despite a trend of increased survival in early phases, did not show a significantly improved survival versus controls (FIG. 6B and Table 2). Also in this case, addition of MT1G lentiviral vector (LV) did not modify the outcome of the treatment with each of the vectors.

TABLE 2

| Treated and control mice survival | | | | | |
|---|---|---|---|---|---|
| Group | GFP | Nox2shRNA | Nox2shRNA + MT1G | miR155SP | miR155SP + MT1G |
| Average survival (days) | 136 | 159 | 156 | 145.6 | 152 |
| SD | 34 | 24.5 | 10 | 12.8 | 11 |
| p vs GFP (Log Rank) | na | 0.0092 | ns | ns | ns |

For humane end point, ethical guidelines for amyotrophic lateral sclerosis (ALS) models were followed and when animals arrived to last stage of the disease they were euthanized. End stage disease occurred when the animals showed a loss of 25% of the peak body weight, complete paralysis of the hind limbs and an inability to navigate their surroundings (lagging 30 seconds or more to right themselves after laying them on aside). At this point mice were anesthetized following IACUC (Institutional Animal Care and Use Committee) guidelines and perfused to analyze central nervous system (CNS) tissues, as fresh by flow cytometry and fixed by immunohistochemistry (IHC).

Figure 7A:
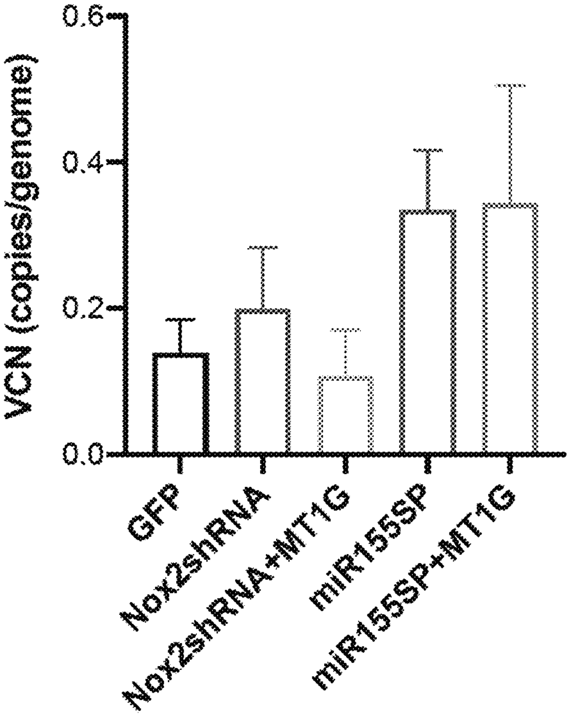
FIGS. 7A to 7C are bar graphs of engraftment quantification in treated and control SOD1 mice.
Figure 7B:
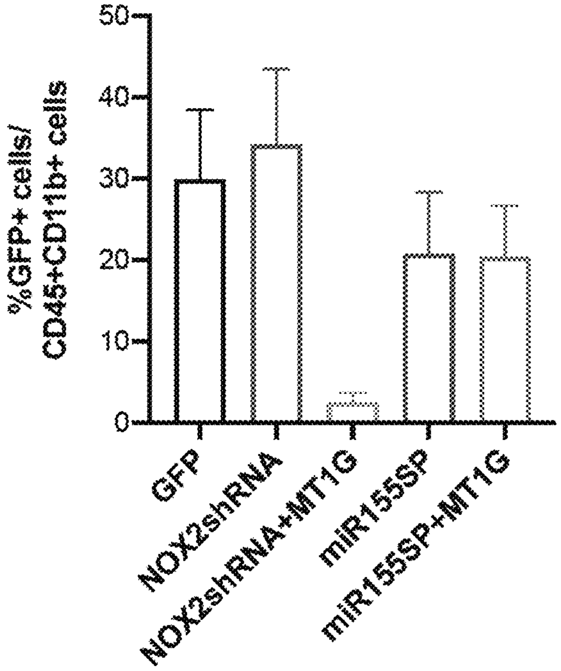
Figure 7C:
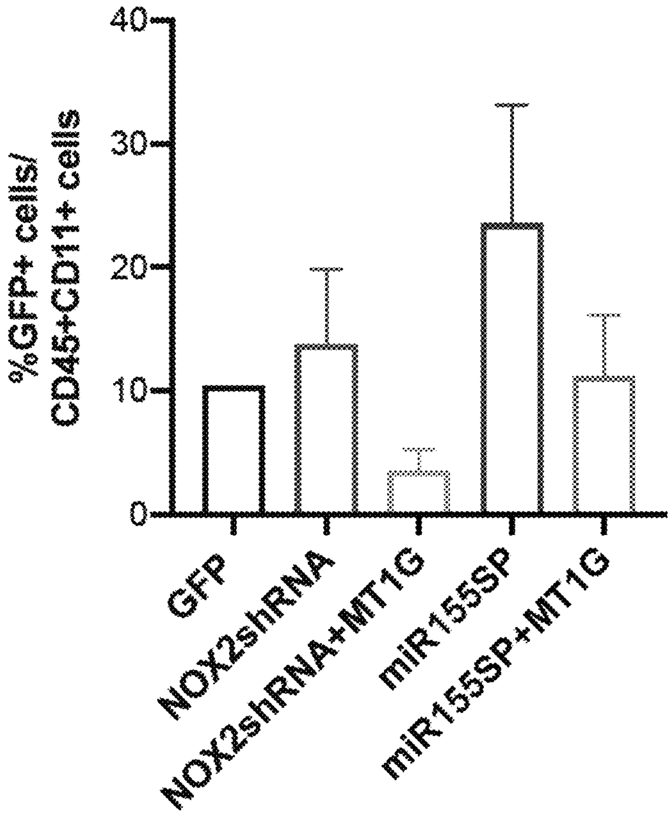

Vector copy number (VCN) and % GFP+ cells were measured on the brain tissue of treated and control mice as a measure of engraftment of the transplanted cells (FIG. 7A). For the evaluation of the GFP-labeled cell chimerism in the microglia compartment, brains and spinal cords were processed with Papain digestion and centrifugation, and then subjected to flow cytometry staining and reading; the % of GFP+ cells within the myeloid (CD45+, CD11b+) compartment was measured (FIGS. 7B and 7C). Despite some variability in each group, a generally low but solid engraftment was documented in the brain and spinal cord of treated and control animals. The groups with the co-transduction with the MT1G LV had a lower engraftment as compared to the other groups.

Figure 8A:
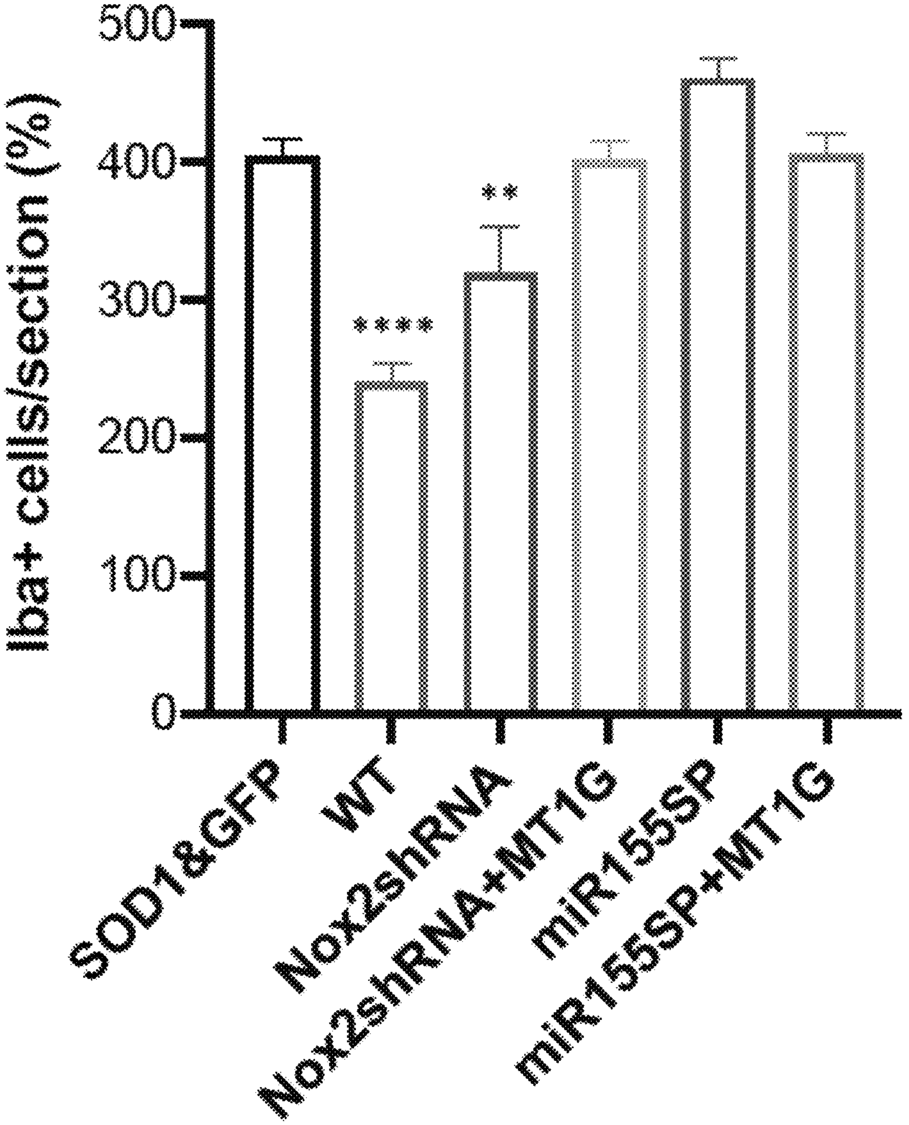
FIGS. 8A and 8B are a bar graph and images for Iba1 staining of spinal cords from SOD1 transplanted mice. Half spinal cord was fixed in PFA 4% and preserved in sucrose 30%. Lumbar sections were stained with anti-IBA1 antibody to visualize microglia cells.
Figure 8B:
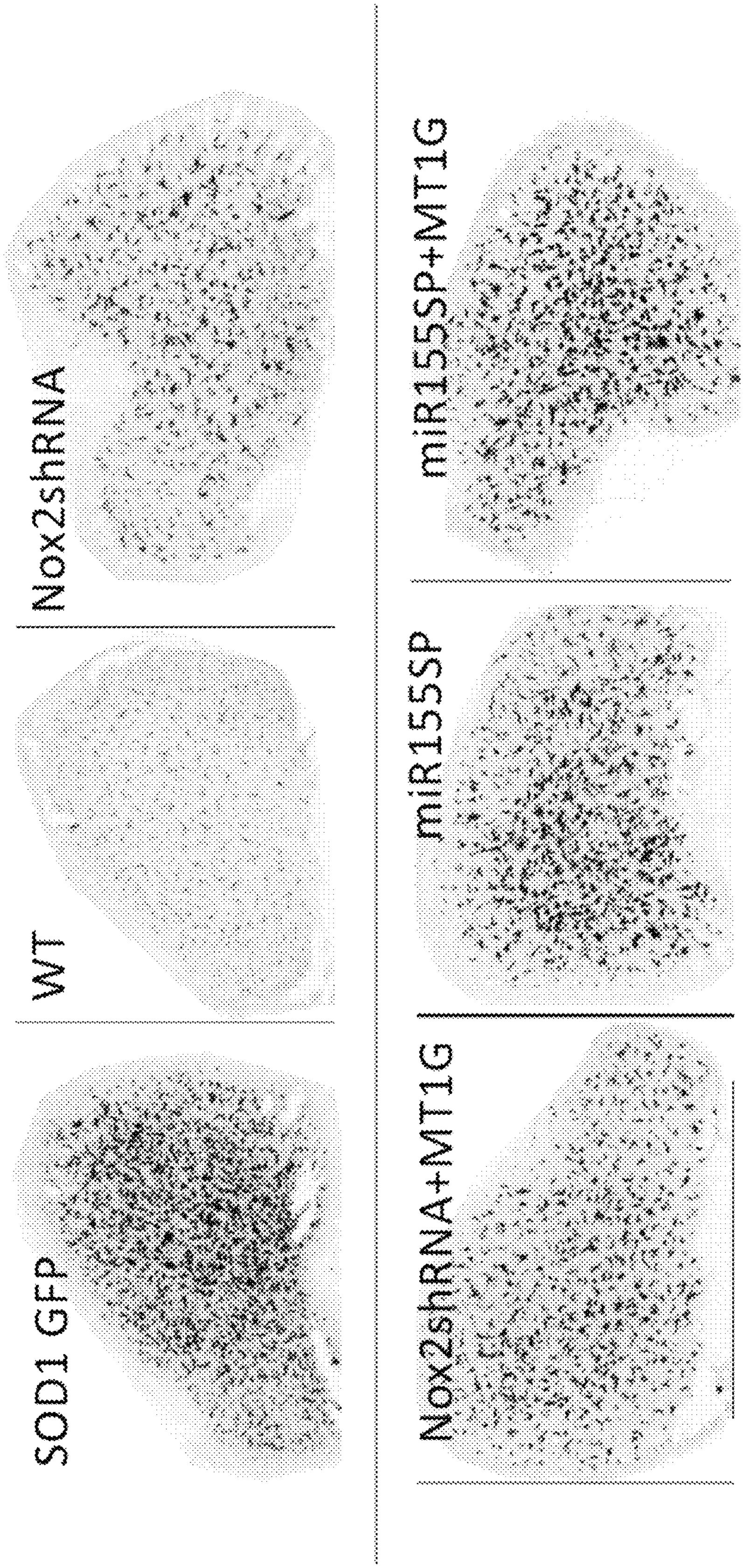
Figure 9:
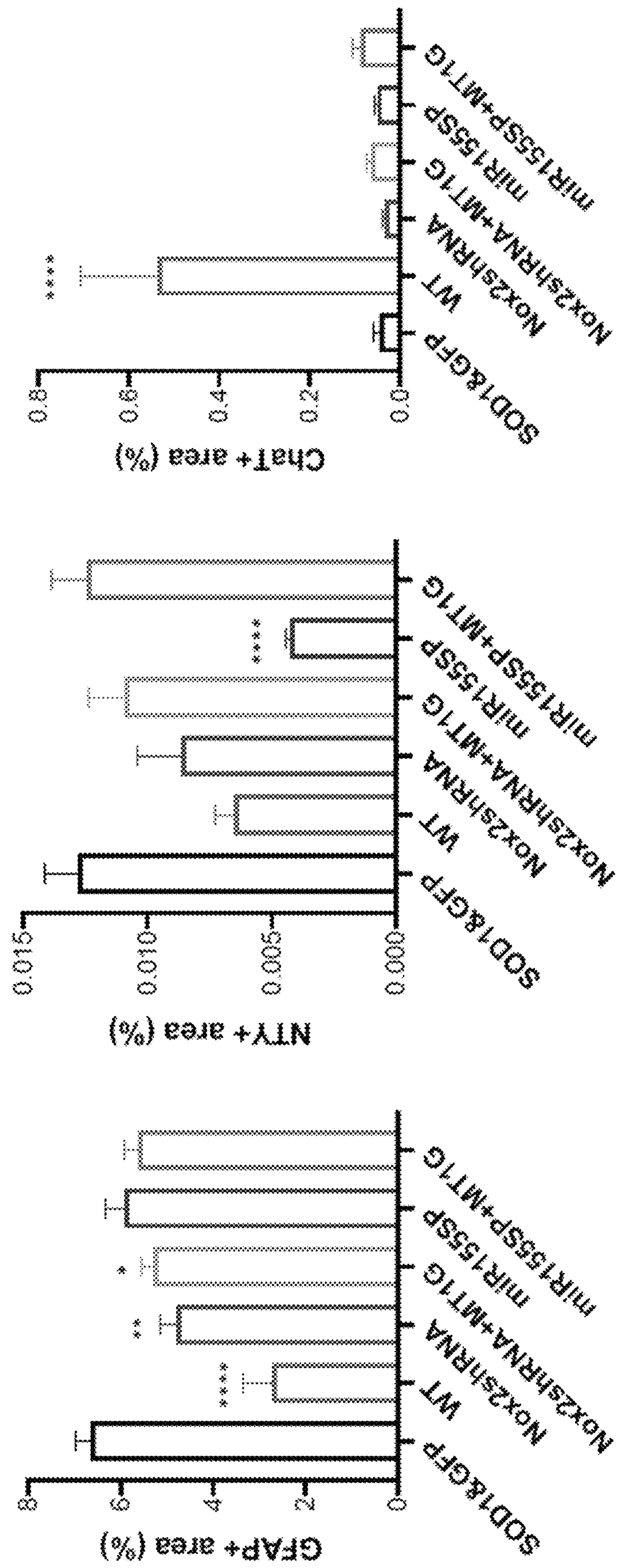
FIG. 9 provides bar graphs for GFAP, NYT and ChAT staining of spinal cords from SOD1 transplanted mice. Spinal cord lumbar sections from treated and control mice were stained with anti-GFAP, NYT and ChAT antibodies to visualize astrocytes (GFAP), ROS modified proteins (NYT) and motor neurons (ChAT). The signals were quantified as indicated (Mean+/−SEM) (asterisks indicate significance versus SOD&FP controls, at One Way Anova with Dunnet's posttest).

Part of the tissues (brain and spinal cord) were preserved for histological analyses. Lumbar slices of the spinal cord were stained to evaluate microgliosis (IBA1 staining) (FIGS. 8A and 8B), astrogliosis (GFAP staining, FIG. 9) and motoneuron preservation (ChAT staining, FIG. 9). 3-Nitrotyrosine (NYT) staining was finally performed to identify ROS modified proteins (FIG. 9).

These staining's and their quantification demonstrated a reduction of disease-associated neuroinflammatory features (reduction of Iba1 and GFAP signals) in Nox2 ShRNA treated animals versus GFP SOD1 controls. miRNA-155 SP lentiviral vector (LV) treatment did not exert a clear effect. As in previous evaluations, addition of MT1G lentiviral vector (LV) did not modify the outcome of the treatment with each of the vectors.

Reactive oxygen species (ROS) modified protein quantification (FIG. 9) showed a reduction in Nox2-treated animals versus SOD1 controls; unexpectedly, miR155 SP-treated animals (only the cohort without MT1G addition), showed a robust reduction of NYT signal. ChAT staining (FIG. 9) failed to reveal substantial treatment-related effects likely because animals were evaluated at human end point when disease progression reached terminal stages.

An hematopoietic stem cell (HSC) gene therapy strategy for treatment of amyotrophic lateral sclerosis (ALS) was tested in the most studied disease animal model (SOD1 mice) based on lentiviral vector (LV)-mediated HSC engineering to express in their microglia-like tissue progeny i) a small hairpin RNAs (shRNAs) targeted to NOX2 for its down-regulation and ii) a string composed of 25 miR-155 targets to sequestrate miR-155 and modulate its biological effects, driving a shift of microglia activation towards a neurosupportive phenotype. In both settings the potential synergic effects of MT1G expression in addition to that of the two therapeutic constructs was tested.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference. This application may be related to PCT/US2020/045106 and PCT/US2017/056774, as well as the PCT applications, entitled "MICROGLIA SPECIFIC PROMOTERS AND METHODS OF USE THEREFORE" and "COMPOSITIONS AND METHODS FOR TREATING ALZHEIMER'S DISEASE", each filed Oct. 1, 2020, which claim priority to the following provisional applications, respectively, 62/908,966 and 62/908,913, all of which are incorporated herein by reference.

What is claimed is:

1. A short hairpin RNA molecule (shRNA) that targets a Nox2 polynucleotide, the shRNA comprising the following sequence (SEQ ID NO: 1):

```
                         ▼
5' C    CCUCCU         A                       -
    CUGG      GCA-GUGCC CGCUNNNNNNNNNNNNNNNNNNN-
                                               -
    GACC      CGU CACGG GUGANNNNNNNNNNNNNNNNNNN-
3'UC    ---AUU   A     C                       -


     CAU
NNCUC   G
         U
NNGAG   G
     AUG.
```

2. The shRNA of claim 1, further comprising 5' and 3' flanking sequences derived from miR223.

3. A method of reducing a pro-inflammatory response in a cell, the method comprising contacting the cell with an shRNA targeting Nox2 of claim 1, thereby reducing pro-inflammatory response.

4. The method of claim 3, wherein the cell is further contacted with a metallothionein or a polynucleotide encoding the metallothionein.

5. The method of claim 3, wherein the method reduces expression of one or more polypeptides selected from the group consisting of Iba1, Nox2, Arg-1, Mrc-1, Tnfa, IL-1b, Il-6 and Il-10, and/or Bach1, Carhsp1, Cebpb, Csf1r, Inpp5d (Ship-1), Pea15a Olfml3 and Sall1, and Tnf alpha or a polynucleotide encoding the polypeptide.

6. A method of treating a subject having or having a propensity to develop amyotrophic lateral sclerosis (ALS), the method comprising administering to the subject an effective amount of a composition comprising a cell comprising an shNox2 of claim 1, thereby treating ALS.

7. The method of claim 6, wherein the cell is hemizygous for the CX3CR1 gene.

8. The method of claim 6, wherein the method reduces expression of one or more polypeptides selected from the group consisting of Iba1, Nox2, Arg-1, Mrc-1, Tnfa, IL-1b, Il-6 and Il-10 and/or Bach1, Carhsp1, Cebpb, Csf1r, Inpp5d (Ship-1), Pea15a Olfml3 and Sall1, and Tnf alpha or a polynucleotide encoding said polypeptide.

* * * * *